US011965210B2

(12) United States Patent
Davis et al.

(10) Patent No.: US 11,965,210 B2
(45) Date of Patent: *Apr. 23, 2024

(54) NANOPORE BASED MOLECULAR DETECTION AND SEQUENCING

(71) Applicant: Roche Sequencing Solutions, Inc., Pleasanton, CA (US)

(72) Inventors: Randall Davis, Pleasanton, CA (US); Roger Chen, Saratoga, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 468 days.

This patent is subject to a terminal disclaimer.

(21) Appl. No.: 16/851,884

(22) Filed: Apr. 17, 2020

(65) Prior Publication Data

US 2020/0308641 A1    Oct. 1, 2020

Related U.S. Application Data

(63) Continuation of application No. 15/703,909, filed on Sep. 13, 2017, now Pat. No. 10,662,471, which is a (Continued)

(51) Int. Cl.
*C12Q 1/6869* (2018.01)
*C12Q 1/6874* (2018.01)
*G01N 33/487* (2006.01)

(52) U.S. Cl.
CPC ......... *C12Q 1/6869* (2013.01); *C12Q 1/6874* (2013.01); *G01N 33/48721* (2013.01)

(58) Field of Classification Search
None
See application file for complete search history.

(56) References Cited

U.S. PATENT DOCUMENTS 6,362,002 B1 * 3/2002 Denison ........... G01N 33/48721
                                                          435/6.12
10,662,471 B2 * 5/2020 Davis .................. C12Q 1/6869
(Continued)

FOREIGN PATENT DOCUMENTS

JP    2003503007 A    1/2003
JP    2009529876 A    8/2009
(Continued)

*Primary Examiner* — Robert T. Crow
(74) *Attorney, Agent, or Firm* — FisherBroyles, LLP; Jason M. Pass

(57) ABSTRACT

This disclosure provides systems and methods for molecular identification and polymer (e.g., nucleic acid) sequencing using nanopores. The polymer may be passed through or in proximity to the nanopore and various subunits of the polymer may affect the current flowing through the nanopore. The various subunits may be identified by measuring the current at a plurality of voltages applied across the nanopore and/or membrane. In some cases, the polymerization of tagged nucleotides presents tag molecules to the nanopore that can be identified by measuring the current at a plurality of voltages applied across the nanopore and/or membrane. Also provided herein are systems and methods for sequencing both the sense and anti-sense strand of a double stranded nucleic acid molecule with a nanopore and methods for using ribonucleic acid (RNA) speed bump molecules to slow the passage of a nucleic acid molecule through or in proximity to a nanopore.

12 Claims, 37 Drawing Sheets

Specification includes a Sequence Listing.

Related U.S. Application Data continuation of application No. 13/745,688, filed on Jan. 18, 2013, now abandoned.

(60) Provisional application No. 61/600,227, filed on Feb. 17, 2012, provisional application No. 61/589,719, filed on Jan. 23, 2012, provisional application No. 61/589,196, filed on Jan. 20, 2012.

(56) References Cited

U.S. PATENT DOCUMENTS

| | | | | |
|---|---|---|---|---|
| 2003/0099951 | A1* | 5/2003 | Akeson | C12Q 1/6827 204/461 |
| 2005/0186629 | A1* | 8/2005 | Barth | B81C 1/00087 204/450 |
| 2009/0029477 | A1* | 1/2009 | Meller | G01N 33/48721 436/94 |
| 2010/0035260 | A1* | 2/2010 | Olasagasti | G01N 27/3278 435/6.16 |
| 2011/0005918 | A1* | 1/2011 | Akeson | C12Q 1/54 204/403.01 |
| 2011/0037486 | A1* | 2/2011 | Zhang | G01N 33/48721 324/663 |
| 2011/0236984 | A1 | 9/2011 | Sun | |
| 2020/0308641 | A1* | 10/2020 | Davis | G01N 33/48721 |

FOREIGN PATENT DOCUMENTS

| | | | |
|---|---|---|---|
| JP | 2010524436 A | 7/2010 | |
| WO | 2010026488 A2 | 3/2010 | |
| WO | WO-2010109197 A2 * | 9/2010 | ........... C12Q 1/6869 |
| WO | 2010117470 A2 | 10/2010 | |
| WO | 2011040996 A1 | 4/2011 | |
| WO | 2011143340 | 11/2011 | |

* cited by examiner

NANOPORE BASED MOLECULAR DETECTION AND SEQUENCING

CROSS-REFERENCE

This application is a continuation application of U.S. patent application Ser. No. 15/703,909, filed Sep. 13, 2017, which is a continuation application of U.S. patent application Ser. No. 13/745,688, filed Jan. 18, 2013, now abandoned, which claims the benefit of U.S. Provisional Application No. 61/589,196, filed Jan. 20, 2012, U.S. Provisional Application No. 61/589,719, filed Jan. 23, 2012, and U.S. Provisional Application No. 61/600,227, filed Feb. 17, 2012, each of which is incorporated herein by reference in its entirety.

SEQUENCE LISTING

This instant application contains a Sequence Listing which has been submitted in ASCII format via EFS-Web and is hereby incorporated by reference in its entirety. Said ASCII copy, created on Apr. 16, 2020, is named 04338_007US3_Sequence_Listing.txt and is 6 kilobytes in size.

BACKGROUND

Nucleic acid sequencing is a process that may be used to provide sequence information for a nucleic acid sample. Such sequence information may be helpful in diagnosing and/or treating a subject. For example, the nucleic acid sequence of a subject may be used to identify, diagnose, and potentially develop treatments for genetic diseases. As another example, research into pathogens may lead to treatment for contagious diseases.

There are methods available which may be used to sequence a nucleic acid. Such methods, however, are expensive and may not provide sequence information within a time period and at an accuracy that may be necessary to diagnose and/or treat a subject.

SUMMARY

Nanopores can be used to sequence polymers including nucleic acid molecules. Recognized herein is the need for improved methods for nucleic acid molecule identification and nucleic acid sequencing. In some instances, the polymer is passed through the nanopore and various subunits of the polymer (e.g., adenine (A), cytosine (C), guanine (G), thymine (T) and/or uracil (U) bases of the nucleic acid) may affect the current flowing through the nanopore. As described herein, the various subunits can be identified by measuring the current at a plurality of voltages applied across the nanopore and/or membrane. In some cases, the polymerization of tagged nucleotides releases and/or presents tag molecules to the nanopore that can be identified by measuring the electric current at a plurality of voltages applied across the nanopore and/or membrane. Also provided herein are methods for sequencing both the sense and anti-sense strand of a double stranded nucleic acid molecule with a nanopore and methods for using ribonucleic acid (RNA) speed bump molecules to slow the passage of a nucleic acid molecule through a nanopore.

An aspect of the present disclosure provides a method for identifying a molecule or portion thereof , the method comprising (a) providing a chip comprising at least one, nanopore in a membrane that is disposed adjacent or in proximity to an electrode, wherein the electrode is adapted to detect an electric current passing through the nanopore. Nexs, a molecule or portion thereof can be inserted into the nanopore. A voltage can then be applied across the nanopore and/or across the membrane, and the voltage can be varied. The electric current at a plurality of voltages can be measured to identify the molecule or portion thereof.

Another aspect of the present disclosure provides a method for sequencing a nucleic acid molecule or portion thereof, the method comprising providing a double stranded nucleic acid molecule comprising a sense strand and an anti-sense strand, and ligating a first nucleic acid segment on a first end of the double stranded nucleic acid molecule. The first nucleic acid segment links the sense strand with the anti-sense strand at the first end of the double stranded nucleic acid molecule. Next, the double stranded nucleic acid molecule can be dissociated to provide a single stranded nucleic acid molecule comprising a sense portion of the sense strand and an anti-sense portion of the anti-sense strand. The single stranded nucleic acid molecule can then be passed or directed through or in proximity to a nanopore in a membrane that is disposed adjacent or in proximity to an electrode. The electrode can be adapted to detect an electric current upon the single stranded nucleic molecule residing in, or passing through or in proximity to, the nanopore. Next, using the electrode, electric current (also "current" herein) measurements can be obtained while the single stranded nucleic acid molecule resides I the nanopore, or passes through or in proximity to the nanopore. The sequence of the double stranded nucleic acid can be determined from the electric current measurements.

Another aspect of the present disclosure provides a method for sequencing a nucleic acid molecule or portion thereof, the method comprising passing a single stranded nucleic acid molecule through or in proximity to a nanopore in a membrane that is disposed adjacent or in proximity to an electrode. The single stranded nucleic molecule comprises a sense strand coupled to an anti-sense strand through a nucleic acid segment ligated on an end portion of each of the sense strand and anti-sense strand. The electrode is adapted to detect an electric current upon the single stranded nucleic molecule passing through or in proximity to the nanopore. With the aid of the electrode, electric current measurements are obtained while passing the single stranded nucleic acid molecule through or in proximity to the nanopore. A sequence of the single stranded nucleic acid molecule can be determined from the electric current measurements.

Another aspect of the present disclosure provides a method for sequencing a nucleic acid molecule, comprising providing a chip comprising at least one nanopore in a membrane that is disposed adjacent or in proximity to an electrode. The electrode is adapted to detect the nucleic acid molecule or a portion thereof. Next, the nucleic acid molecule can be directed through or in proximity to the nanopore. Progression of the nucleic acid molecule through or in proximity to the nanopore is stopped or stalled with the aid of at least one ribonucleic acid (RNA) speed-bump molecule associated with the nucleic acid molecule. The nucleic acid molecule or a portion thereof can be sequenced as the nucleic acid molecule passes through or in proximity to the nanopore.

Another aspect of the present disclosure provides a method for obtaining sequence information of a nucleic acid molecule, the method comprising forming a duplex segment comprising at least one ribonucleic acid (RNA) speed bump molecule associated with the nucleic acid molecule, and flowing the nucleic acid molecule through, adjacent to, or in proximity to a nanopore in a membrane. The membrane is disposed adjacent to or in proximity to an electrode which may be coupled to, or be a part of, a sensing circuit. Upon flowing the nucleic molecule through, adjacent to, or in proximity to the nanopore, the duplex segment is directed towards or across the nanopore. Next, electrical signals from the electrode are obtained upon the flow of the nucleic acid molecule through, adjacent to, or in proximity to the nanopore. The electrical signals are associated with the interaction of one or more bases of the nucleic acid molecule and at least a portion of the nanopore. The flow of the nucleic acid molecule can be reduced, in some cases stalled, with the aid of the duplex segment.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

In FIG. 1A, the nanopore is disposed upon the electrode, in FIG. 1B, the nanopore is inserted in a membrane over a well, and in FIG. 1C, the nanopore is disposed over a protruding electrode;

FIG. 2A shows the detection of a molecule, FIG. 2B shows the detection of portions of a polymer molecule, FIG. 2C shows the detection of tag molecules for nucleic acid sequencing, and FIG. 2D shows the detection of the tag while the nucleotide is being incorporated;

DETAILED DESCRIPTION

Figure 1A:
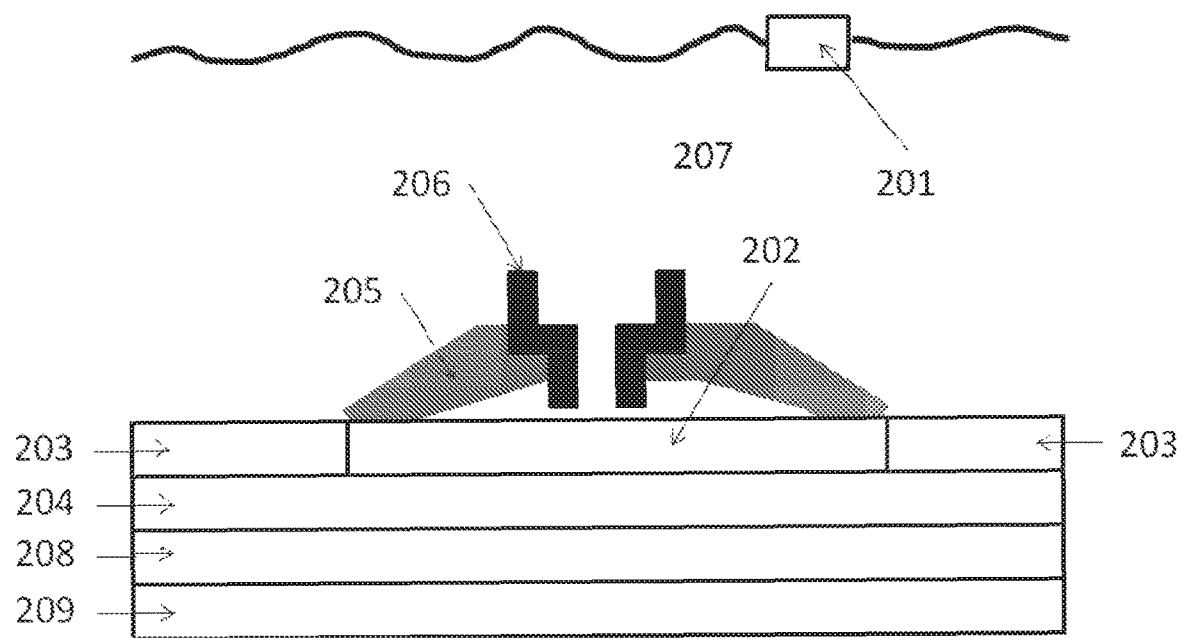
FIGS. 1A, 1B and 1C show examples of nanopore detectors.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "nanopore," as used herein, generally refers to a pore, channel or passage formed or otherwise provided in a membrane. A membrane may be an organic membrane, such as a lipid bilayer, or a synthetic membrane, such as a membrane formed of a polymeric material. The membrane may be a polymeric material. The nanopore may be disposed adjacent or in proximity to a sensing circuit or an electrode coupled to a sensing circuit, such as, for example, a complementary metal-oxide semiconductor (CMOS) or field effect transistor (FET) circuit. In some examples, a nanopore has a characteristic width or diameter on the order of 0.1 nanometers (nm) to about 1000 nm. Some nanopores are proteins. Alpha hemolysin is an example of a protein nanopore.

The term "polymerase," as used herein, generally refers to any enzyme or other molecular catalyst that is capable of catalyzing a polymerization reaction. Examples of polymerases include, without limitation, a nucleic acid polymerase or a ligase. A polymerase can be a polymerization enzyme.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. A nucleotide can include A, C, G. Tor U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof ) or a pyrimidine C, T or U, or variant thereof ). A subunit can enable individual nucleic acid bases or groups of bases (e.g., AA, TA, AT, GC, CG, CT, TC, GT, TG, AC, CA, or uracil-counterparts thereof ) to be resolved. In some examples, a nucleic acid is deoxyribonucleic acid (DNA) or ribonucleic acid (RNA), or derivatives thereof. A nucleic acid may be single-stranded or double stranded.

The term "polynucleotide" or "oligonucleotide," as used herein, generally refers to a polymer or oligomer comprising one or more nucleotides. A polynucleotide or oligonucleotide may comprise a DNA polynucleotide or oligonucleotide, a RNA polynucleotide or oligonucleotide, or one or more sections of DNA polynucleotide or oligonucleotide and/or RNA polynucleotide or oligonucleotide.

As generally used herein, a "nucleotide" or "base" can be a primary nucleotide or a nucleotide analog. A primary nucleotide is deoxyadenosine mono-phosphate (dAMP), deoxycytidine mono-phosphate (dCMP), deoxyguanosine mono-phosphate (dGMP), deoxythymidine mono-phosphate (dTMP), adenosine mono-phosphate (AMP), cytidine mono-phosphate (CMP), guanosine mono-phosphate (GMP) or uridine mono-phosphate (UMP). A nucleotide analog is an analog or mimic of a primary nucleotide having modification on the primary nucleobase (A, C, G, T and U), the deoxyribose/ribose structure, the phosphate group of the primary nucleotide, or any combination thereof. For example, a nucleotide analog can have a modified base, either naturally existing or man-made. Examples of modified bases include, without limitation, methylated nucleobases, modified purine bases (e.g., hypoxanthine, xanthine, 7-methylguanine, isodG), modified pyrimidine bases (e.g., 5,6-dihydrouracil and 5-methylcytosine, isodC), universal bases (e.g., 3-nitropyrrole and 5-nitroindole), non-binding base mimics (e.g., 4-methylbezimidazole and 2,4-difluorotoluene or benzene), and no base (ohmic nucleotide where the nucleotide analog does not have a base). Examples of nucleotide analogs having modified deoxyribose (e.g. dideoxynucleosides such as dideoxyguanosine, dideoxyadenosine, dideoxythyidine, and dideoxycytidine) and/or phosphate structure (together referred to as the backbone structure) includes, without limitation, glycol nucleotides, morpholinos, and locked nucleotides.

The term "test polymer," as used herein, generally refers to a polymer molecule that passes through or adjacent to a nanopore for detection purposes. The test polymer may comprise multiple building blocks that have similar chemical structures. Examples of test polymers include, without limitation, test polynucleotides, test peptides/proteins, and test carbohydrates. A test polynucleotide can be a single-stranded test polynucleotide (i.e., ss test polynucleotide) or a double-stranded test polynucleotide (i.e., ds test polynucleotide). Examples of building blocks include, without limitation, nucleotides, amino acids, and monosaccharides.

The term "sample polynucleotide," as used herein, generally refers to a nucleic acid molecule which can comprise a polynucleotide of interest, such as, for example, a single-stranded ("ss") sample polynucleotide (ss sample polynucleotide) or a double-stranded ("ds") sample polynucleotide (i.e., ds sample polynucleotide, such as, e.g., ds sample DNA, ds sample RNA, and ds sample DNA-RNA hybrid). A sample polynucleotide can be a natural polynucleotide obtained from a biological sample or a synthetic polynucleotide. The synthetic polynucleotide may be a polynucleotide obtained by modification of a natural polynucleotide, such as pre-processed polynucleotide intended for use in polynucleotide identification and/or sequencing. Examples of such pre-processings include, without limitation, enrichment of the sample polynucleotide for desired fragments, paired-end processing, mated pair read processing, epigenetic pre-processing including bisulfide treatment, focused fragment analysis via PCR, PCR fragment sequencing, and short polynucleotide fragment analysis.

The term "test polynucleotide," as used herein, generally refers to a polynucleotide molecule that passes through or adjacent to a nanopore for detection purposes. A test polynucleotide can be a single-stranded test polynucleotide (i.e., ss test polynucleotide) and a double-stranded test polynucleotide (i.e., ds test polynucleotide, such as, e.g., ds test DNA, ds test RNA, and ds test DNA-RNA hybrid). A ss test polynucleotide, as used herein, comprises a section of ss polynucleotide that is to be bound by a speed bump in a method described herein. A ss test polynucleotide may further comprise a sample polynucleotide and other functional moieties (e.g., pre-bulky structure, identifiers and isolation tags).

The term "pre-bulky structure", as used herein, generally refers to a molecular structure in a polynucleotide molecule which can form a bulky structure under certain conditions (e.g., at certain temperature, presence/absence of certain compound(s)). Examples of pre-bulky structures include oligonucleotide structures. A pre-bulky structure can be as polynucleotide or a ds polynucleotide.

The term "bulky structure", as used herein, generally refers to a structure (e.g., nucleotide) formed from a pre-bulky structure in as test polynucleotide molecule. The bulky structure can slow or stall the test polynucleotide molecule in a nanopore at a working condition until the working condition is changed to another condition wherein the bulky structure is converted to the pre-bulky structure or other structures that may stall the test polynucleotide molecule. Examples of bulky structures include, without limitation, 2-D and 3-D structures such as polynucleotide duplex structures (RNA duplex, DNA duplex or RNA-DNA hybrid), polynucleotide hairpin structures, multi-hairpin structures and multi-arm structures. In another embodiment the pre-bulky structure forms a bulky structure via interaction with a ligand specific to the pre-bulky structure. Examples of such pre-bulky structure/ligand pair include, without limitation, biotin/streptavidin, antigen/antibody, and carbohydrate/antibody.

In an embodiment, the bulky structure is formed from an oligonucleotide pre-bulky structure, e.g., an oligonucleotide structure formed from a pre-bulky structure in as test polynucleotide molecule. Examples of polynucleotide or oligonucleotide bulky structures include, without limitation, hairpin nucleic acid strands, hybridized antisense nucleic acid strands, multiple arms and three dimensional DNA or RNA molecules that are self-hybridized. In another embodiment, the bulky structure is formed via interactions of a pre-bulky structure/ligand pair as described herein.

The term "duplex," as used herein, generally refers to a duplex structure, section, region or segment. A duplex can include an RNA duplex, DNA duplex or a DNA-RNA duplex structure, section, region or segment.

The term "speed bump," as used herein, generally refers to a molecule, such as an oligonucleotide, that forms a complex with a binding segment of a test polynucleotide molecule. In an example, when a test polynucleotide molecule travels through or adjacent to a nanopore under an applied electric potential, the complex formed between a speed bump and the binding segment slows or stalls the test polynucleotide molecule in or adjacent to the nanopore for a dwelling time long enough for the nanopore detector to obtain a signal from the test polynucleotide molecule, which signal can provide structure or sequence information for the test polynucleotide molecule. After the dwelling time, the complex dissociates and the test polynucleotide molecule moves forward through the nanopore.

The term "known speed bump," as used herein, generally refers to a speed bump that specifically binds to a known sequence in a ss test polynucleotide. Because the binding segment on the ss test polynucleotide (the known sequence) is known, the speed bump structure can also be known (e.g., complementary to the known sequence on the ss test polynucleotide).

The term "random speed bump pool," as used herein, generally refers to a collection of speed bumps that can bind to all or substantially all sections of a test polynucleotide molecule or a fragment thereof. An example of random speed bump pool comprises oligonucleotides having universal nucleobases which base-pair with all primary nucleobases T, C, G and U). Another example of random speed bump pool comprises oligonucleotides of a given length having all possible combinations of primary nucleobases. Another example of random speed bump pool comprises oligonucleotides of a given length having every possible combination of primary nucleobases and universal nucleobases. Another example of random speed bump pool comprises speed bumps having universal nucleobases at designated positions and all combinations of primary nucleobases at the other positions. Another example of random speed bumps is a combination of ss speed bumps, which form duplex sections with ss test polynucleotide, and the duplex sections have about the same melting temperatures. These ss speed bumps may have the same or different lengths, and/or the same or different nucleotides.

The term "stopper," as used herein, generally refers to a structure that can form a stopper-test polynucleotide complex with the test polynucleotide and stop the flow of the stopper-test polynucleotide complex before the constriction area of the nanopore for the dwelling time. The stopper can be part of the test polynucleotide, or a separate structure (e.g., a speed bump described herein, and an antisense strand of the test polynucleotide formed in the presence of a nucleotide polymerase), or an enzyme that can bind to the test polynucleotide and optionally move the test polynucleotide through the nanopore.

The term "identifier," as used herein, generally refers to a known sequence or structure in a test polynucleotide that can be detected or identified by the method described herein. Examples of identifiers include, without limitation, direction identifiers, reference signal identifiers, sample source identifiers, and sample identifiers. The identifiers may comprise one or more nucleotides or structures that provide distinctive electrical signals that are identifiable. Examples of such nucleotides and structures include, without limitation, isodG, isodC, methylated nucleotides, locked nucleic acids, universal nucleotides, and abasic nucleotides. In some embodiments, an abasic nucleotide provides a stronger signal than a primary nucleotide. Thus, the electrical signal detected by a nanopore for a sequence comprising both abasic nucleotides and primary nucleotides may, provide a signal more intense than the electrical signal obtained from primary nucleotide only sequences. For example, a 4 to 5 base sequence comprising about 25% abasic nucleotides may provide a signal more than twice as strong as a 4 to 5 base sequence comprising only primary nucleotides. The more abasic nucleotides the sequence have, the stronger electrical signal the sequence. Thus, identifiers may provide electrical signals of a desired intensity (e.g., about twice, about 3, 4, 5, 6, 7, 8, 9, or about 10 times stronger than that of primary oligonucleotides having the same length) by changing the amount of abasic nucleotides in the identifier sequences.

Figure 17:
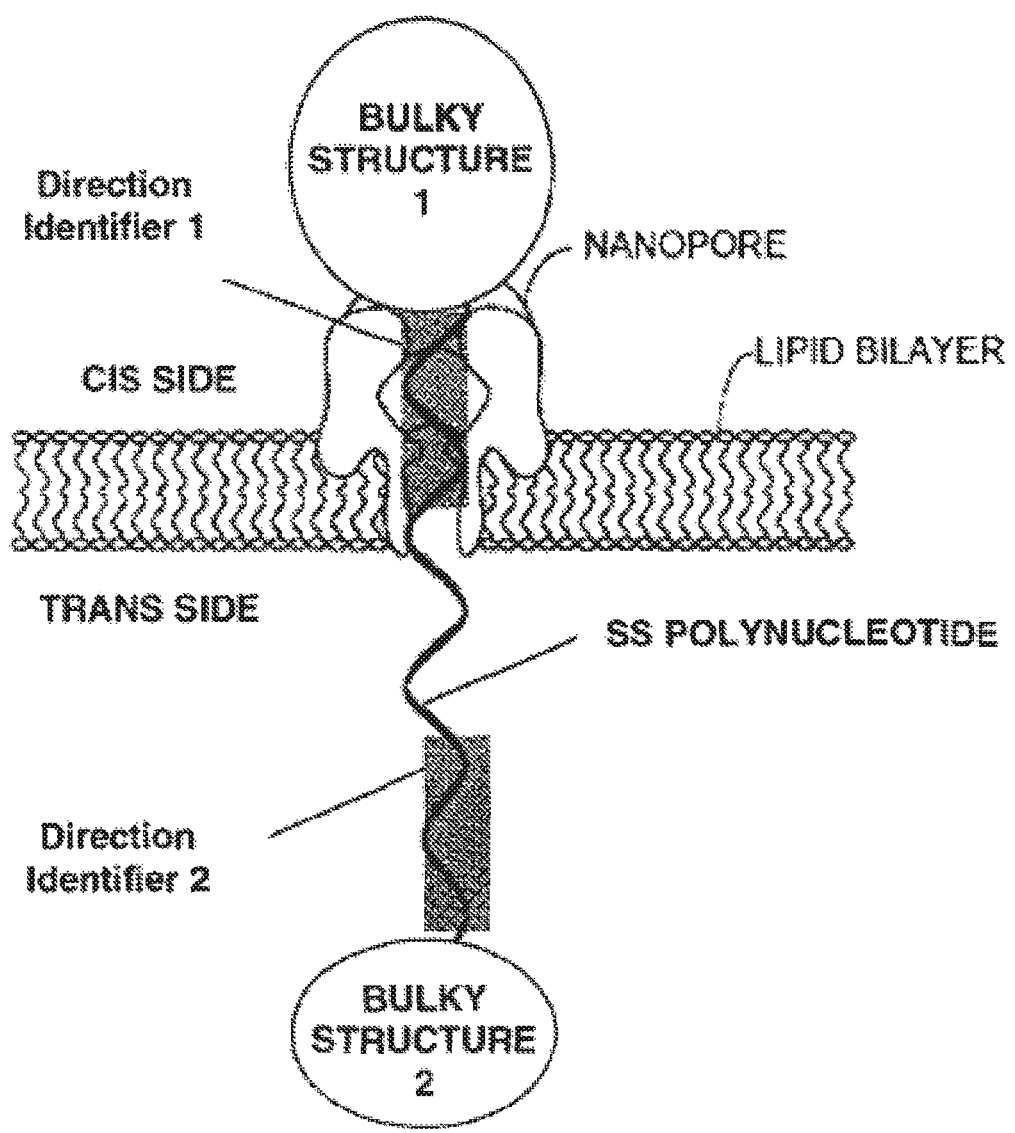
FIG. 17 illustrates detection of direction identifier in a ss test polynucleotide trapped in a nanopore bound by two bulky structures.

The term "direction identifier," as used herein, generally refers to a known sequence positioned at least 0, 1, 2, 3, 4, 5, 6, 7, 8, 9, 10, 11, 12, 13, 14, 16, 17, 18, 19, 20, or 50 bases from a bulky structure formed from a pre-bulky structure (the shaded section in the ss test polynucleotide molecule as depicted in FIG. 17). In some examples, when a bulky structure is formed, it can stop a ss test polynucleotide molecule from flowing through a nanopore within which the ss test polynucleotide molecule is incorporated. In an example, when the bulky structure is stalled, slowed or stopped inside or adjacent to the nanopore, a set of electrical signals may be obtained, which can provide sequence information of the sequence that is in front of the bulky structure and the first base pair of the bulky structure, in the flow direction of the ss test polynucleotide molecule. When the sequence is known, such electrical signals can, without limitation: (1) verify that the pre-bulky structure has properly formed into the bulky structure such that the bulky structure stops the ss test polynucleotide molecule from flowing through the nanopore; (2) indicate that the ss test polynucleotide molecule has reached one end of the single strand section of the ss test polynucleotide, and/or (3) serve as a reference or calibration read to base line other electrical signals obtained in the same nanopore. In some embodiments, the direction identifier comprises one or more nucleotides or structures that provide distinctive electrical signals that are readily identified. Examples of such nucleotides and structures include, without limitation, isodG, isodC and abasic nucleotides.

The term "reference signal identifier," as used herein, generally refers to a known sequence in a test polynucleotide, which when detected or identified by the methods described herein, can serve as a reference or calibration read to base line other electrical signals obtained in the same nanopore.

The term "sample source identifier," as used herein, generally refers to a known sequence in a test polynucleotide, which when detected or identified by the methods described herein, can be used to identify the source of the sample polynucleotide.

The term "sample identifier," as used herein, generally refers to a known sequence in a test polynucleotide, which when detected or identified by the methods described herein, can be used to identify the individual sample polynucleotide.

The term "linker identifier," as used herein, generally refers to a known sequence in a test polynucleotide, which when detected or identified by the methods described herein, can be used to indicate the transition between the sample polynucleotide section and the antisense polynucleotide section. In an example, when the linker identifier is detected or identified, the sample/antisense polynucleotide section has passed through the nanopore.

This disclosure provides devices, systems and methods for sequencing, such as, for example, nucleic acid (e.g., DNA, RNA), protein, or polymeric sequencing. Methods of the disclosure may be used to sequence nucleic acid molecules, such as DNA or RNA, or other polymeric molecules, such as proteins. In the case of nucleic acid sequencing, the nucleic acid base content of a nucleic acid molecule may be determined. In the case of protein sequencing, the amino acid sequence of a protein may be determined.

Nanopore Detection

Provided herein are systems and methods for identifying a molecule or portion thereof with a nanopore. A method for identifying a species, such as a molecule or portion thereof, with a nanopore can comprise providing a chip comprising at least one nanopore in a membrane that is disposed adjacent or in proximity to an electrode. The electrode can be adapted to detect a current passing through the nanopore. The method can further include inserting a molecule or portion thereof into the nanopore and varying a voltage applied across the nanopore and/or across the membrane. In some cases, the method includes measuring the current at a plurality of voltages to identify the molecule or portion thereof. In some embodiments, the current at a plurality of voltages comprises an electronic signature and further comprises comparing the electronic signature to a plurality of reference electronic signatures to identify the molecule or portion thereof.

The nanopore may be formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or of f of the chip or device, such as in an of f-chip configuration. The semiconductor can be any semiconductor, including, without limitation, Group IV (e.g., silicon) and Group III-V semiconductors (e.g., gallium arsenide).

FIG. 1 shows an examples of a nanopore detector (or sensor) having temperature control, as may be prepared according to methods described in U.S. Patent Application Publication No. 2011/0193570, which is entirely incorporated herein by reference. With reference to FIG. 1A, the nanopore detector comprises a top electrode 101 in contact with a conductive solution (e.g., salt solution) 107. A bottom conductive electrode 102 is near, adjacent, or in proximity to a nanopore 106, which is inserted in a membrane 105. In some instances, the bottom conductive electrode 102 is embedded in a semiconductor 103 in which is embedded electrical circuitry in a semiconductor substrate 104. A surface of the semiconductor 103 may be treated to be hydrophobic. A sample being detected goes through the pore in the nanopore 106. The semiconductor chip sensor is placed in package 208 and this, in turn, is in the vicinity of a temperature control element 109. The temperature control element 109 may be a thermoelectric heating and/or cooling device (e.g., Peltier device).

Multiple nanopore detectors may form a nanopore army. A nanopore array can include one or more nanopore detectors. In some cases, a nanopore array includes at least 1, 2, 3, 4, 5, 6, 7, 8, 9, 10, 100, 1000, 10000, or 100,000 nanopore detectors. An individual nanopore detector can include one or more nanopores adjacent to a sensing electrode (e.g., bottom conductive electrode 102). In some cases, an individual nanopore detector includes at least 1, 2, 3, 4, 5, 6, 7, 8, 9, 10, or 100 nanopores adjacent to a sensing electrode.

Figure 1B:
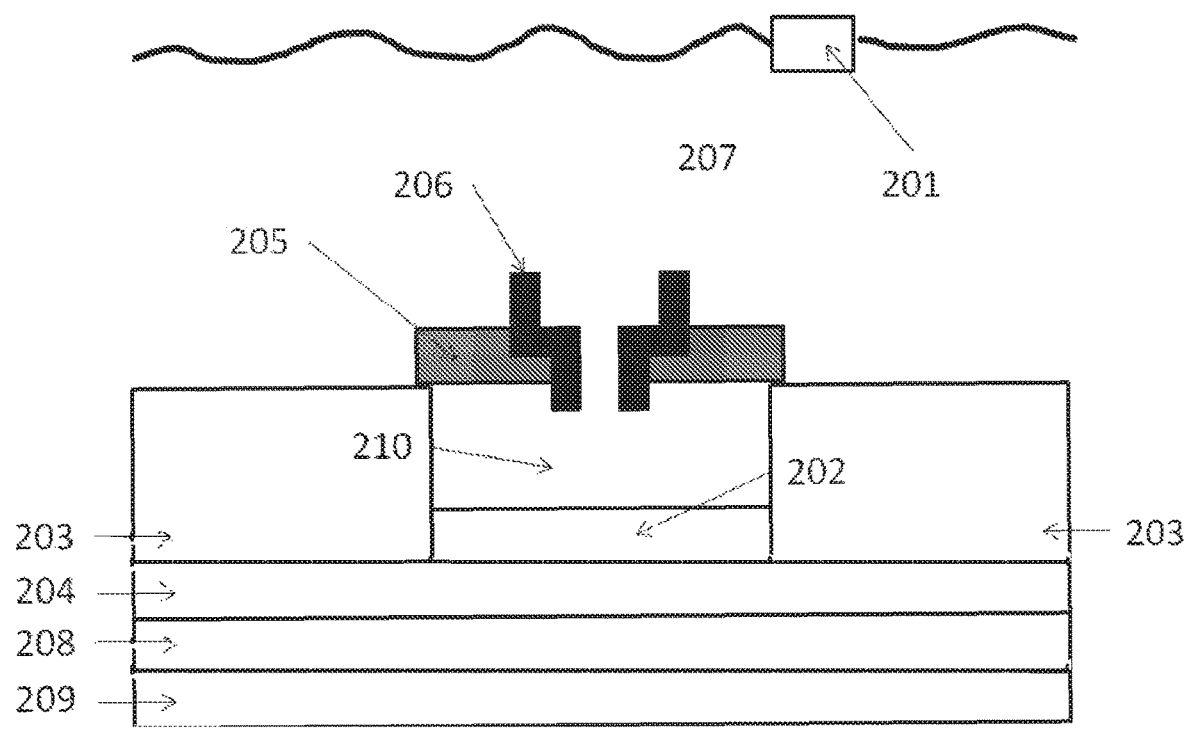
Figure 1C:
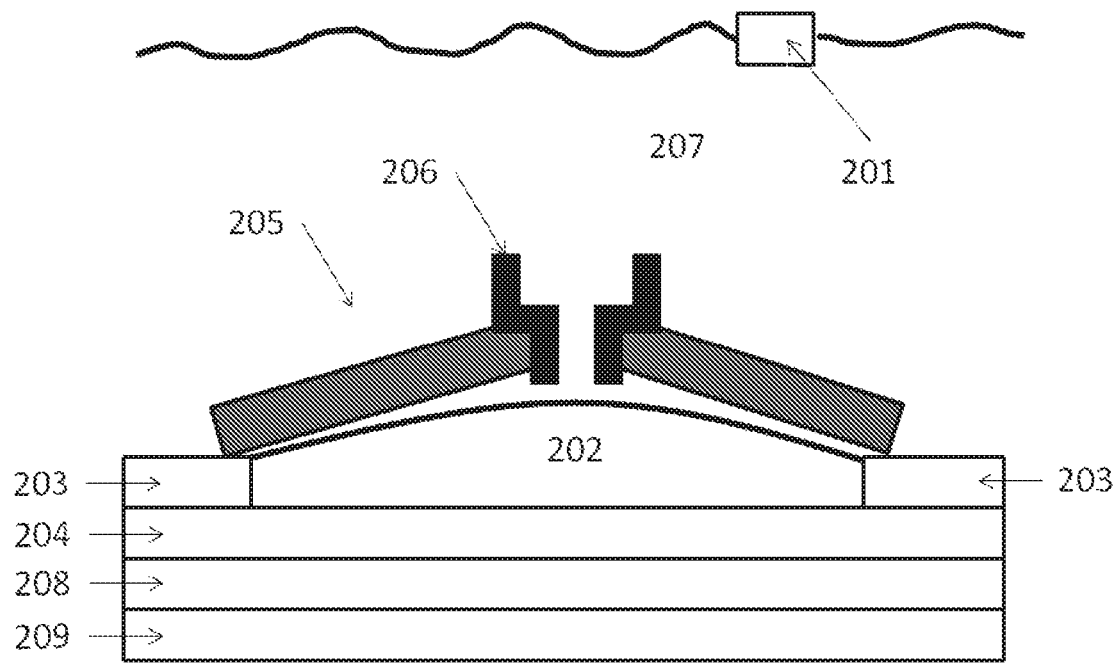

With reference to FIG. 1B, where like numerals represent like elements, the membrane 105 can be disposed over a well 110, where the sensor 102 forms part of the surface of the well. FIG. 1C shows an example in which the electrode 102 protrudes from the treated semiconductor surface 103.

In some examples, the membrane 105 forms on the bottom conductive electrode 102 and not on the semiconductor 103. The membrane 105 in such a case may form coupling interactions with the bottom conductive electrode 102. In some cases, however, the membrane 105 forms on the bottom conductive electrode 102 and the semiconductor 103. As an alternative, the membrane 105 can form on the semiconductor 103 and not on the bottom conductive electrode 102, but may extend over the bottom conductive electrode 102.

Many different types of molecules or portions thereof can be detected by the methods and/or devices described herein. FIG. 2 shows some examples of molecules that can be detected and methods for sequencing polymers including nucleic acids. In some cases, the molecule 201 passes through the nanopore 202 from the cis side 203 (away from the electrode) to the trans side 204 (toward to the electrode) of the membrane 205.

Figure 2A:
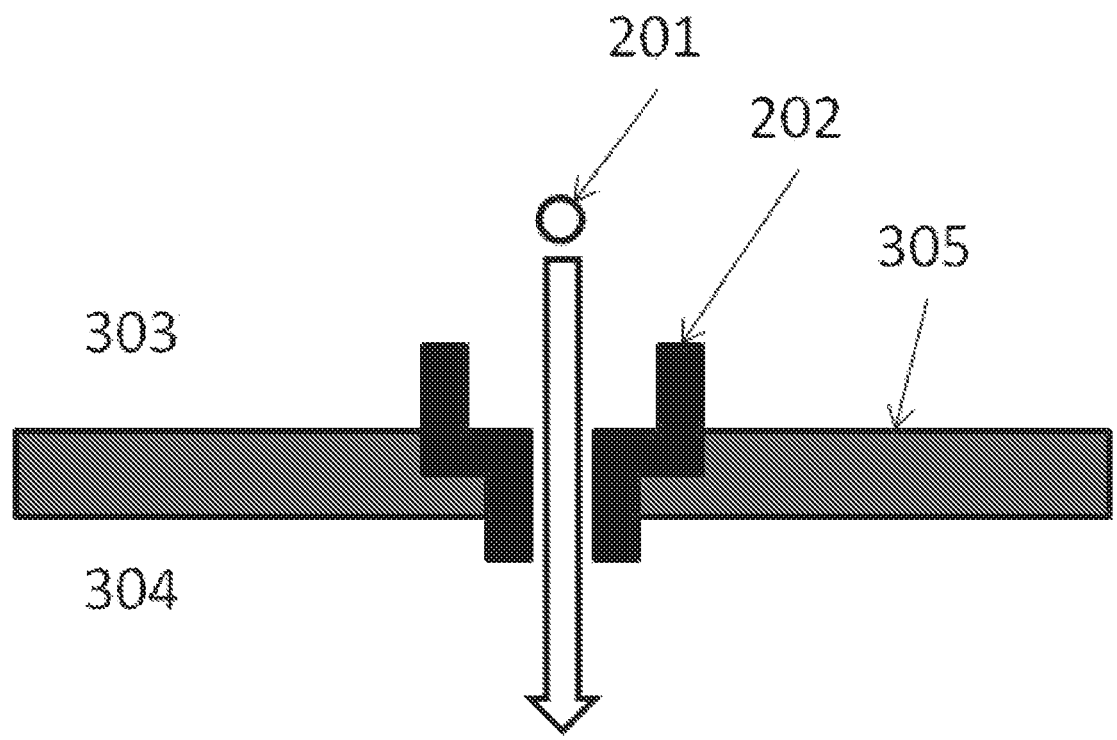
FIGS. 2A, 2B, 2C and 2D show examples of molecules that can be detected with nanopores.
Figure 2B:
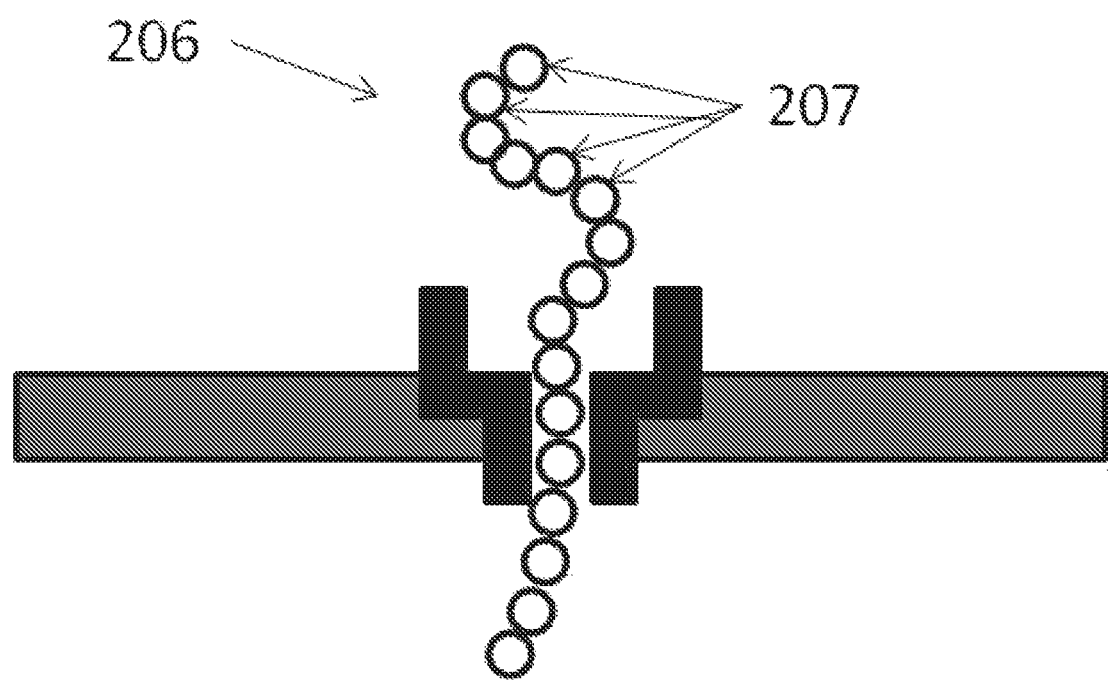

As seen in FIG. 2B, the molecule can be a polymer molecule 206 and portions of the polymer molecule 207 can be identified as the polymer molecule passes through the nanopore. The polymer molecule can be a biological molecule such as a nucleic acid or a protein. In some embodiments, the polymer molecule is a nucleic acid and the portions of the polymer molecule are nucleic acids or groups of nucleic acids (e.g., 2, 3, 4, 5, 6, 7, or 8 nucleic acids). In some embodiments, the poly, in er molecule is a polypeptide and the portions of the polypeptide are amino acids or groups of nucleic acids (e.g., 2, 3, 4, 5, 6, 7, or 8 amino acids).

In some cases, as a nucleic acid or tag flows through or adjacent to the nanopore, the sensing circuit detects an electrical signal associated with the nucleic acid or tag. The nucleic acid may be a subunit of a larger strand. The tag may be a byproduct of a nucleotide incorporation event or other interaction between a tagged nucleic acid and the nanopore or a species adjacent to the nanopore, such as an enzyme that cleaves a tag from a nucleic acid. The tag may remain attached to the nucleotide. A detected signal may be collected and stored in a memory location, and later used to construct a sequence of the nucleic acid. The collected signal may be processed to account for any abnormalities in the detected signal, such as errors.

Figure 2C:
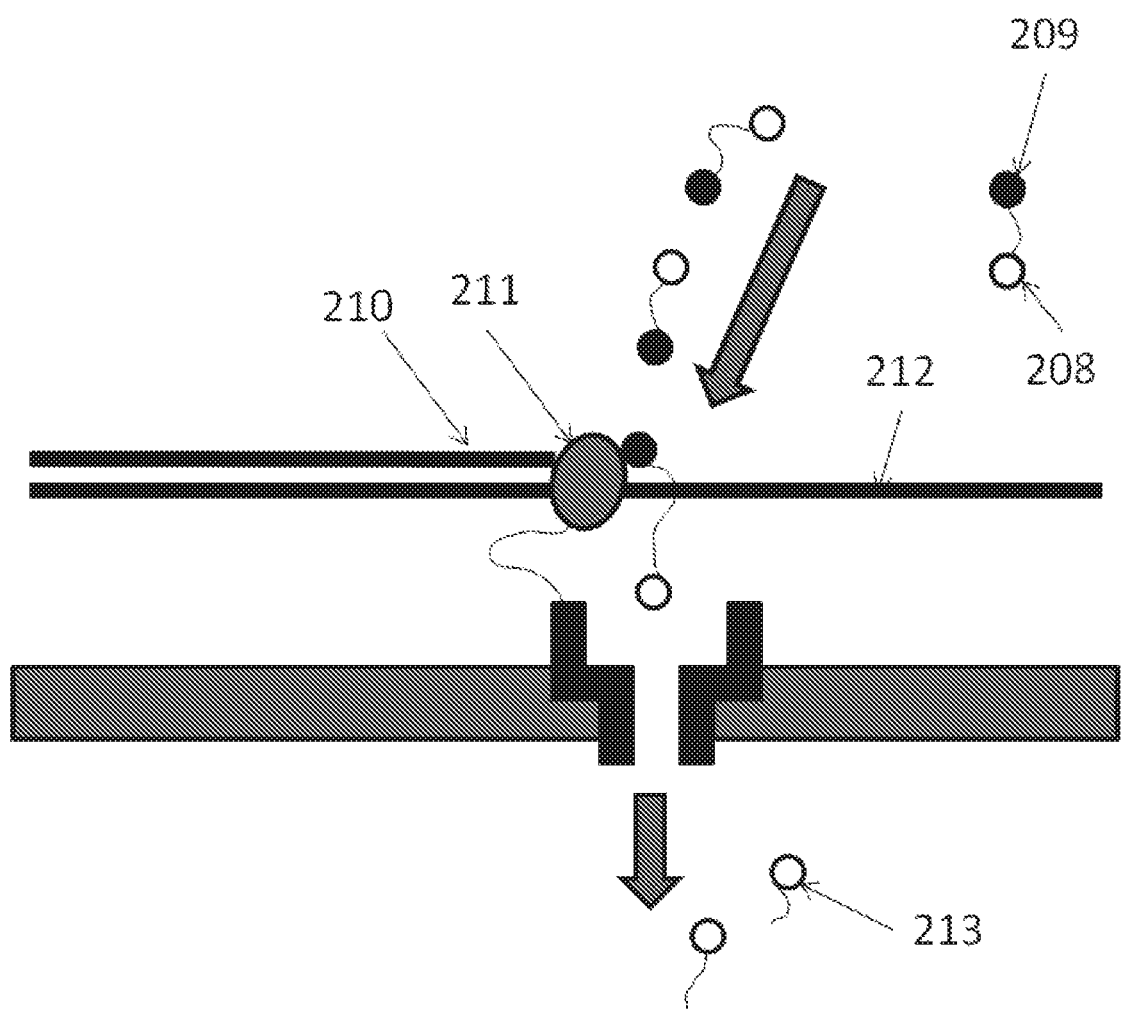
Figure 2D:
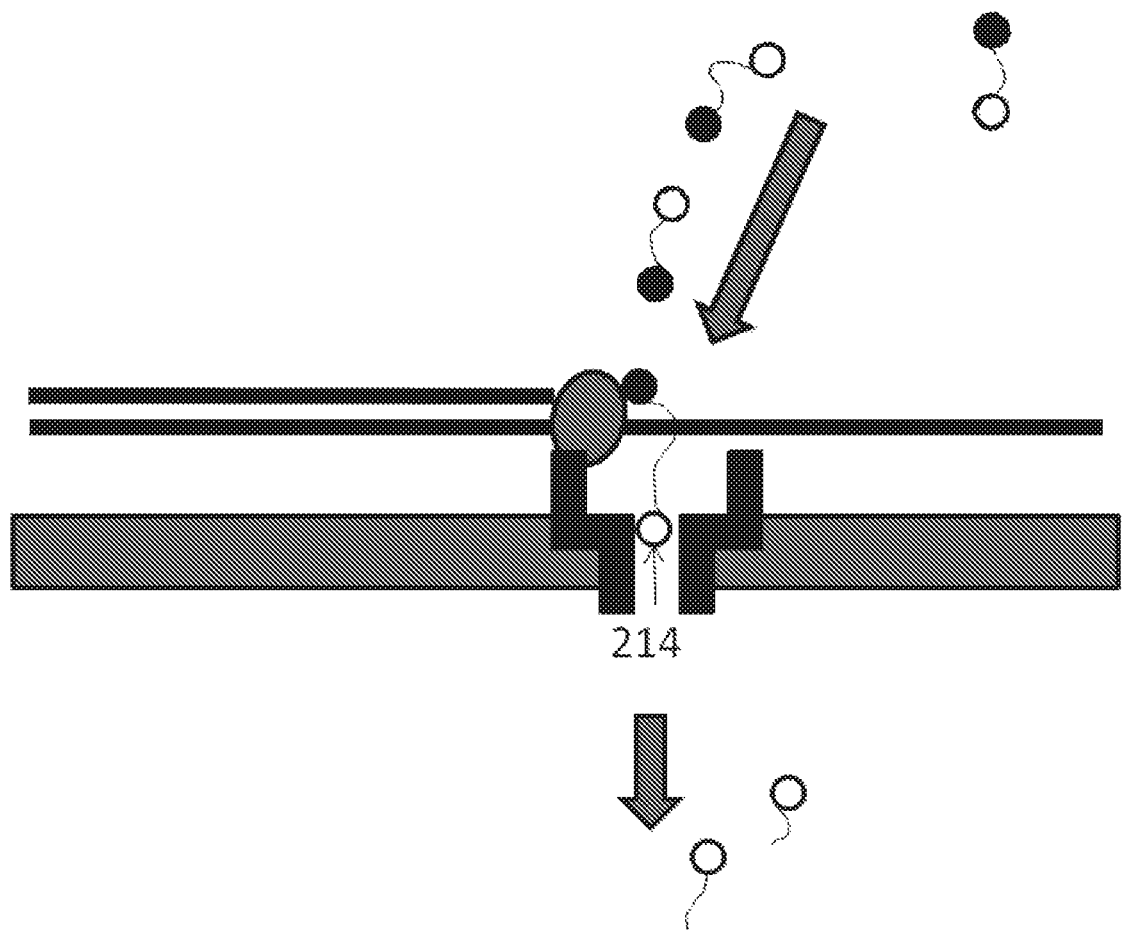

As seen in FIG. 2C, in some embodiments, the molecule 208 (e.g., a "tag molecule") is bound to a nucleotide 209. The molecule can be identified while the nucleotide is being incorporated into a growing nucleic acid chain 210 (e.g., by a polymerase 211). The nucleotide can be incorporated according to base pair matching with a template nucleic acid 212. If different tags are bound to each of the different nucleotides (e.g., A, C, T and G), the sequence of the template nucleic acid can be determined by detecting the tag molecules with the nanopore (e.g., without the template nucleic acid passing through the nanopore). In some embodiments, the molecule is released 213 from the nucleotide upon incorporation of the nucleotide into a growing nucleic acid chain. As shown in FIG. 2D, the molecule can be detected while the nucleotide is being incorporated into the growing strand and/or before being released from the nucleotide 214.

Device Setup

Figure 3:
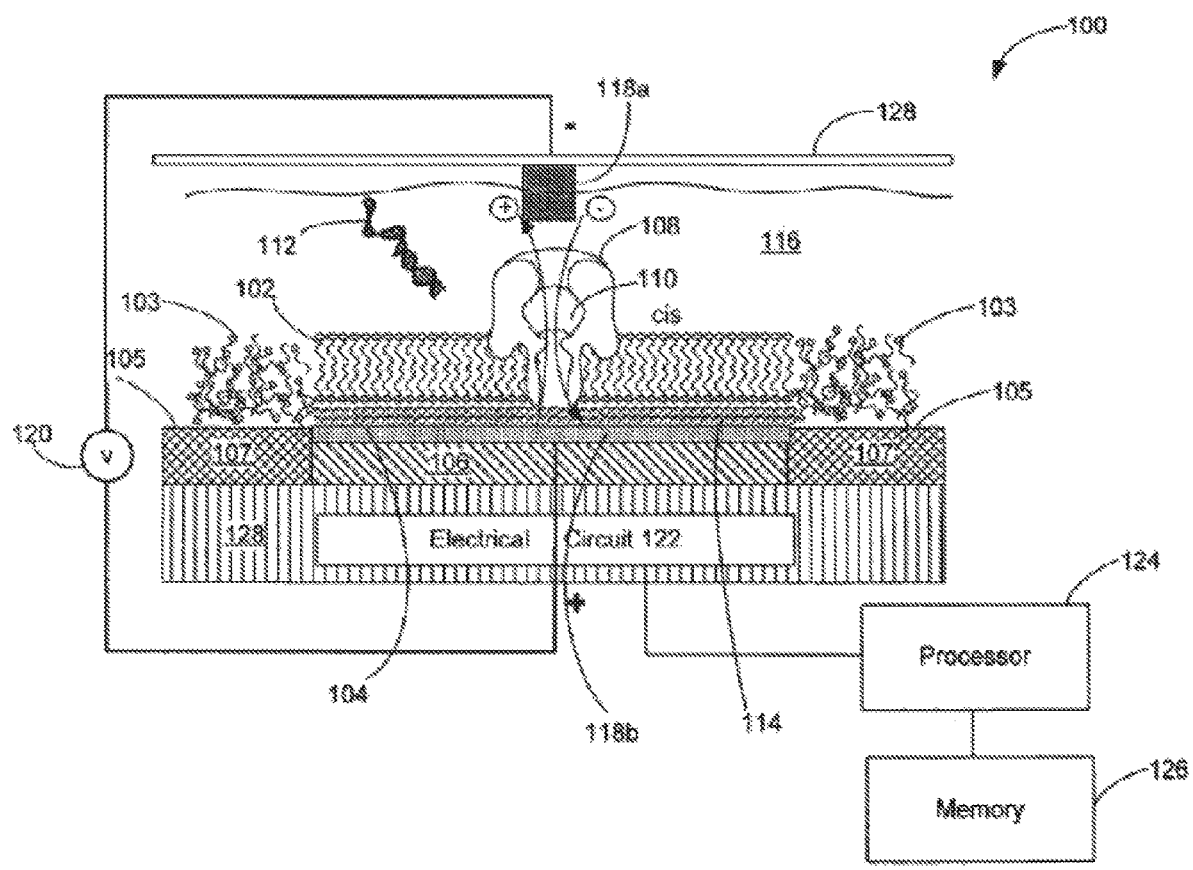
FIG. 3 shows an example of a chip set-up comprising a nanopore and not a well.

FIG. 3 schematically illustrates a nanopore device 100 (or sensor) that may be used to detect a molecule(and/or sequence a nucleic acid) as described herein. The nanopore containing lipid bilayer may be characterized by a resistance and capacitance. The nanopore device 100 includes a lipid bilayer 102 formed on a lipid bilayer compatible surface 104 of a conductive solid substrate 106, where the lipid bilayer compatible surface 104 may be isolated by lipid bilayer incompatible surfaces 105 and the conductive solid substrate 106 may be electrically isolated by insulating materials 107, and where the lipid bilayer 102 may be surrounded by amorphous lipid 103 formed on the lipid bilayer incompatible surface 105. The lipid bilayer 102 may be embedded with a single nanopore structure 108 having a nanopore 110 large enough for passing of the molecules being detected and/or small ions (e.g., $Na^+$, $K^+$, c $a^{2+}$, er') between the two sides of the lipid bilayer 102. A layer of water molecules 114 may be adsorbed on the lipid bilayer compatible surface 104 and sandwiched between the lipid bilayer 102 and the lipid bilayer compatible surface 104. The aqueous film 114 adsorbed on the hydrophilic lipid bilayer compatible surface 104 may promote the ordering of lipid molecules and facilitate the formation of lipid bilayer on the lipid bilayer compatible surface 104. A sample chamber 116 containing a solution of the molecule to be detected (e.g., nucleic acid molecule optionally with tagged nucleotides or other components as needed) 112 may be provided over the lipid bilayer 102. The solution may be an aqueous solution containing electrolytes and buffered to an optimum ion concentration and maintained at an optimum pH to keep the nanopore 110 open. The device includes a pair of electrodes 118 (including a negative node 118a and a positive node 118b) coupled to a variable voltage source 120 for providing electrical stimulus (e.g., voltage bias) across the lipid bilayer and for sensing electrical characteristics of the lipid bilayer (e.g., resistance, capacitance, and ionic current flow). The surface of the positive electrode 118b is or forms apart of the lipid bilayer compatible surface 104. The conductive solid substrate 106 may be coupled to or forms a part of one of the electrodes 118. The device 100 may also include an electrical circuit 122 for controlling electrical stimulation and for processing the signal detected. In some embodiments, the (e.g., variable) voltage source 120 is included as a part of the electrical circuit 122. The electrical circuitry 122 may include amplifier, integrator, noise filter, feedback control logic, and/or various other components. The electrical circuitry 122 may be integrated electrical circuitry integrated within a silicon substrate 128 and may be further coupled to a computer processor 124 coupled to a memory 126.

The lipid bilayer compatible surface 104 may be formed from various materials that are suitable for ion transduction and gas formation to facilitate lipid bilayer formation. In some embodiments, conductive or semi-conductive hydrophilic materials may be used because they may allow better detection of a change in the lipid bilayer electrical characteristics. Example materials include Ag—AgCl, Au, Pt, or doped silicon or other semiconductor materials. In some cases, the electrode is not a sacrificial electrode.

The lipid bilayer incompatible surface 105 may be formed from various materials that are not suitable for lipid bilayer formation and they are typically hydrophobic. In some embodiments, non-conductive hydrophobic materials are preferred, since it electrically insulates the lipid bilayer regions in addition to separate the lipid bilayer regions from each other. Example lipid bilayer incompatible materials include for example silicon nitride (e.g., $Si_3N_4$) and Teflon, silicon oxide (e.g., SiO2) silanized with hydrophobic molecules.

In an example, the nanopore device 100 of FIG. 3 is a alpha hemolysin (aHL) nanopore device having a single alpha hemolysin (aHL) protein 108 embedded in a diphytanoylphosphatidylcholine (DPhPC) lipid bilayer 102 formed over a lipid bilayer compatible silver (Ag) surface 104 coated on an aluminum material 106. The lipid bilayer compatible Ag surface 104 is isolated by lipid bilayer incompatible silicon nitride surfaces 105, and the aluminum material 106 is electrically insulated by silicon nitride materials 107. The aluminum 106 is coupled to electrical circuitry 122 that is integrated in a silicon substrate 128. A silver-silver chloride electrode placed on-chip or extending down from a cover plate 128 contacts an aqueous solution containing (e.g., nucleic acid) molecules.

The aHL nanopore is an assembly of seven individual peptides. The entrance or vestibule of the aHL nanopore is approximately 26 Angstroms in diameter, which is wide enough to accommodate a portion of a dsDNA molecule. From the vestible, the aHL nanopore first widens and then narrows to a barrel having a diameter of approximately 15 Angstroms, which is wide enough to allow a single ssDNA molecule (or smaller tag molecules) to pass through but not wide enough to allow a dsDNA molecule (or larger tag molecules) to pass through.

In addition to DPhPC, the lipid bilayer of the nanopore device may be assembled from various other suitable amphiphilic materials, selected based on various considerations, such as the type of nanopore used, the type of molecule being characterized, and various physical, chemical and/or electrical characteristics of the lipid bilayer formed, such as stability and permeability, resistance, and capacitance of the lipid bilayer formed. Example amphiphilic materials include various phospholipids such as palmitoyl-oleoyl-phosphatidyl-choline (POPC) and dioleoyl-phosphatidyl-methylester (DOPME), diphytanoylphosphatidylcholine (DPhPC) dipalmitoylphosphatidylcholine (DPPC), phosphatidylcholine, phosphatidylethanolamine, phosphatidylserine, phosphatidic acid, phosphatidylinositol, phosphatidylglycerol, and sphingomyelin.

In addition to the aHL nanopore shown above, the nanopore may be of various other types of nanopores. Examples include y-homolysin, leukocidin, melittin, mycobacterium smegmatis poria A (MspA) and various other naturally occurring, modified natural, and synthetic nanopores. A suitable nanopore may be selected based on various characteristics of the analyte molecule such as the size of the analyte molecule in relation to the pore size of the nanopore. For example, the aHL nanopore that has a restrictive pore size of approximately 15 Angstroms.

Current Measurement

In some cases, current may be measured at different applied voltages. In order to accomplish this, a desired potential may be applied to the electrode, and the applied potential may be subsequently maintained throughout the measurement. In an implementation, an opamp integrator topology may be used for this purpose as described herein. The integrator maintains the voltage potential at the electrode by means of capacitive feedback. The integrator circuit may provide outstanding linearity, cell-to-cell matching, and offset characteristics. The opamp integrator typically requires a large size in order to achieve the required performance. A more compact integrator topology is described herein.

In some cases, a voltage potential "Vliquid" may be applied to the chamber which provides a common electrical potential (e.g., 350 mV) for all of the cells on the chip. The integrator circuit may initialize the electrode (which is electrically the top plate of the integrating capacitor) to a potential greater than the common liquid potential. For example, biasing at 450 mV may give a positive 100 mV potential between electrode and liquid. This positive voltage potential may cause a current to flow from the electrode to the liquid chamber contact. In this instance, the carriers are: (a) K+ ions which flow through the pore from the electrode (trans) side of the bi-layer to the liquid reservoir (cis) side of the hi-layer and (b) chlorine (Cl−) ions on the trans side which reacts with the silver electrode according to the following electro-chemical reaction: Ag+Cl−AgCl+e−.

In some cases, K+ flows out of the enclosed cell (from trans to cis side of bi-layer) while Cl− is converted to silver chloride. The electrode side of the bilayer may become desalinated as a result of the current flow. In some cases, a silver/silver-chloride liquid spongy material or matrix may serve as a reservoir to supply Cl− ions in the reverse reaction which occur at the electrical chamber contact to complete the circuit.

In some cases, electrons ultimately flow onto the top side of the integrating capacitor which creates the electrical current that is measured. The electrochemical reaction converts silver to silver chloride and current will continue to flow only as long as there is available silver to be converted. The limited supply of silver leads to a current dependent electrode life in some cases. In some embodiments, electrode materials that are not depleted (e.g., platinum) are used.

Electrode Charging Methodologies

The ability to re-charge the electrode during the detection cycle can be advantageous when using sacrificial electrodes or electrodes that change molecular character in the current-carrying reactions (e.g., electrodes comprising silver), or electrodes that change molecular character in current-carrying reactions. An electrode may deplete during a detection cycle, though in some cases the electrode may not deplete during the detection cycle. The re-charge can prevent the electrode from reaching a given depletion limit, such as becoming fully depleted, which can be a problem when the electrodes are small (e.g., when the electrodes are small enough to provide an array of electrodes having at least 500 electrodes per square millimeter). Electrode lifetime in some cases scales and is at least partly dependent on the width of the electrode.

In some instances, the need to maintain a voltage difference of conserved polarity across the nanopore during detection for long periods of time (e.g., when sequencing a nucleic acid by passing the nucleic acid through the nanopore) depletes the electrodes and can limit the duration of detection and/or size of the electrodes. The devices and methods described herein allow for longer (e.g., infinite) detection times and/or electrodes that can be scaled down to an arbitrarily small size (e.g., as limited by considerations other than electrode depletion during detection). As described herein, the molecule (e.g., tag molecule) may be detected for only a portion of the time (e.g., that a tag is associated with the polymerase). Switching the polarity of the voltage across the nanopore in between detection periods allows for re-charging the electrodes. In some cases, the molecule or portion thereof is detected a plurality of times (e.g., 2, 3. 4, 5, 6, 7, 8, 9, 10, 20, 30, 40, 50, 100, 1000, 10,000, 100,000, 1,000,000 or more times in a 100 millisecond period).

In some instances, the polarity of the voltage across the nanopore is reversed periodically. The polarity of the voltage can be reversed after detection periods lasting any suitable amount of time (e.g., about 1 ms, about 5 ms, about 10 ms, about 15 ms, about 20 ms, about 25 ms, about 30 ms, about 40 ms, about 50 ms, about 60 ms, about 80 ms, about 100 ms, about 125 ms, about 150 ms, about 200 ms, and the like). The period of time and strength of the electrical field during periods of recharging the electrodes (i.e., when the polarity of the voltage is opposite that of the voltage for tag detection) is such that the electrode is restored to its state prior to detection (e.g., mass of electrode). The net voltage across the nanopore is zero in some instances (e.g., periods of positive voltage cancel periods of negative voltage over a suitably long time scale such as 1 second, 1 minute or 5 minutes). In some cases, the voltage applied to a nanopore is balanced such that there is net zero current detected by a sensing electrode adjacent to or in proximity to the nanopore.

In some examples, an alternating current (AC) waveform is applied to a nanopore in a membrane or an electrode adjacent to the membrane to draw a molecule through or in proximity to the nanopore and to release the molecule. The AC waveform can have a frequency on the order of at least 10 microseconds, 1 millisecond (ms), 5 ms, 10 ms, 20 ms, 100 ms, 200 ms, 300 ms, 400 ms, 500 ms. The waveform may aid in alternately and sequentially capturing molecules (e.g., the tag molecule) and releasing the molecule, or otherwise moving the molecule in multiple directions (e.g., opposing directions), which may increase the overall time period in which the molecule is associated with the nanopore. This balancing of charging and discharging can permit the generation of a longer signal from a nanopore electrode and/or a given molecule.

In some examples, an AC waveform is applied to repeatedly direct at least a portion of a molecule (e.g., tag associated with a tagged nucleotide (e.g., incorporated tagged nucleotide)) into a nanopore and direct at least a portion of the molecule out of the nanopore. The molecule (e.g., tag or nucleotide coupled to the tag) may be held by an enzyme (e.g., polymerase). This repetitive loading and expulsion of a single molecule held by the enzyme may advantageously provide more opportunities to detect the molecule. For instance, i f the molecule is held by the enzyme for 40 milliseconds (ms) and the AC waveform is applied high for 5 ms (e.g., to dierct the tag into the nanopore) and applied low for 5 ms (e.g., to direct the tag out of the nanopore), the nanopore may be used to read the molecule approximately 4 times. Multiple reads may enable correction for errors, such as errors associated with the molecule threading into and/or out of a nanopore.

Figure 29:
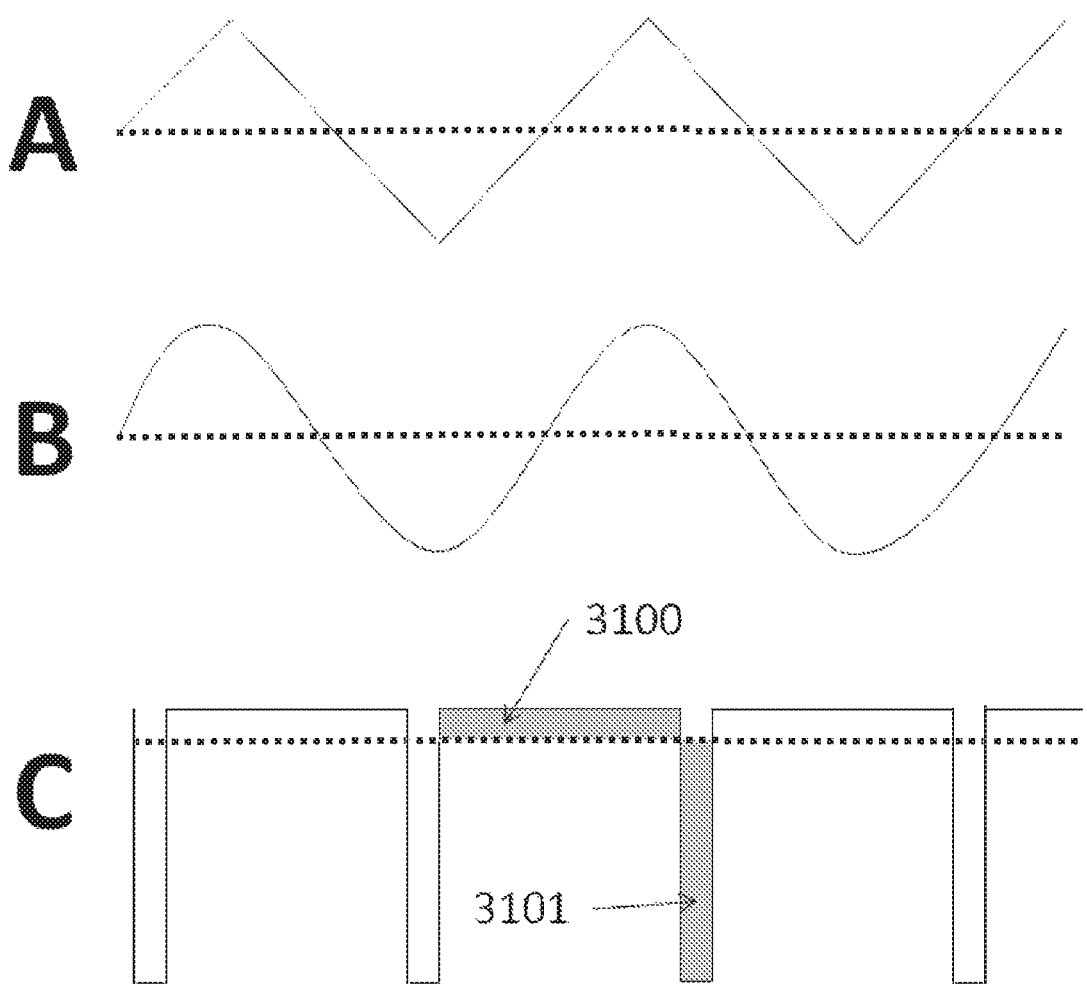
FIG. 29 shows examples of waveforms.

The waveform can have any suitable shape including either regular shapes (e.g., that repeat over a period of time) and irregular shapes (e.g., that do not repeat over any suitably long period of time such as 1 hour, 1 day or 1 week). FIG. 29 shows some suitable (regular) waveforms. Examples of waveforms include triangular waves, (panel A) sine waves (panel B), sawtooth waves, square waves, and the like.

The electrode can be depleted during detection of the molecules in some cases. Reversal of the polarity (i.e., positive to negative or negative to positive) of the voltage across the nanopore, such as upon the application of an alternating current (AC) waveform, can recharge the electrode. FIG. 29C shows a horizontal dashed line at zero potential difference across the nanopore with positive voltage extending upward in proportion to magnitude and negative voltage extending downward in proportion to magnitude. No matter the shape of the waveform, the combined area under the curve of a voltage versus time plot in the positive direction 3100 can equal the combined area under the curve in the negative direction 3101. In some instances, the electrode is neither charged nor depleted over a suitably long period of time (e.g., one hour, are clay or one week), for example when the positive 3100 and negative 3101 areas are equal. In some situations, upon the application of a positive potential across a nanopore, a first current is measured, and upon the application of a negative potential (e.g., of equal absolute magnitude to the positive potential) across the nanopore, a second current is measured. The first current may be equal to the second current, though in some cases the first current and the second current may be different. For example, the first current may be less than the second current.

In son cases, the nanopore detects tagged nucleotides for relatively long periods of time at a relatively low magnitude voltage (e.g., FIG. 29, indication 3100) and re-charges the electrode for relatively short periods of time at a relatively large magnitude voltage (e.g., FIG. 29, indication 3101). In some cases, the time period for detection is at least 2, at least 3, at least 4, at least 5, at least 6, at least 8 at least 10, at least 15, at least 20, or at least 50 times longer than the time period for electrode recharge.

In some instances, the waveform is altered in response to an input. In some cases, the input is the level of depletion. of the electrode. In some cases, the polarity and/or magnitude of the voltage is varied at least in part based on the depletion of the electrode and the waveform is irregular.

The ability to repeatedly detect and re-charge the electrodes over short time periods (e.g., over periods less than about 5 seconds, less than about 1 second, less than about 500 ms, less than about 100 ms, less than about 50 ms, less than about 10 ms, or less than about 1 ms) allows for the use of smaller electrodes relative to electrodes that may maintain a constant direct current (DC) potential and DC current and are used to sequence polynucleotides that are threaded through the nanopore. Smaller electrodes can allow for a high number of detection sites (e.g., comprising an electrode, a sensing circuit, a nanopore and a polymerase) on a surface.

The surface comprises any suitable density of discrete sites (e.g., a density suitable for sequencing a nucleic acid sample in a given amount of time or for a given cost). In an embodiment, the surface has a density of discrete sites greater than or equal to about 500 sites per 1 $mm^2$. In some embodiments, the surface has a density of discrete sites of about 100, about 200, about 300, about 400, about 500, about 600, about 700, about 800, about 900, about 1000, about 2000, about 3000, about 4000, about 5000, about 6000, about 7000, about 8000, about 9000, about 10000, about 20000, about 40000, about 60000, about 80000, about 100000, or about 500000 sites per 1 $mm^2$. In some embodiments, the surface has a density of discrete sites of at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 20000, at least about 40000, at least about 60000, at least about 80000, at least about 100000, or at least about 500000 sites per 1 $mm^2$.

The electrode can be re-charged prior to, between or during, or after detections (e.g., of nucleotide incorporation events). In some cases, the electrode is re-charged in about 20 milliseconds, about 40 ms, about 60 ms, about 80 ms, about 100 ms, about 120 ms, about 140 ms, about 160 ms, about 180 ms, or about 200 ms. In some cases, the electrode is re-charged in less than about 20 milliseconds (ms), less than about 40 ms, less than about 60 ms, less than about 80 ms, less than about 100 ms, less than about 120 ms, less than about 140 ms, less than about 160 ms, less than about 180 ms, about 200 ms, less than about 500 ms, or less than about 1 second.

Cell Circuitry

Figure 4:
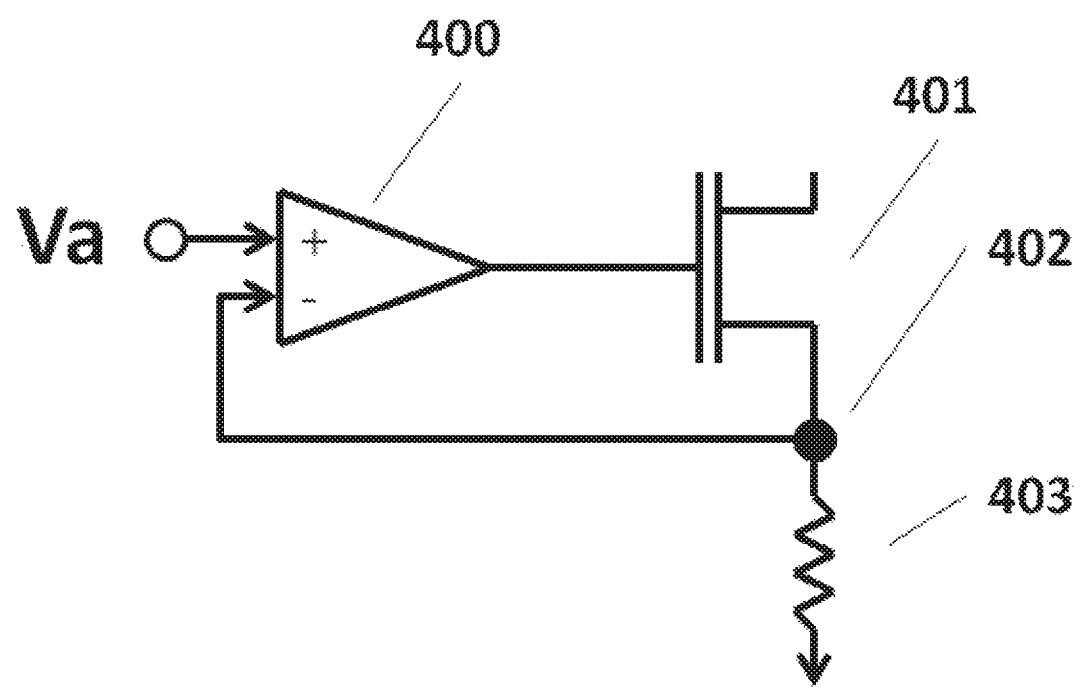
FIG. 4 shows an example of an ultra compact measurement circuit.

An example of cell circuitry is shown in FIG. 4, An applied voltage Va is applied to an opamp 1200 ahead of a MOSFET current conveyor gate 401. Also shown here are an electrode 402 and the resistance of the nucleic acid and/or tag detected by the device 403.

An applied voltage Va can drive the current conveyor gate 401. The resulting voltage on the electrode sis then Va-Vt where Vt is the threshold voltage of the MOSFET. In some instances, this results in limited control of the actual voltage applied to the electrode as a MOSFET threshold voltage can vary considerably over process, voltage, temperature, and even between devices within a chip. This Vt variation can be greater at low current levels where sub-threshold leakage effects can come into play. Therefore, in order to provide better control of the applied voltage, an opamp can be used in a follower feedback configuration with the current conveyor device. This ensures that the voltage applied to the electrode is Va, independent of variation of the MOSFET threshold voltage.

Figure 5:
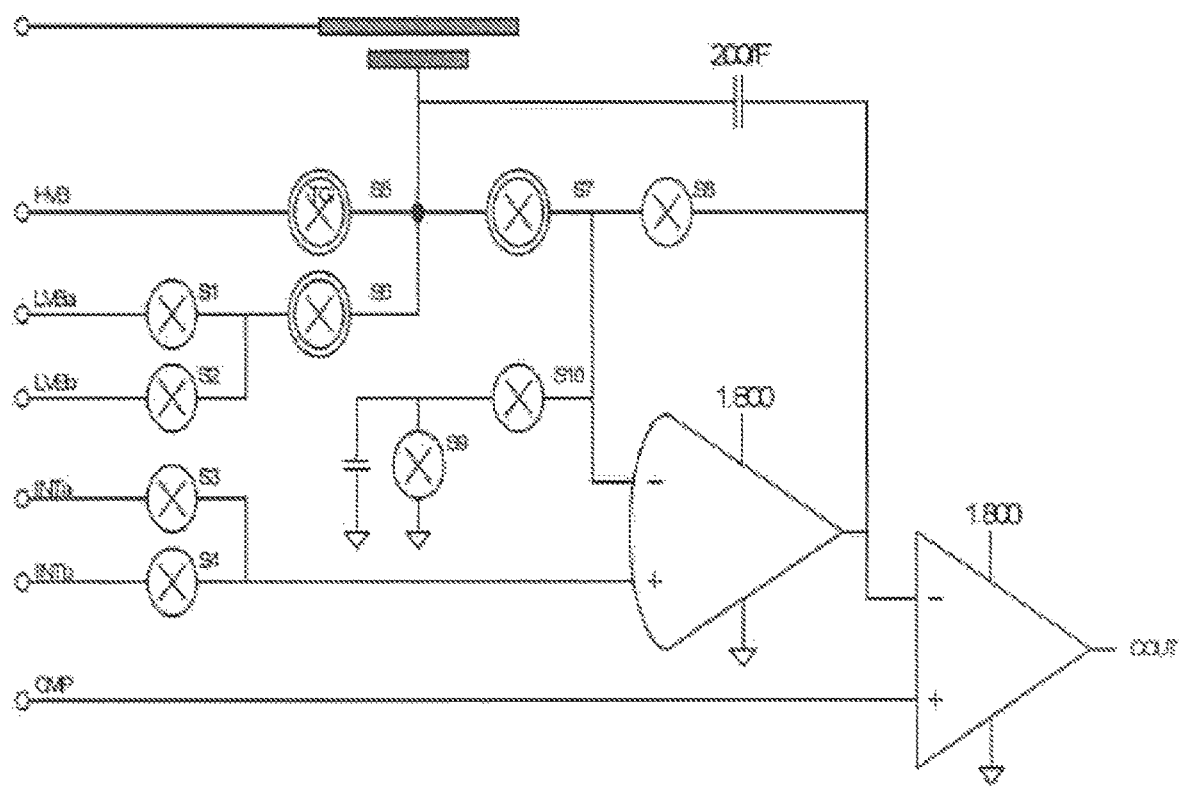
FIG. 5 shows an example of cell analog circuitry.
Figure 5:
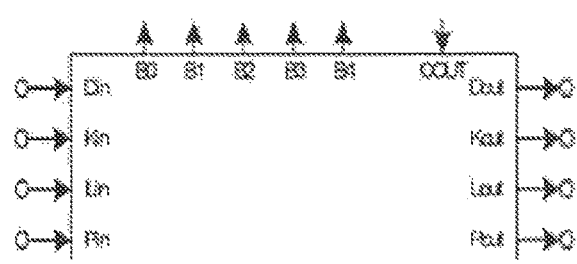

Another example of cell circuitry is shown in FIG. 5 and includes an integrator, comparator, and digital logic to shift in control bits and simultaneously shift out the state of the comparator output. The cell circuitry may be adapted for use with systems and methods provided herein. The B0 through B1 lines may come out of the shift register. The analog signals are shared by all cells within a bank while digital lines may be daisy-chained from cell to cell.

The cell digital logics comprises the 5 bit data shift register (DSR), 5 bit parallel load registers (PLR), control logic, and analog integrator circuit. Using the LIN signal, the control data shifted into the DSR is parallel loaded into the PLR. These 5 bits control digital "break-before-make" timing logic which controls the switches in the cell. In addition the digital logic has a set-reset (SR) latch to record the switching of the comparator output.

The architecture delivers a variable sample rate that is proportional to the individual cell current. A higher current may result in more samples per second than a lower current. The resolution of the current measurement is related to the current being measured. A small current may be measured with finer resolution than a large current, which may be a benefit over fixed resolution measurement systems. There is an analog input which allows the user to adjust sample rates by changing the voltage swing of the integrator. It may be possible to increase the sample rate in order to analyze biologically fast processes or to slow the sample rate (and thereby gain precision) in order to analyze biologically slow processes.

The output of the integrator is initialized to the voltage LVB (low voltage bias) and integrates up to the voltage CMP. A sample is generated every time the integrator output swings between these two levels. Thus the greater the current the faster the integrator output swings and therefore the faster the sample rate. Similarly if CMP voltage is reduced the output swing of the integrator needed to generate a new sample is reduced and therefore the sample rate is increased. Thus simply reducing the voltage difference between LVB and CMP provides a mechanism to increase the sample rate.

A nanopore based sequencing chip may incorporate a large number of autonomously operating or individually addressable cells configured as an array. For example an array of one million cells could be constructed of 1000 rows of cells by 1000 columns of cells. This array enables the parallel sequencing of nucleic acid molecules by measuring the conductance difference when tags released upon nucleotide incorporation events are detected by the nanopore for example. Moreover this circuitry implementation allows the conductance characteristics of the pore-molecular complex to be determined which may be valuable in distinguishing between tags.

The integrated nanopore/bilayer electronic cell structures may apply appropriate voltages in order to perform current measurements. For example, it may be necessary to both (a) control electrode voltage potential and (b) monitor electrode current simultaneously in order to perform correctly.

Moreover it may be necessary to control cells independently from one another. The independent control of a cell may be required in order to manage a large number of cells that may be in different physical states. Precise control of the piecewise linear voltage waveform stimulus applied to the electrode may be used to transition between the physical states of the cell.

In order to reduce the circuit size and complexity it may be sufficient to provide logic to apply two separate voltages. This allows two independent grouping of cells and corresponding state transition stimulus to be applied. The state transitions are stochastic in nature with a relatively low probability of occurrence. Thus it may be highly useful to be able to assert the appropriate control voltage and subsequently perform a measurement to determine if the desired state transition has occurred. For example the appropriate voltage may be applied to a cell and then the current measured to determine whether a bilayer has formed. The cells are divided into two groups: (a) those which have had a bilayer form and no longer need to have the voltage applied. These cells may have a 0V bias applied in order to effect the null operation (NOP)—that is stay in the same state and (b) those which do not have a bilayer formed. These cells will again have the bilayer formation electric voltage applied.

A substantial simplification and circuit size reduction may be achieved by constraining the allowable applied voltages to two and iteratively transitioning cells in batches between the physical states. For example, a reduction by at least a factor of 1.1, 2 3, 4, 5, 6, 7, 8, 9, 10, 20, 30, 40, 50, or 100 may be achieved by constraining the allowable applied voltages.

Arrays of Nanopores

Figure 6:
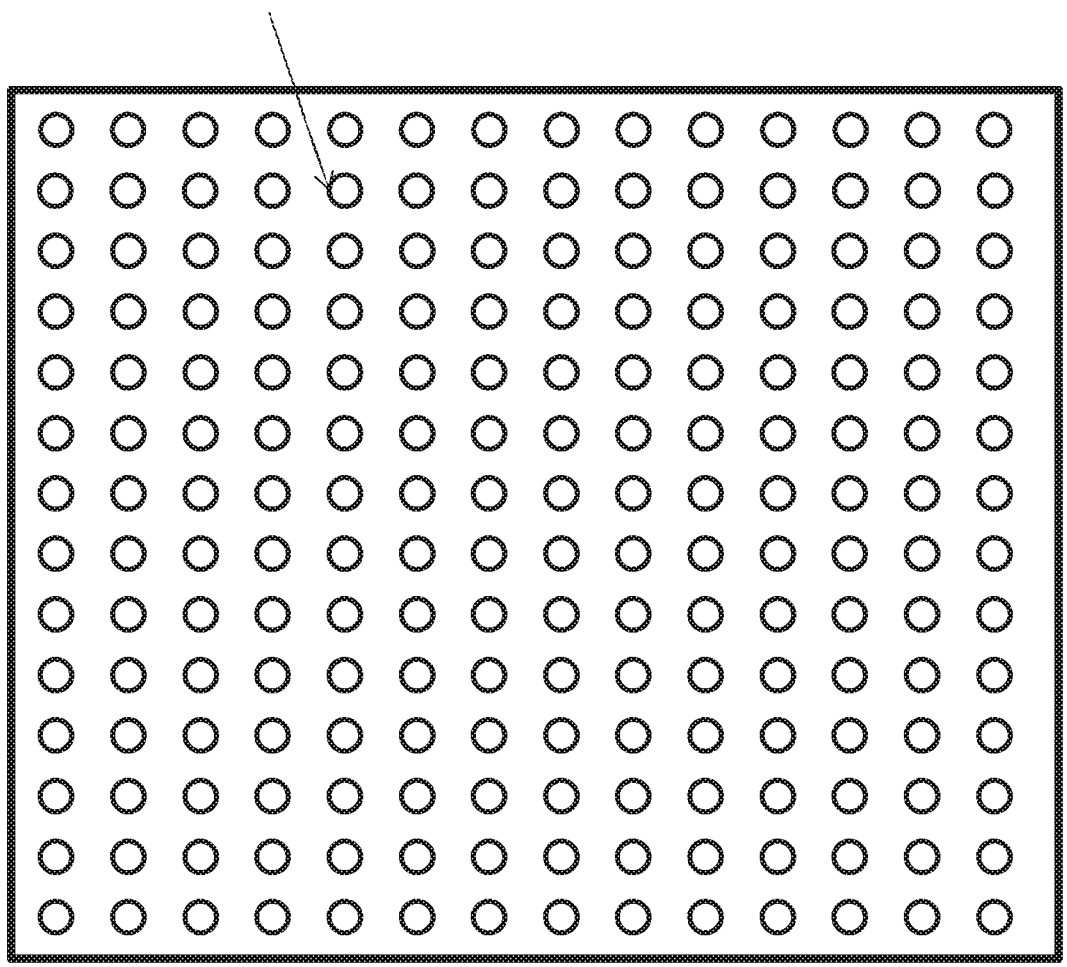
FIG. 6 shows an array of nanopore detectors.

The disclosure provides an array of nanopore detectors (or sensors) for detecting molecules and/or sequencing nucleic acids. With reference to FIG. 6, a plurality of (e.g., nucleic acid) molecules may be detected and/or sequenced sequenced on an array of nanopore detectors. Here, each nanopore location (e.g., 601) comprises a nanopore, optionally attached to a polymerase enzyme and/or phosphatase enzymes. There is also generally a sensor at each array location as described herein. In some examples, an array of nanopores attached to a nucleic acid polymerase is provided, and tagged nucleotides are incorporated with the polymerase. During polymerization, a tag is detected by the nanopore (e.g., by releasing and passing into or through the nanopore, or by being presented to the nanopore).

The array of nanopores may have any suitable number of nanopores. In some instances, the array comprises about 200, about 400, about 600, about 800, about 1000, about 1500, about 2000, about 3000, about 4000, about 5000, about 1 0000, about 15000, about 20000, about 40000, about 60000, about 80000, about 100000, about 200000, about 400000, about 600000, about 800000, about 100000, and the like nanopores. In some instances, the array comprises at least 200, at least 400, at least 600, at least 800, at least 1000, at least 1500, at least 2000, at least 3000, at least 4000, at least 5000, at least 10000, at least 15000, at least 20000, at least 40000, at least 60000, at least 80000, at least 100000, at least 200000, at least 400000, at least 600000, at least 800000, or at least 1000000 nanopores.

The array of nanopore detectors may have a high density of discrete sites. For example, a relatively large number of sites per unit area (i.e., density) allows for the construction of smaller devices, which are portable, low-cost, or have other advantageous features. An individual site in the allay can be an individually addressable site. A large number of sites comprising a nanopore and a sensing circuit may allow for a relatively large number of nucleic acid molectiles to be sequenced at once, such as, for example, through parallel sequencing. Such a system may increase the through-put and/or decrease the cost of sequencing a nucleic acid sample.

The surface comprises any suitable density of discrete sites (e.g., a density suitable for sequencing a nucleic acid sample in a given amount of time or for a given cost). Each discrete site can include a sensor. The surface may have a density of discrete sites greater than or equal to about 500 sites per 1 $nm^2$. In some embodiments, the surface has a density of discrete sites of about 200, about 300, about 400, about 500, about 600, about 700, about 800, about 900, about 1000, about 2000, about 3000, about 4000, about 5000, about 6000, about 7000, about 8000, about 9000, about 10000, about 20000, about 40000, about 60000, about 80000, about 100000, or about 500000 sites per 1 $mm^2$. In some cases, the surface has a density of discrete sites of at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10000, at least 20000, at least 40000, at least 60000, at least 80000, at least 100000, or at least 500000 sites per 1 $mm^2$.

In some examples, a test chip includes an allay of 264 sensors arranged in four separate groups (aka banks) of 66 sensor cells each. Each group is in turn divided into three "columns" with 22 sensors "cells" in each column. The "cell" name is apropos given that ideally a virtual cell comprising a layer and inserted nanopore is limited above each of the 264 sensors in the array (although the device may operate successfully with only a fraction of the sensor cells so populated).

There is a single g I/O pad which applies a voltage potential to the liquid contained within a conductive cylinder mounted to the surface of the die. This "liquid" potential is applied to the top side of the pore and is common to all cells in a detector array. The bottom side of the pore has an exposed electrode and each sensor cell may apply a distinct bottom side potential to its electrode. The current is then measured between the top liquid connection and each cell's electrode connection on the bottom side of the pore. The sensor cell measures the current traveling through the pore as modulated by the tag molecule passing within the pore.

Figure 7:
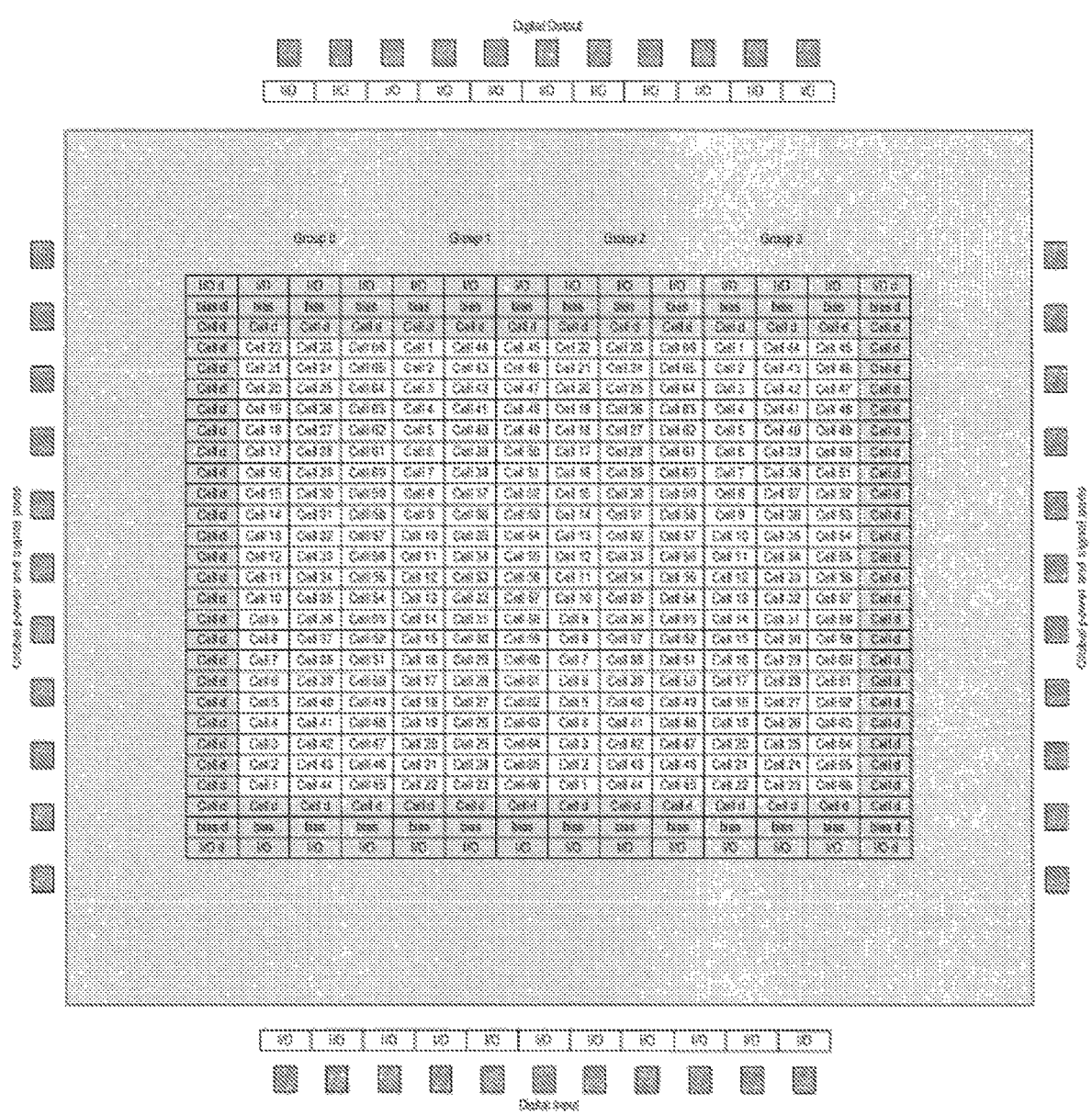
FIG. 7 shows an example of a test chip cell array configuration.

In some cases, five bits control the mode of each sensor cell. With continued reference to FIG. 7, each of the 264 cells in the array may be controlled individually. Values are applied separately to a group of 66 cells. The mode of each of the 66 cells in a group is controlled by serially shifting in 330 (66*5 bits/cell) digital values into a DataShiftRegister (DSR). These values are shifted into the array using the KIN (clock), and DIN (data in) pins with a separate pin pair for each group of 66 cells.

Thus 330 clocks are used to shift 330 bits into the DSR shift register. A second 330 bit Parallel Load Register (PLR) is parallel loaded from this shift register when the corresponding LIN<i> (Load Input) is asserted high. Al the same time as the PLR is parallel loaded the status value of the cell is loaded into the DSR.

A complete operation may include 330 clocks to shift in 330 data bits into the DSR, a single clock cycle with LIN signal asserted high, followed by 330 clock cycles to read the captured status data shifted out of the DSR. The operation is pipelined so that a new 330 bits may be shifted into the DSR simultaneously while the 330 bits are being read out of the array. Thus at 50 MHz clock frequency the cycle time for a read is 331/50 MHz=6.62 us.

Computer Systems for Sequencing Nucleic Acid Samples

Figure 8:
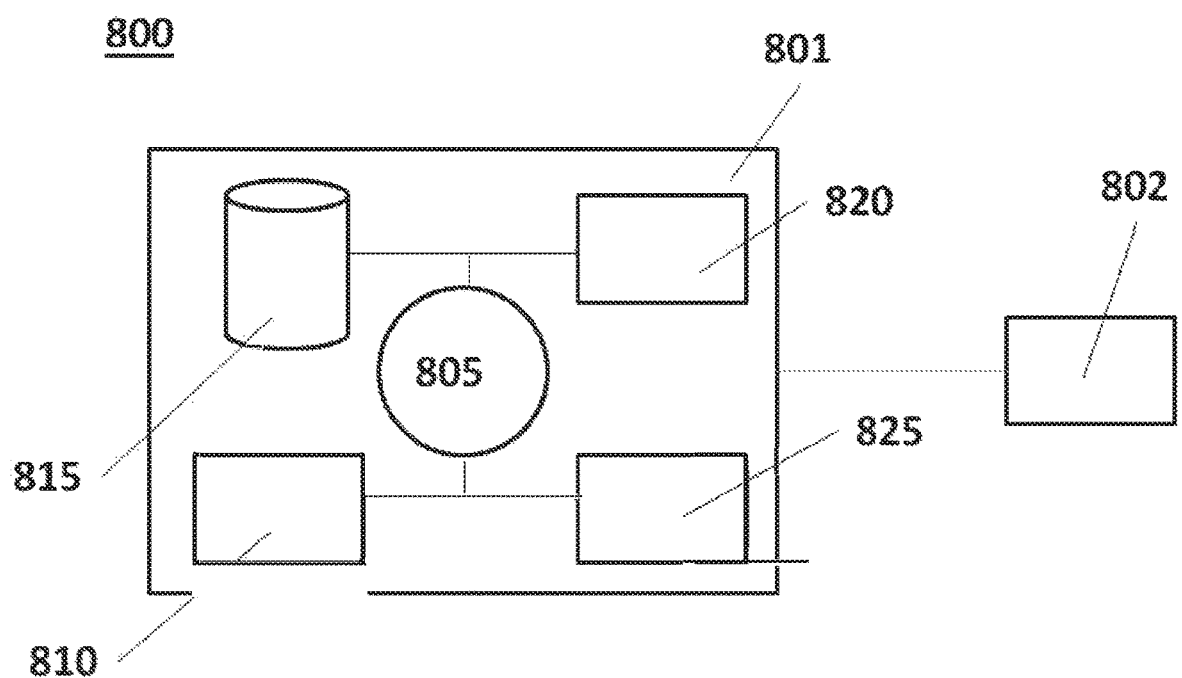
FIG. 8 shows a computer system configured to control a sequencer.

The devices, systems and methods of the disclosure may be regulated with the aid of computer systems. FIG. 8 shows a system 800 comprising a computer system 801 coupled to a nanopore detection and/or nucleic acid sequencing system 802. The computer system 801 may be a server or a plurality of servers. The computer system 801 may be programmed to regulate sample preparation and processing, and nucleic acid sequencing by the sequencing system 802. The nanopore detection and/or sequencing system 802 may be a nanopore-based sequencer (or detector), as described herein.

The computer system may be programmed to implement the methods of the disclosure. The computer system 801 includes a central processing unit (CPU, also "processor" herein) 805, which can be a single core or multi core processor, or a plurality of processors for parallel processing. The processor 805 can be part of a circuit, such as an integrated circuit. In some examples, the processor 805 can be integrated in an application specific integrated circuit (ASIC). The computer system 801 also includes memory 810 (e.g., random-access memory, read-only memory, flash memory), electronic storage unit 815 (e.g., hard disk), communications interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communications bus (solid lines), such as a motherboard. The storage unit 815 can be a data storage unit (or data repository) for storing data. The computer system 801 may be operatively coupled to a computer network ("network") with the aid of the communications interface 820. The network can be the Internet, an internet and/or extranet, or an intranet and/or extranet that is in communication with the Internet. The network can include one or more computer servers, which can enable distributed computing.

In some examples, the computer system 801 includes a field-programmable gate array (FPGA). The processor 805 in such a case may be excluded.

Methods of the disclosure can be implemented by way of machine (or computer processor) executable code (or software) stored on an electronic storage location of the computer system 801, such as, for example, on the memory 810 or electronic storage unit 815. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine have a processer adapted to execute the code, or can be compiled during runtime. The code can be supplied in a programming language that can be selected to enable the code to execute in a pre-compiled or as-compiled fashion.

The computer system 801 can be adapted to store user profile information, such as, for example, a name, physical address, email address, telephone number, instant messaging (IM) handle, educational information, work information, social likes and/or dislikes, and other information of potential relevance to the user or other users. Such profile information can be stored on the storage unit 815 of the computer system 801.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., ROM, RAM) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions afire software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RI) and infrared (IR) data communications. Common forms of computer-readable media therefore include for example: a floppy disk, a flexible disk, hard disk, magnetic tape, any other magnetic medium, a CI)-ROM, DVD or DVD-ROM, any other optical medium, punch cards paper tape, any other physical storage medium with patterns of holes, a RAM, a RUM, a PROM and :EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Nucleic Acid Sequencing

Methods for sequencing nucleic acids may include retrieving a biological sample having the nucleic acid to be sequenced, extracting or otherwise isolating the nucleic acid sample from the biological sample, and in some cases preparing the nucleic acid sample for sequencing.

Figure 9:
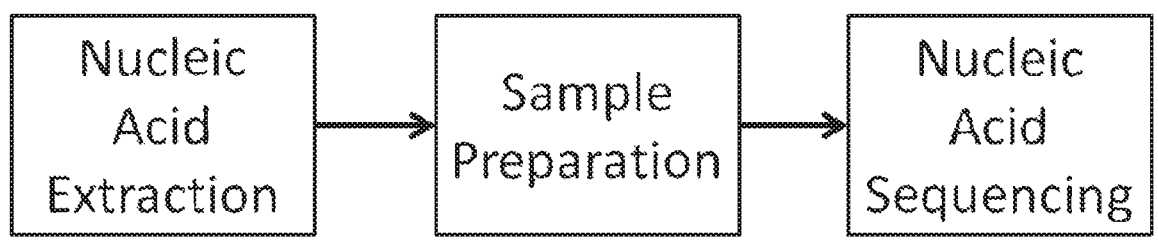
FIG. 9 shows a method for nucleic acid sequencing.

FIG. 9 schematically illustrates a method for sequencing a nucleic acid sample. The method comprises isolating the nucleic acid molecule from a biological sample (e.g., tissue sample, fluid sample), and preparing the nucleic acid sample for sequencing. Sequencing can involve determining abase makeup, including order, of individual nucleic acid bases of the nucleic acid sample. In some instances, the nucleic acid sample is extracted from a cell. Examples of techniques for extracting nucleic acids are using lysozyme, sonication, extraction, high pressures or any combination thereof. The nucleic acid is cell-free nucleic acid in some cases and does not require extraction from a cell.

In some cases, a nucleic acid sample may be prepared for sequencing by a process that involves removing proteins, cell wall debris and other components from the nucleic acid sample. There are many commercial products available for accomplishing this, such as, for example, spin Ethanol precipitation and centrifirgation may also be used The nucleic acid sample may be partitioned (or fractured) into a plurality of fragments, which may facilitate nucleic acid sequencing, such as with the aid of a device that includes a plurality of nanopores in an array. However, fracturing the nucleic acid molecule(s) to be sequenced may not be necessary.

In some instances, long sequences are determined (i.e., "shotgun sequencing" methods may not be required). Any suitable length of nucleic acid sequence may be determined. For instance, at least about 5, about 10, about 20, about 30, about 40, about 50, about 100, about 200, about 300, about 400, about 500, about 600, about 700, about 800, about 800, about 1000, about 1500, about 2000, about 2500, about 3000, about 3500, about 4000, about 4500, about 5000, about 6000, about 7000, about 8000, about 9000, about 10000, about 20000, about 40000, about 60000, about 80000, or about 100000, and the like bases may be sequenced. In some instances, at least 5, at least 10, at least 20, at least 30, at least 40, at least 50, at least 100, at least 200, at least 300, at least 400, at least 500, at least 600, at least 700, at least 800, at least 800, at least 1000, at least 1500, at least 2000, at least 2500, at least 3000, at least 3500, at least 4000, at least 4500, at least 5000, at least 6000, at least 7000, at least 8000, at least 9000, at least 10000, at least 20000, at least 40000, at least 60000, at least 80000, at least 100000, and the like bases ate sequenced. In some instances the sequenced bases are contious. In some instances, the sequenced bases are not contiguous. For example, a given number of bases can be sequenced in a row. In another example, one or more sequenced bases may be separated by one or more blocks in which sequence information is not determined and/or available. In some embodiments, a to can be sequenced multiple times (e.g., using a circular nucleic acid template), optionally generating redundant sequence information. In some cases, software is used to provide the sequence. In some cases, the nucleic acid sample may be partitioned prior to sequencing. In some instances the nucleic acid sample strand may be processed so that a given duplex DNA or RNA/DNA region is made circular such that the corresponding sense and antisense portions of the duplex DNA or RNA/DNA region are included in the circular DNA or circular DNA/RNA molecule. In such an instance, the sequenced bases from such a molecule may allow easier data assembly and checking of base position readings.

Systems and methods of the disclosure may be used to sequence various types of biological samples, such as nucleic acids (e.g., DNA, RNA) and proteins. In some embodiments, the methods, devices and systems described herein can be used to sort biological samples (e.g., proteins or nucleic acids). The sorted samples and/or molecules can be directed to various bins for further analysis.

Nucleic acid molecules can be sequenced directly (e.g., by passing the nucleic acid through a nanopore as shown in FIG. 2B) or indirectly (e.g., by detection of released tag molecules as shown in FIG. 2C).

Methods and Systems for Sequencing Nucleic Acid Samples

Described herein are methods, devices and systems for sequencing nucleic acids using, or with the aid of, one or more nanopores. The one or more nanopores may be in a membrane (e.g., lipid bi-layer) that is disposed adjacent or in sensing proximity to an electrode that is part of, or coupled to, an integrated circuit.

In some examples, a nanopore device includes a single nanopore in a membrane that is adjacent or sensing proximity to an electrode. In other examples, a nanopore device includes at least 1, 2, 3, 4, 5, 6, 7, 8, 9, 10, 20, 30, 40, 50, 60, 70, 80, 90, 100, 1000, or 10,000 nanopores in proximity to a sensor circuit or sensing electrodes. The one or more nanopore may be associated with an individual electrode and sensing integrated circuit or a plurality of electrodes and sensing integrated circuits.

A system may include a reaction chamber that includes one or more nanopore devices. A nanopore device may be an individually addressable nanopore device (e.g., a device that is capable of detecting a signal and providing an output independent of other nanopore devices in the system). An individually addressable nanopore can be individually readable. In some cases, an individually addressable nanopore can be individually writable. As an alternative, an individually addressable nanopore can be individually readable and individually writable. The system can include one or more computer processors for facilitating sample preparation and various operations of the disclosure, such as nucleic acid sequencing. The processor can be coupled to nanopore device.

A nanopore device may include a plurality of individually addressable sensing electrodes. Each sensing electrode can include a membrane adjacent to the electrode, and one or more nanopores in the membrane.

Methods, devices and systems of the disclosure may detect nucleic acid bases as a nucleic acid molecule passes through the nanopore. The nucleic acid molecule can be modified to more readily differentiate between the various bases as they pass through the nanopore as described in PCT Patent Publication No. WO2007/146158, which is incorporated by reference in its entirety.

RNA Speed Bumps and Bulky Structures

Systems and methods for polynucleotide sequencing are provided herein. In particular, the presently disclosed systems and methods optimize control, speed, movement, and/or translocation of a molecule (e.g., a polynucleotide) within, through, or at least partially through a nanopore (or some type of protein or mutant protein). In some cases, the rate of passage is sufficiently slow or stopped for sufficient amounts of time in order to accumulate sufficient current blocking information to identify the molecule and/or sequence contiguous nucleotides in a single-stranded area of a polynucleotide. That is, in some embodiments, speed bumps (e.g., oligonucleotide n-mers) can be bound to a target polynucleotide so that these double-stranded portions are "stuck" within a portion of the nanopore for an amount of time while a single-stranded portion ("ss") of the target is interrogated and genetic analysis is generated and detected. After an amount of time, the "stuck" oligonucleotide can be melted away and the sample can be translocated through the nanopore. In some embodiments, the oligonucleotide n-mers can be selected such that each oligonucleotide n-mer melts away or is removed at a uniform rate such that the sample moves through the nanopore at a controlled and/or constant rate. The use of speed bump molecules is described in PCT Patent Publication No. WO2012/088339, and PCT Patent Publication No. WO2012/088341 which are incorporated by reference in its entirety.

Surprisingly, the rate at which the nucleic acid passes through the nanopore can be controlled using speed bumps that comprise ribonucleic acid (RNA). The speed bumps can comprise universal bases, optionally located along an RNA backbone. Nucleic acid molecules can be sequenced by passing the molecule through a nanopore as described herein, but the rate of nucleic acid passage is often too rapid to determine the nucleic acid sequence accurately and/or to resolve individual nucleic acid positions. RNA speed bumps can effectively reduce the rate of and/or control the speed at which a nucleic acid molecule passes through a nanopore.

In an aspect, a method for sequencing a nucleic acid molecule comprises providing a chip comprising at least one nanopore in a membrane that is disposed adjacent or in proximity to an electrode. The electrode can be adapted to detect the nucleic acid molecule or a portion thereof. The method can further include directing the nucleic acid molecule through the nanopore. Progression of the nucleic acid molecule through the nanopore can be stopped or stalled with the aid of at least one ribonucleic acid (RNA) speed-bump molecule associated with the nucleic acid molecule. The method can further include sequencing the nucleic acid molecule or a portion thereof as the nucleic acid molecule passes through the nanopore.

In another aspect, a method for obtaining sequence information of a nucleic acid molecule comprises forming a duplex segment containing at least one ribonucleic acid (RNA) speed bump molecule associated with the nucleic acid molecule and flowing the nucleic acid molecule through a nanopore in a membrane. The membrane is disposed adjacent to or in proximity to an electrode, and upon flowing the nucleic molecule through the nanopore, the duplex segment is directed towards the nanopore. The method can further include obtaining electrical signals from the electrode upon the flow of the nucleic acid molecule through the nanopore. The electrical signals can be associated with the interaction of one or more bases of the nucleic acid molecule and the nanopore and the flow of the nucleic acid molecule can be reduced with the aid of the duplex segment.

In some embodiments, the RNA speed-bump molecule is non-covalently associated with the nucleic acid molecule (e.g., forms non-covalent bonds such as base pair interactions between the speed-bump and the nucleic acid).

The RNA speed-bump molecule can comprises an oligonucleotide containing a sequence of one or more oligonucleotide bases. The speed-bump molecule can have any length, including up to 2, 3, 4, 5, 6, 7, 8, 9, 10, 11, 12, 13, 14 15, 16, 17, 18, 19, 20, or more oligonucleotide bases. In some cases, the RNA speed-bump molecule has universal bases, morpholines, glycol nucleotides, abasic nucleotides, methylated nucleobases, modified bases, non-binding base mimics, peptide nucleic acids (PNA), locked nucleic acids, or any combination thereof.

Speed bump molecules can associate with the nucleic acid on one or more sides of the membrane. In some embodiments, the RNA speed-bump molecule is associated with the nucleic acid molecule on a cis side of the membrane (e.g., the side farther from the electrode). In some embodiments, the RNA speed-bump molecule is associated with the nucleic acid molecule on a trans side of the membrane (e.g., the side nearer to the electrode). In some instances, the RNA speed-bump molecule is associated with the nucleic acid molecule on a cis side of the membrane and on a trans side of the membrane. The RNA speed-bump molecule may dissociate from the nucleic acid molecule as the nucleic acid molecule passes through the nanopore. In some embodiments, the method further comprises dissociating the RNA speed bump molecule from the nucleic acid molecule prior to flowing a portion of the nucleic molecule included in the duplex segment through the nanopore. The nucleic acid molecule can be single-stranded.

The progression of the nucleic acid molecule through the nanopore can be slowed, stopped or stalled with the aid of a plurality of RNA speed-bump molecules associated with the nucleic acid molecule. The flow can be reduced upon the interaction of the RNA speed bump molecule with the nanopore (e.g., the nanopore contains a constriction that restricts the flow of the nucleic acid molecule through the nanopore). Any suitable number of bases can be identified (e.g., sequenced by the nanopore) when the progression of the nucleic acid molecule through the nanopore is stopped or stalled. In some embodiments, a single base of the nucleic acid molecule is identified. In some instances, up to 2, 3, 4, 5, 7, 8, 9, 10, or more bases of the nucleic acid molecule is identified (e.g., as a group).

In some instances, the method further comprises trapping the nucleic acid molecule in the nanopore. The nucleic acid molecule can be trapped in the nanopore with the aid of bulky structures formed at one or more end portions of the nucleic acid molecule. In some cases, the nucleic acid molecule is trapped in the nanopore with the aid of bulky structures affixed (e.g., ligated) to one or more end portions of the nucleic acid molecule. In some embodiments, the method further comprises reversing a direction of flow of the nucleic acid molecule. The nucleic acid molecule or a portion thereof can be re-sequenced by reversing the direction of flow of the nucleic acid molecule.

In an aspect, the present invention is directed to a method for detecting and/or identifying a sequence in a test polynucleotide using a nanopore detector. The polynucleotide sequence can be trapped in the nanopore by one or two bulky structures formed at the end(s) of the polynucleotide sequence, so that the same test polynucleotide can be read multiple times by the same nanopore detector. Furthermore, each bulky structure can be bound to the 5' end or the 3' end to thread the sample polynucleotide into the pore in a known direction.

Known speed bumps can be used to bind to known sequences in the test polynucleotide for the detection/identification of the known sequences. This method can be used without limitation to detect whether the test polynucleotide has correctly threaded into the nanopore, which sample source the test polynucleotide is from, and individually identify the test polynucleotide trapped in the nanopore. Furthermore, the test polynucleotide may further comprise a reference signal indicator to generate electrical signals that can be used as reference of calibration for other electrical signals obtained from the same nanopore. Furthermore, multiple test polynucleotides can be analyzed by multiple nanopores at the same time for simultaneous sequencings and/or molecular characterizations. The multiple nanopores can be individually addressable and/or have an individually applied electric potential. Thus, multiple test polynucleotides can be analyzed simultaneously, optionally first to identify the polynucleotides having one or more desired known sequences. The polynucleotides that do not have the desired known sequence can be released without further characterizations. The polynucleotides having the desired known sequences can be further characterized, and optionally isolated and concentrated as described herein.

A random speed bump pool can be used to bind to the test polynucleotide or a fragment thereof in a random fashion. Thus, each nucleotide of the test polynucleotide or the fragment thereof may be stalled in the nanopore for a time long enough to collect the nucleotide sequence information. The nucleotide sequence of the test polynucleotide or the fragment thereof can be identified by taking all the sequence information obtained together. The test polynucleotide may further comprise known structures such as direction identifiers, reference signal identifiers, sample source identifiers, sample identifiers to provide information (e.g., formation of the bulky structures), source of the test polynucleotide, and identification of the test polynucleotide. The test polynucleotide may further comprise an isolation tag to isolate and concentrate the test polynucleotide. In some embodiments, multiple test polynucleotides are detected/identified by multiple nanopores (e.g., in a nanopore array). The method described herein can be applied to each test polynucleotide detected/identified. The nanopores can be individually addressed and controlled to selectively detect/identify/collect/concentrate test polynucleotide(s) therein.

Figure 10:
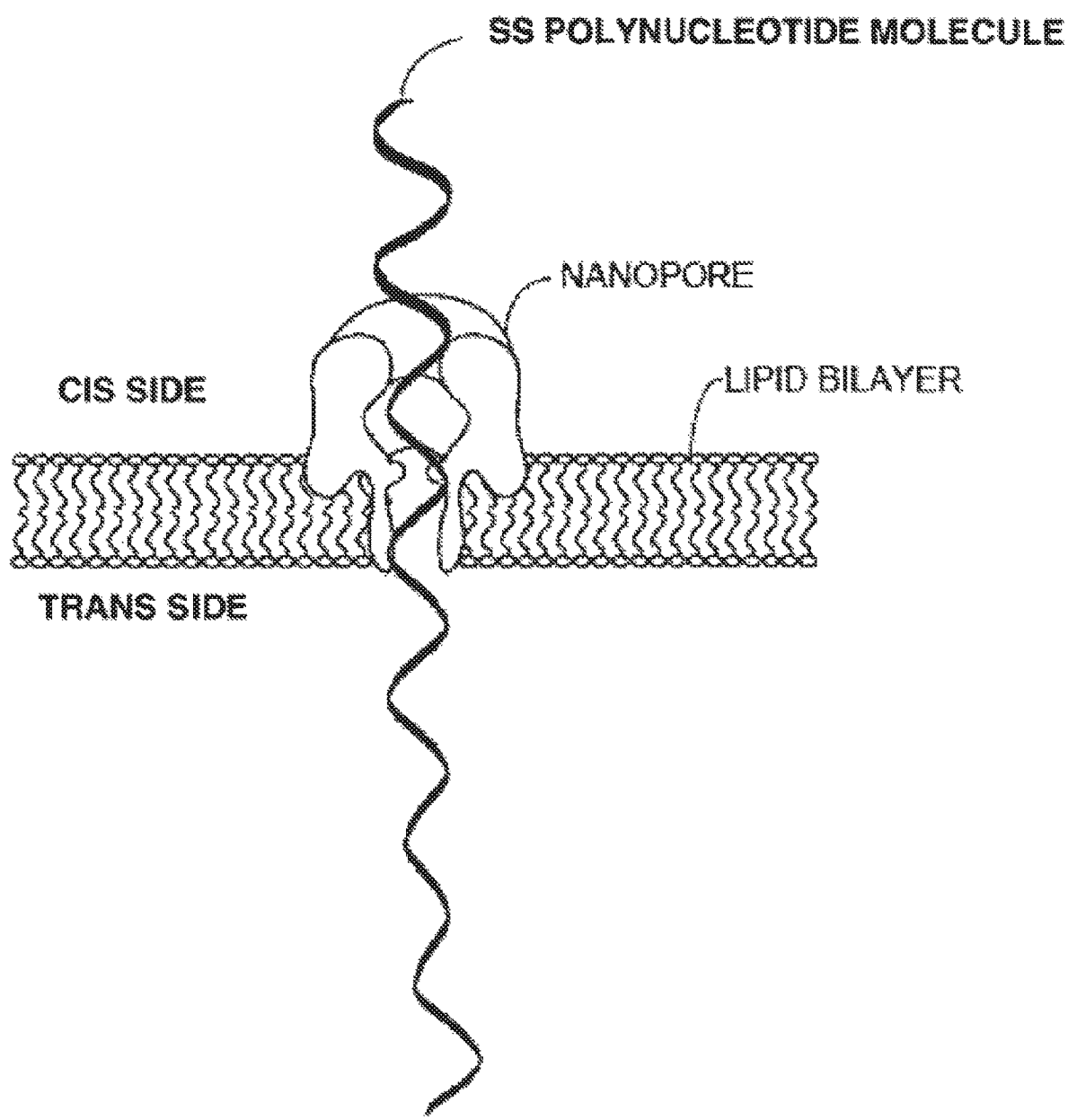
FIG. 10 illustrates the passage of a single stranded (ss) test polynucleotide molecule through a nanopore.

As illustrated in FIG. 10, a single-stranded. (ss) polynucleotide molecule can go through a nanopore under an applied electric potential. The ss polynucleotide may be a test polynucleotide. A set of electrical signals corresponding to the blockages of ion flow through the nanopore by the ss polynucleotide molecule can be detected as the ss polynucleotide molecule is threaded through the nanopore. In the absence of speed bumps or bulky structures, the ss polynucleotide molecule may encounter little resistance and travels through the nanopore too quickly for electrical signals to be reliably recorded for sequencing of the ss polynucleotide. In the illustrated example, the ss polynucleotide is directed through the nanopore from a cis side of the membrane (i.e., side of the membrane disposed away from a sensing electrode) to a trans side of the membrane (i.e., side of the membrane disposed towards the sensing electrode).

Figure 11:
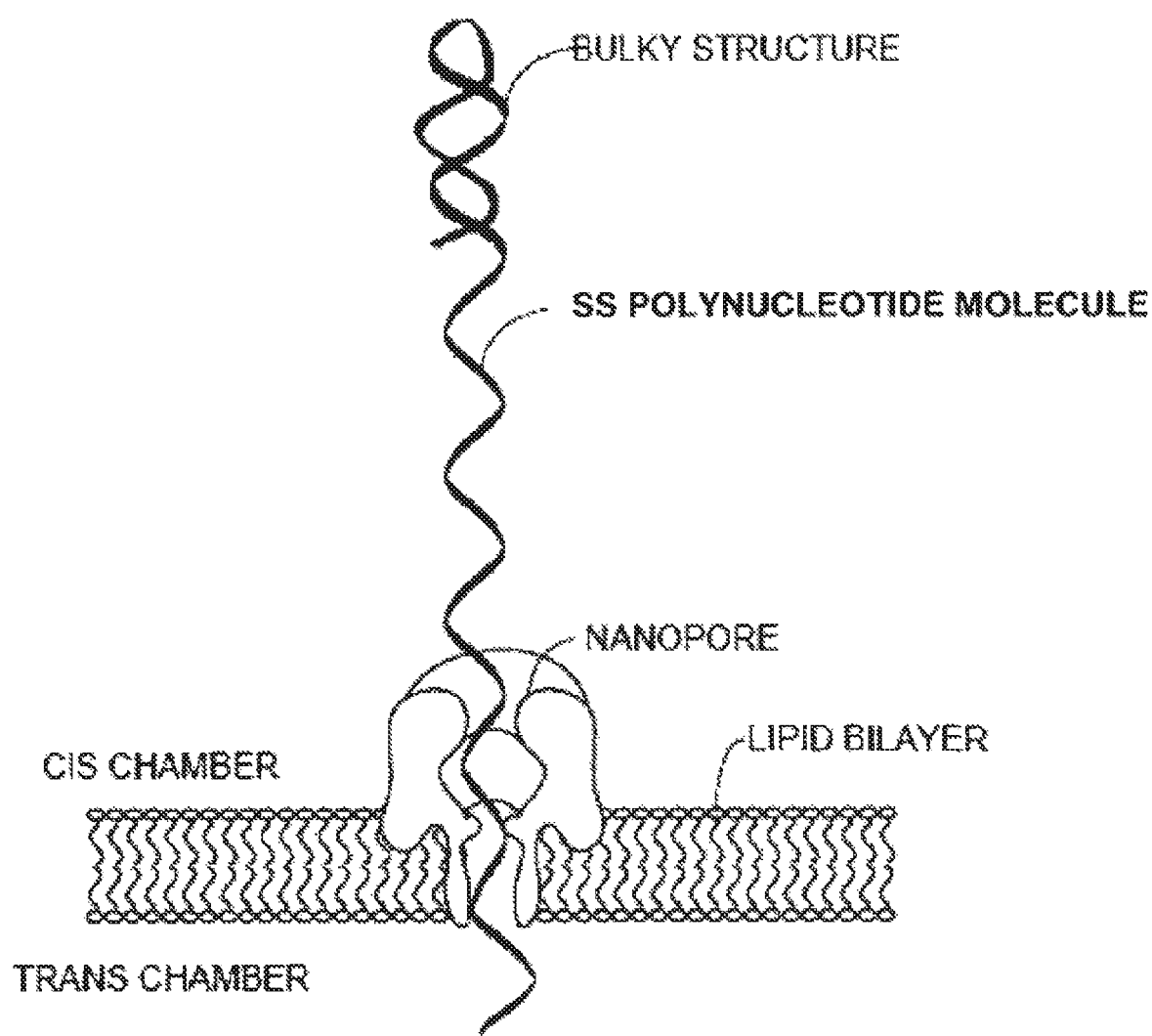
FIG. 11 illustrates a bulky structure formed at the trailing end of a ss test polynucleotide molecule to stall the passage of the ss test polynucleotide through a nanopore.

Bulky structures (BSs) may be used to slow or stop the passage of as polynucleotide through a nanopore. FIG. 11 illustrates a trailing end BS used to stop the passage of a ss test polynucleotide molecule through a nanopore. The BS can be a hairpin structure formed at one end of the ss test polynucleotide by wrapping the trailing end of the ss test polynucleotide upon itself. Typically, the ss test polynucleotide can be threaded through the nanopore under an applied electric potential until the bulky hairpin structure reaches the entrance of the nanopore. Since the hairpin structure is larger than the diameter of the nanopore, the ss test polynucleotide is stalled in the nanopore long enough to obtain a set of electrical signals of the ss test polynucleotide. However, the electrical signals obtained may reflect the structure of only a portion of the polynucleotide that is in front of the hairpin or in front of the specific duplex region and therefore in or near the constriction area of the nanopore.

Figure 12:
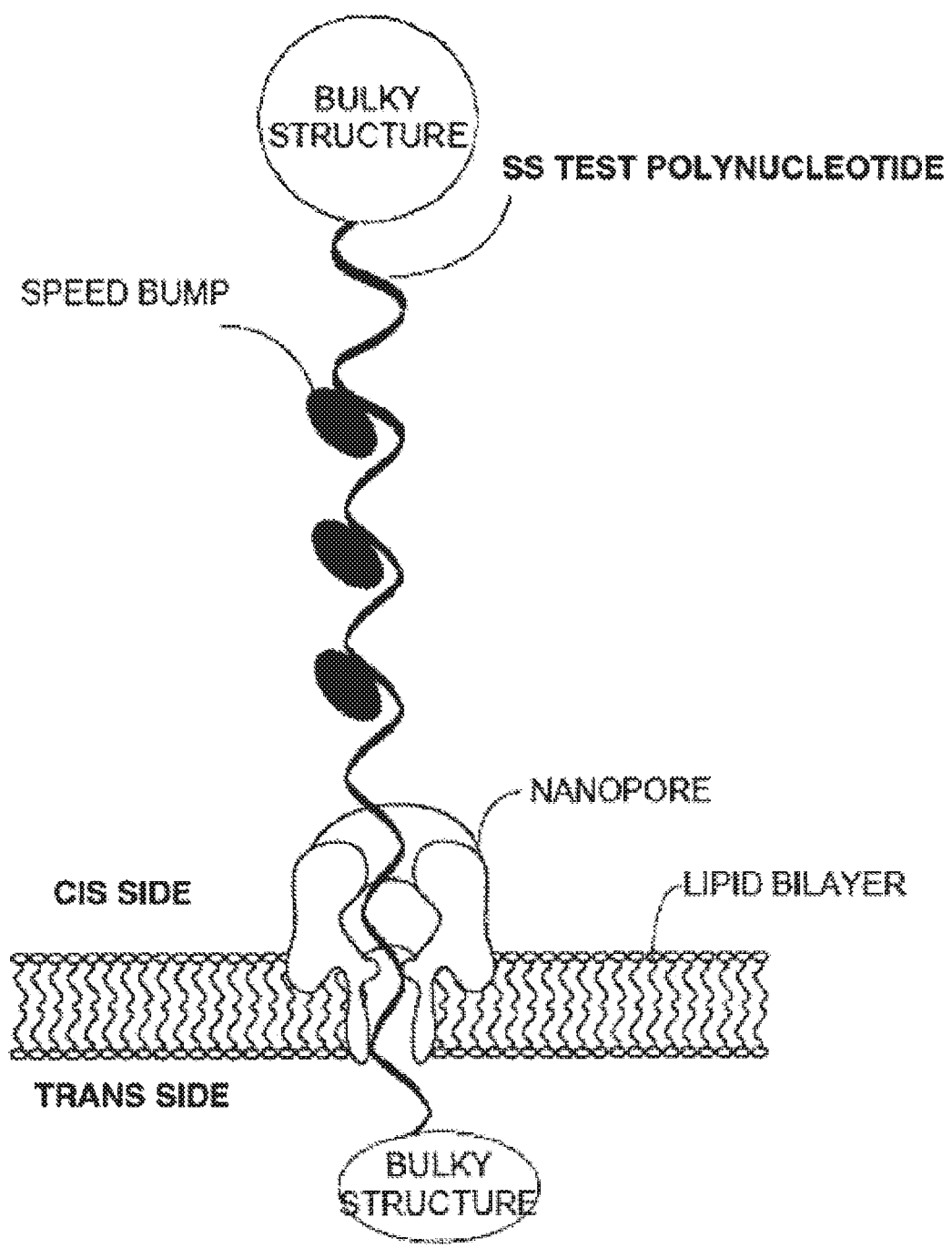
FIG. 12 illustrate multiple speed bumps bound to as test polynucleotide molecule, wherein the ss test polynucleotide is trapped in a nanopore by having bulky structures on both ends.

FIG. 12 illustrates as test polynucleotide trapped in a nanopore by two bulky structures. The nanopore detection is carried out at a working temperature that may be lower than room temperature and/or the temperature at which the bulky structures form so that one or more shorter polynucleotide duplex sections can be formed between speed bumps and the ss test polynucleotide (speed bump-test polynucleotide duplex segments). The speed bump-test polynucleotide duplex segment can slow or stall the ss test polynucleotide for a sufficient dwelling time to obtain sequence information of the ss test polynucleotide segment in front of the speed bump-test polynucleotide duplex segment and the first basepair of the speed bump-test polynucleotide duplex segment in the flow direction of the ss test polynucleotide. Then the speed bump-test polynucleotide duplex segment may dissociate and the ss test polynucleotide can move forward through the nanopore until stalled by another speed bump-test polynucleotide duplex segment or stalled, slowed or stopped by a bulky structure on one end of the ss test polynucleotide. Once the ss test polynucleotide reaches one end, the electric potential can be optionally reversed in polarity to move the ss test polynucleotide in a reversed direction and repeat the process as desired.

When the ss test polynucleotide has an unknown sequence (e.g., sample polynucleotide), a random speed bump pool can be constructed to bind to random sections of the ss test polynucleotide. As every section of the ss test polynucleotide can be bound by at least one speed bump in the random speed bump pool, the binding patterns achieved by contacting a ss test polynucleotide with a random speed bump pool each time can be random (e.g., FIG. 13). Thus, the segments whose sequence information is obtained are also random for each run (e.g., FIG. 14). However, repeating the process as described allows each and every nucleotide of the unknown sequence to be identified by the nanopore detector. Thus, the whole unknown sequence can be constructed by overlapping the obtained sequence information of random sections of the ss test polynucleotide.

Figure 15:
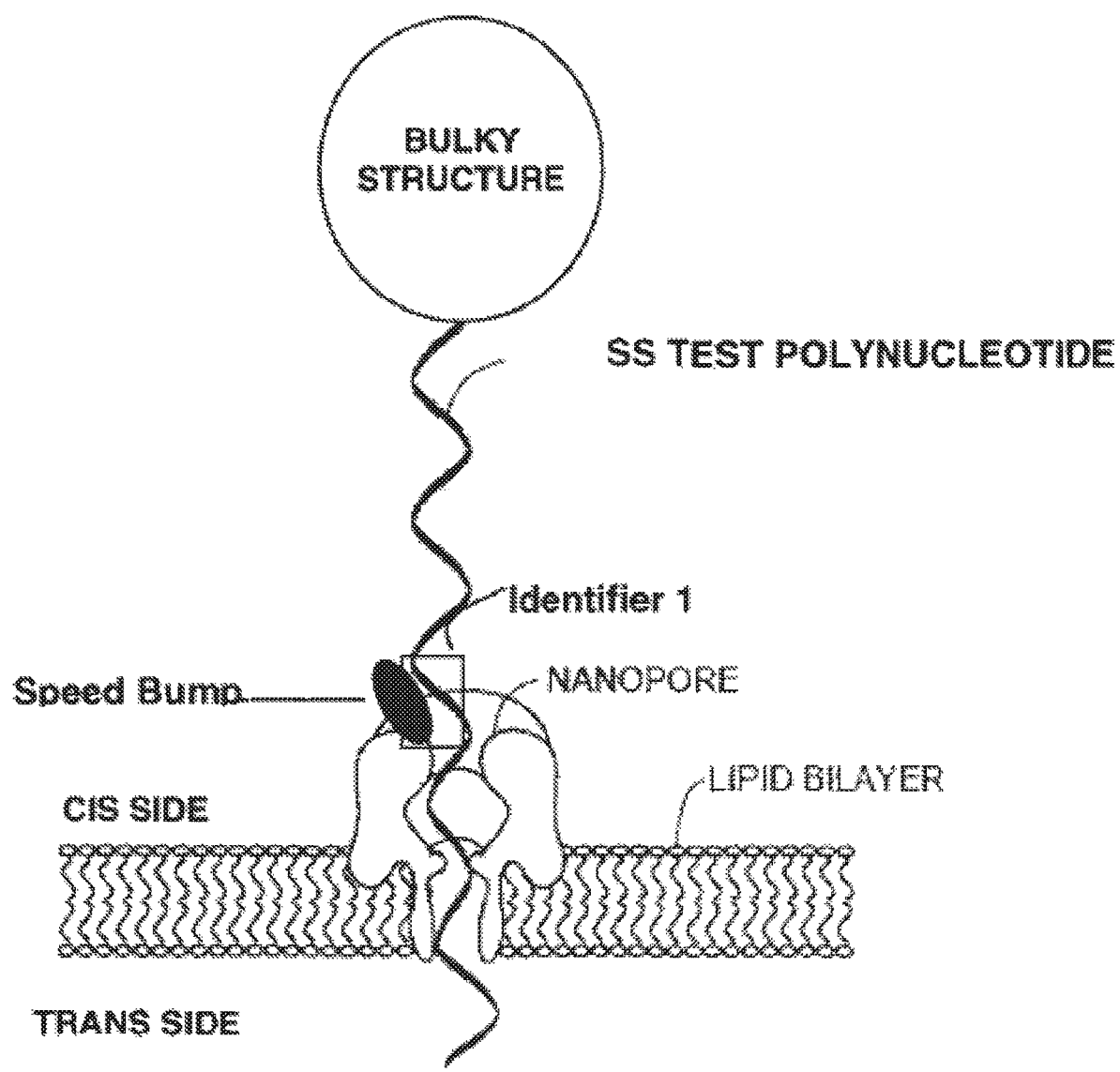
FIG. 15 illustrates a speed bump bound to as test polynucleotide having a bulky structure at a first end to stall its passage through a nanopore.
Figure 16:
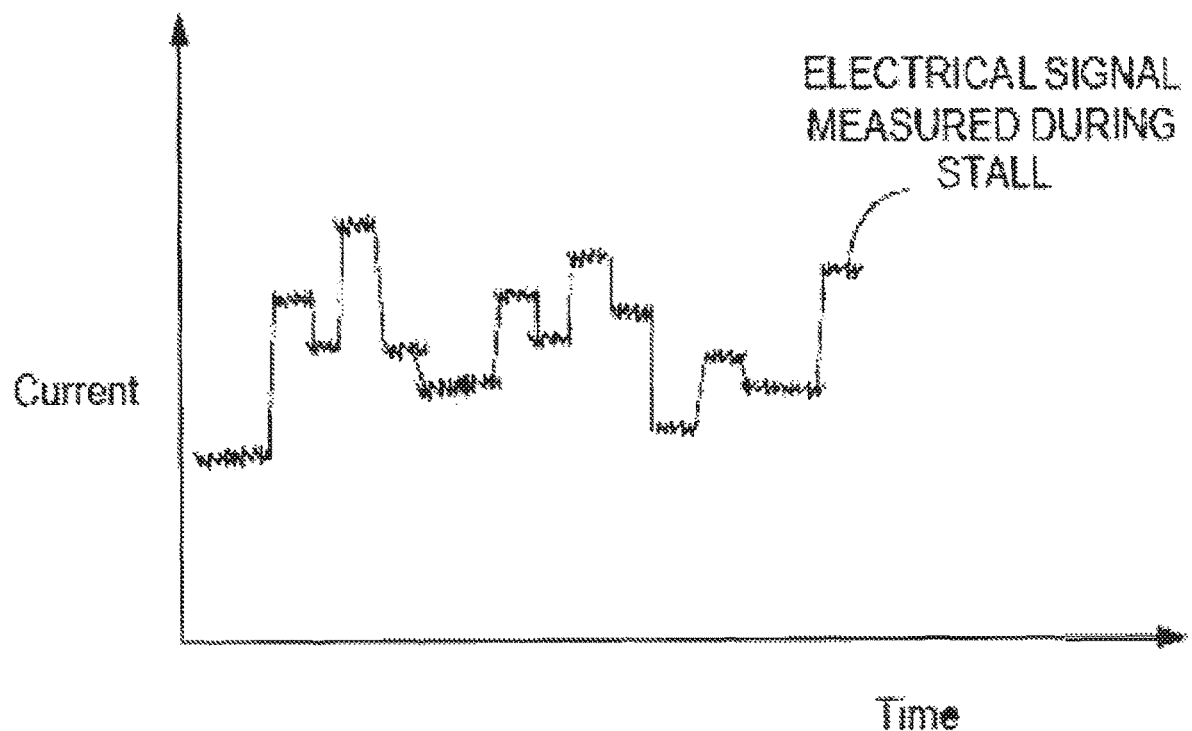
FIG. 16 illustrates multiple sets of electrical signals obtained by a nanopore detector according to the present invention.

When the ss test polynucleotide comprises one or more known sequences (e.g., identifiers), the method described herein can also be used to detect the presence of one or more identifiers and/or to identify a sequence on the ss test polynucleotide that is in front of the identifier in the flow direction of the ss test polynucleotide. The ss test polynucleotide can have BS on only one end (FIG. 15) or both ends. The nanopore detector is operated at a working temperature, optionally lower than room temperature. A speed bump pool comprises speed bumps that can bind specifically to the identifier (e.g., identifier 1, FIG. 15) to form a speed bump-identifier duplex segment can be used. The speed bump-identifier duplex segment can stall the ss test polynucleotide and a set of electrical signals can be obtained. These signals can be characterized to show presence of the identifier or to identify the sequence of the segment before the identifier in the flow direction of the ss test polynucleotide. An example of such electrical signals is shown in FIG. 16.

Design and Construction of Test Polynucleotides from a Sample Polynucleotide

In an embodiment, a sample polynucleotide is linked with various functional moieties to facilitate nanopore sequencing and/or identifications. Examples of functional moieties include, without limitation, pre-bulky structures and identifiers as described herein, and isolation tags to facilitate isolation and enrichment of the sample polynucleotide. The functional moieties optionally comprise one or more nucleotides.

The sample polynucleotide may be a synthetic polynucleotide or a polynucleotide obtained from a biological sample. In an embodiment, the sample polynucleotide has 1 to about 100,000 bases, 1 to about 10,000 bases, 1 to about 1,000 bases, 1 to about 500 bases, 1 to about 300 bases, 1 to about 200 bases, 1 to about 100 bases, about 5 to about 100,000 bases, about 5 to about 10,000 bases, about 5 to about 1,000 bases, about 5 to about 500 bases, about 5 to about 300 bases, about 5 to about 200 bases, about 5 to about 100 bases, about 10 to about 100,000 bases, about 10 to about 10,000 bases, about 10 to about 1,000 bases, about 10 to about 500 bases, about 10 to about 300 bases, about 10 to about 200 bases, about 10 to about 100 bases, about 20 to about 100,000 bases, about 20 to about 10,000 bases, about 2.0 to about 1,000 bases, about 20 to about 500 bases, about 20 to about 300 bases, about 20 to about 200 bases, about 20 to about 100 bases, about 30 to about 100,000 bases, about 30 to about 10,000 bases, about 30 to about 1,000 bases, about 30 to about 500 bases, about 30 to about 300 bases, about 30 to about 200 bases, about 30 to about 100 bases, about 50 to about 100,000 bases, about 50 to about 10,000 bases, about 50 to about 1,000 bases, about 50 to about 500 bases, about 50 to about 300 bases, about 50 to about 200 bases, or about 50 to about 100 bases.

Pre-Bulky Structures

In some0 embodiments, as test polynucleotide comprises a first pre-bulky structure (PB 1) on a first end that can form a first bulky structure (BS 1) under a first condition and a second pre-bulky structure (PB2) on a second end that can form a second bulky structure (BS2) under a second condition. In some embodiments, PB 1 comprises ss polynucleotide segments that can form BS 1 under the first condition. A first condition can be a first temperature T1, which can be about room temperature to 70° C., about 40° C. or higher, about 30° C. or higher, about 25° C. or higher, about 20° C. or higher, or about 15° C. or higher. In some embodiments, the first condition can be Ti and the presence of a first ligand that can bind to PB 1 to form BS 1. Examples of the first ligand include, without limitation, antisense oligonucleotide to PB 1, other compounds to facilitate formation of B S1 (e.g., compounds that can form a binding-pair with a ligand, wherein the ligand is attached to PB 1). Examples of such biding-pairs include, without limitation, antibody-antigen, and biotin-streptavidin system, and combinations thereof through covalent and/or noncovalent interactions, Wherein BS 1 is a pol, nucleotide 2-D or 3-D structure (e.g., duplex, hairpin structure, multi-hairpin structure and multi-arm structure), the melting temperature of I3SI (Tm1) is 15° C. or above, about 20° C. or above, about 25° C. or above, about 30° C. or above, about 35° C. or above, about 40° C. or above, or about 50° C. or above.

PB2 forms BS2 under a second condition. In some embodiments, PB2 is as polynucleotide segment that can form BS2 (e.g., polynucleotide duplex, hairpin structure, multi-hairpin structure and multi-arm structure) under the second condition. A second condition can be a second temperature 12, it is about −5 to about 50° C., about 40° C. or higher, about 30° C. or higher, about 25° C. or higher, about 20° C. or higher, about 15° C. or higher, about 10° C. or higher, or about 5° C. or higher. In some embodiments, T2 is about at least 5° C. lower, preferably at least about 10° C. lower or at least about 20° C. lower than T1. In some embodiments, the second condition can be T2 and the presence of a second ligand that can bind to PB2 to form BS2. Examples of the second ligand include, without limitation, anti sense oligonucleotide to PB2, other compounds to facilitate formation of BS2, (e.g., compounds that can form a binding-pair with a ligand, wherein the ligand is attached to PB2). Examples of such biding-pairs include, without limitation, antibody-antigen, and biotin-streptavidin system, and combinations thereof through covalent and/or noncovalent interactions. Wherein BS2 is a polynucleotide 2-D or 3-D structure (e.g., duplex, hairpin structure, multi-hairpin structure and multi-arm structure), the melting temperature of BS2 (Tm2) is about 5 to about 10° C., about 10 to about 20° C., about 20 to about 30° C., or about 20 to about 50° C.

In some embodiments. PB1 and/or PB2 comprise(s) structures that are non-binding to speed bumps in the speed bump pool. Examples of such structures include, without limitation, nucleotide analogs comprising non-binding bases such as IsodG, IsodC and abasic site.

Identifiers

In some embodiments, as test polynucleotide further comprise(s) functional moieties such as identifiers and isolation tags. In some embodiments, when the ss test polynucleotide is contacted with a random speed bump pool, identifier and isolation tags are constructed such that they will not be bound by the random speed bump pool. For example, an identifier segment can have isodG and isodC bases which preferably bind to each other. If speed bumps of the random speed bump pool do not have isodG or isodC base, speed bumps from the random speed bump pool will more preferably bind to sections of the ss test polynucleotide that is outside of the identifier segments. Thus, fewer electrical signals will be collected relating to the sequence information of the identifier, which makes the collected electrical signals easier to characterize.

Examples of identifiers include, without limitation, direction identifiers, reference signal identifiers, sample source identifiers and sample identifiers.

A ss test polynucleotide may have only one bulky structure on one end (e.g., FIG. 15), or two bulky structures on both ends (e.g., FIG. 17), One direction identifier may be positioned closely (e.g., 0, 1, 2, 3, 4, 5, 6, 7, 8, 9, 10, 11, 12, 13, 14, 15, 16, 17, 18, 19, 20, . . . or 50 bases) to each bulky structure in the ss test polynucleotide. The direction identifiers for different bulky structures can be the same or different.

When the ss test polynucleotide has two bulky structures and two direction identifiers, other identifiers can be positioned between the two direction identifiers. When the ss test polynucleotide has only one bulky structure on one end and one direction identifier, other identifiers can be positioned further away from the bulky structure compared to the direction identifier.

Other identifiers include, without limitation, reference signal identifier serves as a reference or calibration read to base line other electrical signals obtained in the same nanopore; sample source identifiers used to identify the source of the sample polynucleotide, and sample identifiers used to identify individual sample polynucleotides.

Figure 18:
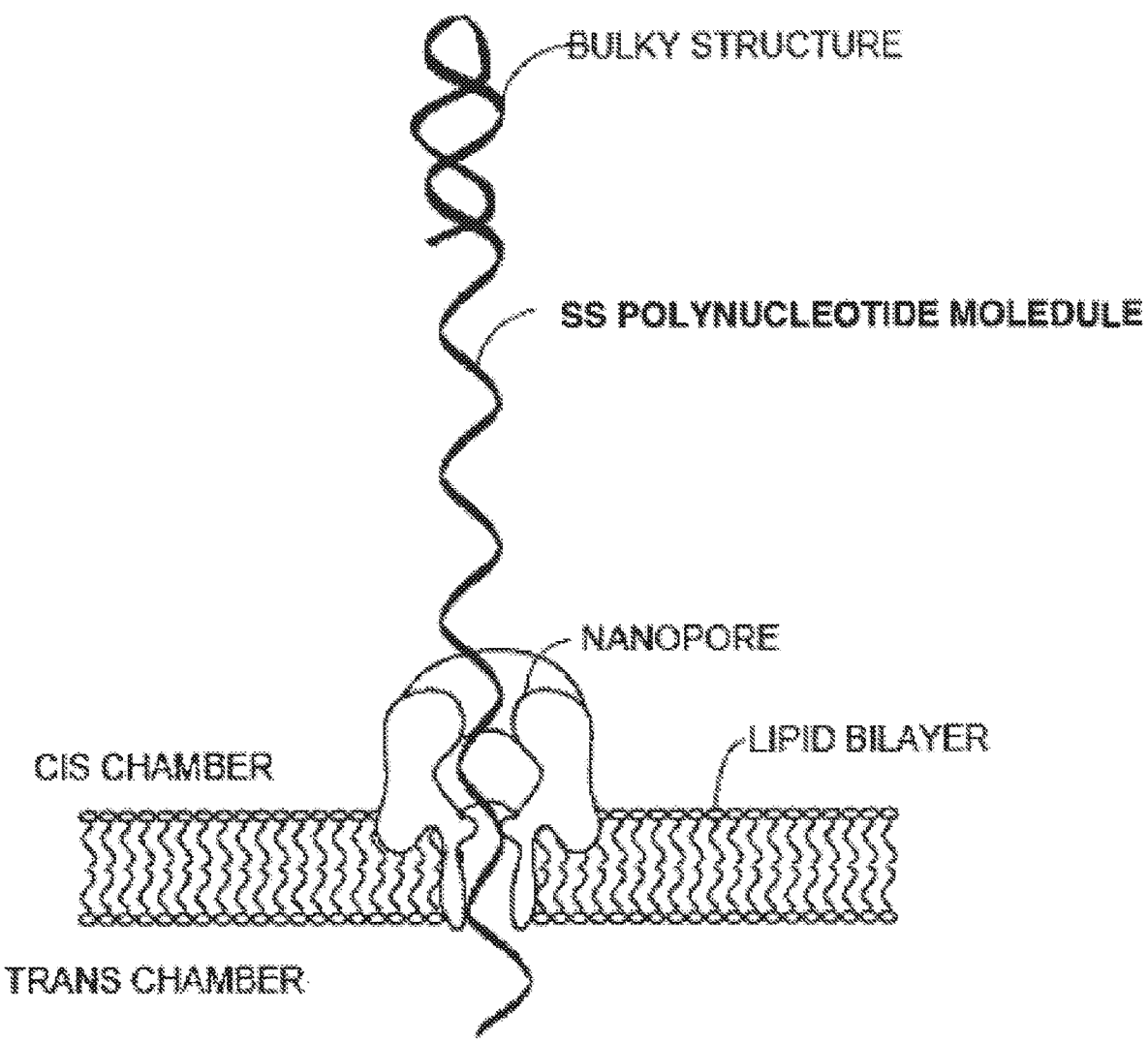
FIG. 18 illustrates detection of an identifier by an identifier-specific speed bump.

Because the structures of the identifiers are known, an identifier can be detected and/or identified by contacting an identifier-specific speed bump with the ss test polynucleotide. If the ss test polynucleotide comprises the identifier of interest, an identifier-specific speed bump duplex section will be formed, which will stall the ss test poly-nucleotide in the nanopore. A set of electrical signals may be obtained while the ss test polynucleotide is stalled in the nanopore, which can be used to indicate the formation of the speed bump-identifier duplex section (identifier, FIG. 18) and/or identify the sequence that is in front of the identifier-speed bump duplex and the first basepair of the identifier-speed bump duplex, in the flow direction of the as test polynucleotide molecule (shaded section, FIG. 18). FIG. 18 shows the situation in as test polynucleotide having only one bulky structure. The same method can be used when the ss test polynucleotide has bulky structures on both ends.

In some embodiments, the identifiers and/or identifier-specific speed bumps and/or the sequence in front of the identifier in the flow direction of the ss test polynucleotide molecule can comprise one or more nucleotides or structures that provide distinctive electrical signal that are readily identified. Examples of such nucleotides and structures include, without limitation, nucleotides comprising isodG or isodC, abasic nucleotides, methylated nucleotides, etc.

Isolation Tags

An isolation tag is a structure that can form a binding-pair with a ligand, wherein the ligand is further modified to facilitate concentration or isolation thereof. Examples of such biding-pairs include, without limitation, antibody-antigen, and the biotin-streptavidin system. Examples of further modifications to facilitate concentration or isolation include, without limitation, attachment of the ligand to a magnetic bead that can be readily concentrated and/or isolated.

In some embodiments, more than one functional moieties may overlap with each other or serve for more than one function.

Figure 19:
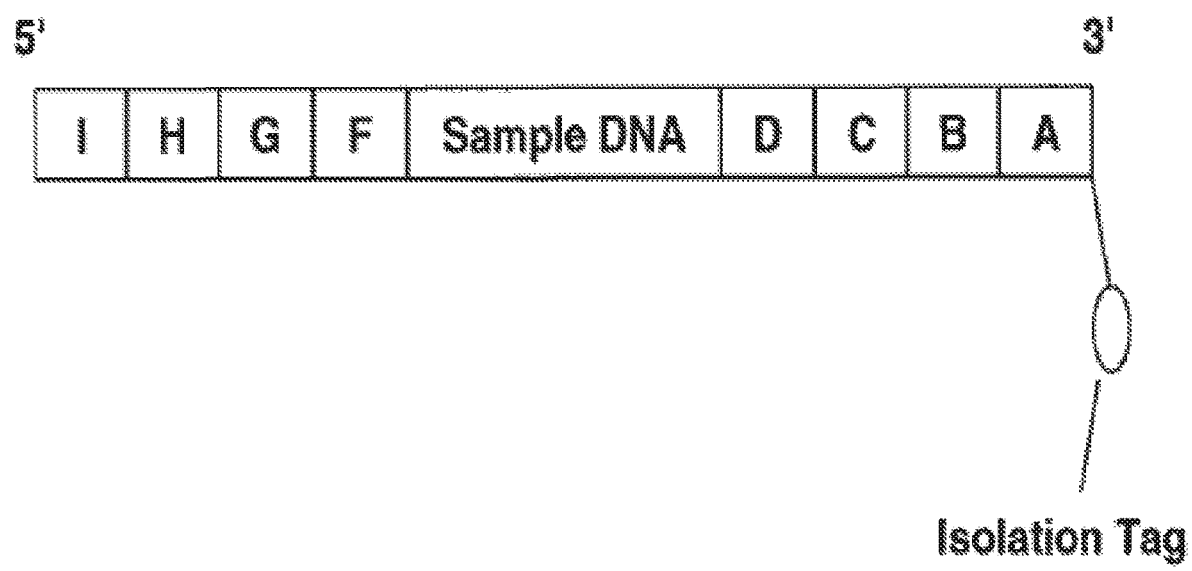
FIG. 19 illustrates an example of as test polynucleotide comprising a sample polynucleotide and multiple functional moieties.

An example of as test polynucleotide comprising multiple functional moieties (segments A, B, C, D, F, G, H, and I, FIG. 19) and a sample polynucleotide is shown in FIG. 19.

Segment I may serve as a pre-bulky structure and forms a bulky structure with a complementary strand thereof or by self-folding into a structure (e.g., polynucleotide hairpin structures, multi-hairpin structures and multi-arm structures), and segment H or a fragment thereof can serve as a direction identifier. Alternatively, segment I can form a hairpin with segment H under certain conditions. Thus, in this case, a pre-bulky structure is segments I and H. Segment G or a fragment thereof can serve as a direction identifier.

Segment F, G, and H, or a fragment thereof can be a reference signal identifier, a sample identifier, a sample source identifier. Alternatively, segments F, G and H together can be an identifier, or any fragment thereof can also serve as an identifier described herein. Similar situations apply to segments A, B, C and D on the 3' end. An Isolation Tag can be placed on the 3' end or on the 5' end, and it can be linked to the 3' terminal or 5' terminal nucleotide, or to any nucleotide on segments A, B, C, D, F, G, H and I, as long as it does not interfere with the binding of speed bump to the ss test polynucleotide, function of nanopore, or formation of bulky structure.

Construction of ss Test Polynucleotide Comprising Sample Polynucleotide and One or More Functional Moieties A test polynucleotide comprising sample polynucleotide and one or more functional moieties is constructed by ligating the sample polynucleotide with other segments as desired using conventional organic and/or biological methods.

The ss test polynucleotide shown in FIG. 19 can be formed by linking multiple functional moieties to a sample polynucleotide using conventional ligation methods (e.g., formation of covalent bonds (e.g., ligase assisted ligation or other covalent bonds, wherein the ligation can be accomplished by paired end sequencing chemistry, blunt-ended polynucleotide ligation, and/or sticky-end ligation) or non-covalent interactions).

Figure 20:
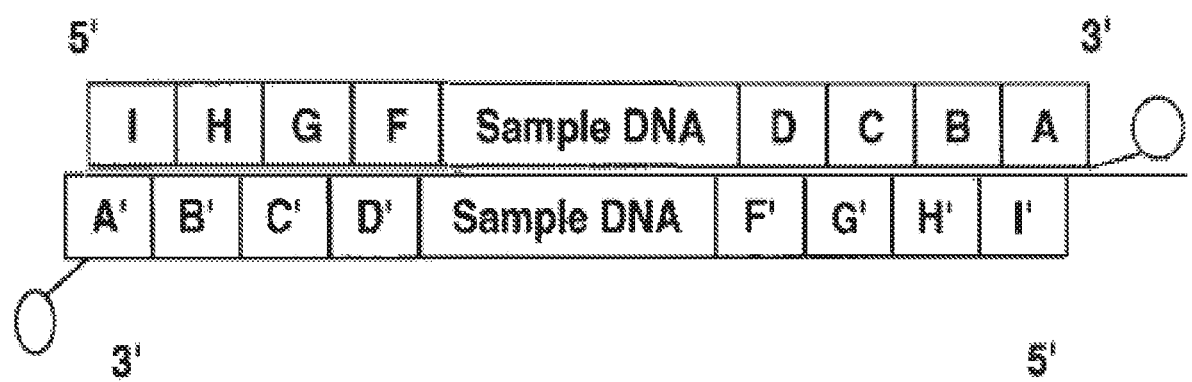
FIG. 20 illustrates an example of a ds test polynucleotide comprising a sample polynucleotide and multiple functional moieties.

In some embodiments, sample polynucleotide obtained is a double-stranded (ds) sample polynucleotide. The ds sample polynucleotide can be ligated with one or more ds functional moieties (e.g., ds PBI (Segments I&H-Segments A'&B', FIG. 20), ds PB2 (Segments B&A-Segments H'&I, FIG. 20), ds identifiers (e.g., (Segments G&F-Segments A'&B', and Segments D&C-Segments F'&G', FIG. 20), etc.) using conventional ligation methods (e.g., ligase assisted ligation following blunt end, dangling end, and/or linker ligation, mate-paired and end-paired protocols.) (FIG. 20). The functional moieties can be ligated to the sample polynucleotide all in one step, or sequentially, or all functional moieties on one end of the sample polynucleotide are constructed together first and then ligated to the end of the sample polynucleotide. Examples of the conventional ligation methods includes, without limitation, ligase assisted ligation following blunt end, dangling end, and/or linker ligation, paired end sequencing protocols, mate-paired and end-paired protocols. The obtained ds polynucleotide is then denatured to provide ss test polynucleotide using conventional methods (e.g., heated to denature the ds polynucleotide).

In some embodiments, the sample polynucleotide obtained is ads sample polynucleotide, and is linked to one or more ds functional moieties (e.g., ds PB 1, ds PB2, ds identifiers etc.) via covalent bonds other than the phosphodiester bonds. Examples of such linkage include, without limitation, the linkage in glycol nucleotides, morpholines, and locked nucleotides.

In some embodiments, the sample polynucleotide obtained is as sample polynucleotide (DNA or RNA), and its complementary strand (DNA or RNA) can be created to anneal with the ss sample polynucleotide to form ads sample polynucleotide (ds DNA, ds RNA or DNA-RNA hybrid) using conventional methods, and then ligate to one or more ds functional moieties as described herein.

In some embodiments, as sample polynucleotide is linked to one or more ss functional moieties (e.g., ss PB1, ss PB2, ss identifiers etc.) using ligase assisted ligation. In some embodiments, a ss sample polynucleotide is linked to one or more ss functional moieties via covalent bonds other than the phosphodiester bonds. Examples of such linkage include, without limitation, the linkage in glycol nucleotides, morpholinos, and locked nucleotides.

In some embodiments, the sample polynucleotide obtained is ads sample polynucleotide and can be denatured to provide a ss sample polynucleotide to be linked to one or more ss functional moieties as described herein.

In some embodiments, the functional moieties are linked by cleavable bonds such that one or more individual functional moieties can be cleaved from the ss test polynucleotide. In an embodiment, a bulky structure can be removed from a ss test polynucleotide by cleaving a functional moieties positioned between the sample polynucleotide and the bulky structure. Then, the ss test polynucleotide can be released from the nanopore it is in by applying an electric potential to move the ss test polynucleotide through the nanopore in the direction at which it is no longer stalled, slowed or stopped by the cleaved bulky structure.

In some embodiments, desired functional moieties are linked at a desired end (3' or 5') of the sample polynucleotide, such that the test polynucleotide obtained thereof can be threaded into the nanopore at a desired direction (e.g., from 3' end or from 5' end).

Identification of a Sample Polynucleotide Using a Random Speed Bump Pool

One aspect of the disclosure relates to a method of identifying a sample polynucleotide sequence comprising:
(A1) providing a double-stranded (ds) sample polynucleotide;
(A2) ligating a first pre-bulky (PBI) structure to a first end of the ds sample polynucleotide, and ligating a second pre-bulky (PB2) structure to a second end of the ds sample polynucleotide,
(A3) denaturing the ds sample polynucleotide of A2 to as test poly-nucleotide,
(B1) forming a first bulky structure (BSI) from PBI on the first end of the ss test polynucleotide at a first temperature,
(B2) applying a first electric potential to flow the ss test polynucleotide through a nanopore,
(B3) forming a second bulky structure (BS2) from PB2 on the second end of the ss test polynucleotide at a second temperature,
(B4) optionally applying another electric potential to reverse the flow of the ss test polynucleotide until the ss test polynucleotide is stalled, slowed or stopped by BS2 before the constriction area of the nanopore,
(B5) contacting a random speed bump pool with the ss test polynucleotide to form a speed bump-ss test polynucleotide complex having at least one speed bump-ss test polynucleotide duplex segment at a working temperature,
(B6) applying a third electric potential to flow the speed bump-ss test polynucleotide complex through the nanopore until a first speed bump-ss test polynucleotide duplex segment is stalled, slowed or stopped before the constriction area of the nanopore,
(B7) obtaining a first set of electrical signals when the first speed bump-ss test polynucleotide duplex segment is stalled inside the nanopore for a dwelling time, and characterizing the nucleotide sequence that is in front of the first speed bump-ss test polynucleotide duplex segment and the first basepair of the first speed bump-ss test polynucleotide duplex segment, in the flow direction of the ss polynucleotide,
(B8) dissociating the first speed bump-ss test polynucleotide duplex segment and continuing the flow of the ss polynucleotide through the nanopore, and
(B9) repeating steps (B4) to (B8) until the ss test polynucleotide is stalled, slowed or stopped by BS 1 or BS2.

In an embodiment, the ss polynucleotide is as test polynucleotide comprising a sample polynucleotide as described herein. Speed bumps comprise one or more nucleotides as defined herein.

In some embodiments, the ss sample polynucleotide comprises a DNA oligonucleotide, a RNA oligonucleotide, or a combination thereof. In some embodiments. The ds sample polynucleotide can bead s DNA, ds RNA or a DNA-RNA hybrid.

A random speed bump pool comprises a collection of speed bumps of a given length that can bind to all sections of the ss test polynucleotide or a fragment thereof (e.g., a sample polynucleotide). Such a given length can be 2, 3, 4, 5, 6, 7, 8, 9, 10, 11, 12, 13, 14, 15, or 16, preferred 10 or less, 8 or less, 6 or less and 4 or less. In an embodiment, the random speed bump pool comprise speed bumps composed of one or more nucleotides selected from the group consisting of universal nucleotides, locked nucleotides, primary nucleotides, modifications thereof, and combinations thereof. Modifications of universal nucleotides, and primary nucleotides include modifications at the nucleobase structures, the backbone structures (e.g., glycol nucleotides, morpholines, and locked nucleotides) and combinations thereof. In an embodiment, the random speed bump pool comprises oligonucleotides having universal nucleobases which base-pair with all primary nucleobases (A, T, C, G, and U). In another embodiment, the random speed bump pool comprises oligonucleotides having all possible combinations of primary nucleobases. In another embodiment, the random speed bump pool comprises oligonucleotides having all possible combinations of primary nucleobases and universal nucleobases. In another embodiment, the random speed bump pool comprises oligonucleotides having universal nucleotides at designated positions and all combinations of primary nucleobases at the other positions. In another embodiment, the backbone structures of the speed bumps in the random speed bump pool are modified (e.g., glycol nucleotides, morpholinos, and locked nucleotides) at designated position(s), random positions or combinations thereof. In another embodiment, the speed bumps in the random speed bump pool comprise DNA oligonucleotides, RNA oligonucleotdies, or combinations thereof.

The speed bumps may comprise universal nucleobases at designated positions and random primary nucleobases at other positions to lower the total number of possible combinations of primary nucleobases. For example, for a random speed bump pool having IO-base oligonucleotides, the total amount of combinations of the primary nucleobases is $4^{10}=1,048,576$. However, if 4 positions of the IO-base nucleotide are designated to have universal nucleobases only, the total amount of combinations of the primary nucleobases is $4^6=4,096$, which is significantly lower.

In some embodiments, because the first base pair of the speed bump-test polynucleotide duplex segment may be partially or completely in the nanopore and influence the electrical signals obtained, it is preferred to construct the speed bumps to have a universal nucleotide at the 5' and/or 3' end to normalize the contribution of the first base pair of the speed bump-test polynucleotide duplex segment and makes the signals easier to analyze.

In some embodiments, the concentrations of one or more speed bumps of a random speed bump pool may be further adjusted to as desired. For example, the concentrations may be about the same for each type of speed bump, and be adjusted such that sufficient ss speed bumps exist to contact the as test polynucleotide. .1n. an embodiment, because polyG strands bind strongly to polyC strands, polyG and polyC speed bumps will have higher concentrations than speed bumps having other sequences to provide sufficient as polyG and ss polyC to contact the ss test polynucleotide. In another embodiment, the concentrations of speed bumps and/or nucleotides used to make the speed bumps are adjusted such that each speed bump has about the same affinity to form speed bump-test polynucleotide complex, and no specific speed bumps are significantly more favored than others. In some embodiments, the concentrations of speed bumps and/or nucleotides used to make the speed bumps are adjusted such that one or more specific speed bumps are significantly more favored than others. For example, the speed bump pool can be constructed to be substantially free of speed. bumps that can bind to known segments in the ss test polynucleotide. Therefore, new sequence information obtained will be about the unknown segments and not the known segments in the ss test polynucleotide.

In some embodiments, step (B5) forms a speed bump-test polynucleotide complex having at least one speed bump-test polynucleotide duplex segment, wherein the speed bump forms a duplex with the ss test polynucleotide segment that is up to 1, 2, 3, 4, 5, 6, 7, 8, 9, 10, 11, 12, 13, 14, 15, or 16 basepairs, and is threaded in the nanopore at a first working condition. A working condition includes parameters such as a working temperature (Tw), exposure time, concentration of speed bump and ss test polynucleotide, pH, salt concentration, and other additives and concentration thereof that can affect the formation of speed bump-test polynucleotide complex. TW can be about −10 to about 25° C., about −10 to about 0° C., about −10 to about 15° C., about −10 to about 10° C., about −10 to about 5° C., about −10 to about 0° C., about −10 to about −5° C., about −5 to about 25° C., about −5 to about 20° C. about −5 to about 15° C., about −5 to about 10° C., about −5 to about 5° C., or about −5 to about 0° C., to allow association of relatively short speed bumps (2, 3, 4, 5, 6, 7, 8, 9, 10, 11, 12, 13, 14, 15, or 16 bases) to the ss test polynucleotide. In an embodiment, at Tw is about at least 10° C. lower, preferably at least about 20° C. lower than T2. In another embodiment, at Tw, at least about 50% of PBI and PB2 are in the forms of BS I and BS2, respectively. In another embodiment, at Tw, at least about 70% of PBI and PB2 are in the forms of BS I and BS2, respectively. In another embodiment, at Tw, at least about 90% of PBI and PB2 are in the forms of BSI and BS2, respectively.

Exposure time of ss test polynucleotide to speed bumps is about 1 ns or longer, about 10 ns or longer, about 1 µs or longer, about 10 µs or longer, about 1 ms or longer, about 10 ms or longer, about 1 s or longer, or about 5 s or longer to allow sufficient speed bump-test polynucleotide complex to form. Concentrations of the speed bumps are preferably about 100,000 times, 10,000 times, 1,000 times, 300 times, about 200 times, about 100 times, about 50 times, about 20 times of the concentration of the ss test poly 0.1cleotide, or the concentration of the speed bumps is about the same as that of the as test polynucleotide. The concentrations of the speed bumps are preferably about 1 mM to about 100 mM, about 1 nM to about 10 mM, about 1 mM to about 1 mM, about 10 nM to about 100 mM, about 10 nM to about 10 mM, about 10 nM to about 1 mM, about 1 mM to about 10 mM, or about 10 mM to about 100 mM. The concentration of ss test polynucleotide is about 1 mM to about 100 mM, about 1 nM to about 10 mM, about 1 mM to about 1 mM, about 10 nM to about 100 mM, about 10 nM to about 10 mM, or about 10 nM to about 1 mM. pH is preferably about 6 to about 8, or about 7. Salt (e.g., KCl, NaCl, phosphate) concentration is about 1 mM to about 10 M, about 1 mM to about 1 M about 10 mM to about 10 M, about 10 mM to about 1 M, about 100 mM to about 10 M, or about 100 mM to about 1 M. Other additives that may affect the formation of speed bump-test polynucleotide complex include, without limitation, dextran sulfate and glycerol. Their concentrations may be adjusted to optimize formation of speed bump-test polynucleotide complex.

A working condition further comprises an electric potential of about OmV to about 320 mV at a desired polarity. The working condition can be continuously adjusted through the process based on the characteristics of the speed bump binding (e.g., length, nucleotide components, and binding affinity), the nanopore characteristics and the ss test polynucleotide property (e.g., GC content or secondary structure thereof), to optimize the signal quality. Thus, the electric potential can continuously change from for example, −320 mV to +320 mV.

Steps (B4) to (B9) can be carried out at a first working condition as described herein. In some embodiments, the electric potential applied to each step of steps (B4) to (B9) may be the same or different or continuously changing. In some embodiments, the electric potential for step (B8) may be adjusted to facilitate the dissociation of the speed bump-test polynucleotide duplex segment. In some embodiments, the electric potential for step (B8) may be applied to move the ss test polynucleotide at a reversed direction compared to the ss test polynucleotide flow direction in step (B6) (forward direction) to move the speed bump-test polynucleotide duplex segment from the constriction area of the nanopore before applying another electric potential to move the polynucleotide at the forward direction to dissociate the speed bump-test polynucleotide duplex segment.

A dwelling time is provided for a polynucleotide duplex segment to stall inside the nanopore so that a nanopore detector can collect and read relevant sequence information. The dwelling time typically depends on the nanopore detector and the working condition. In some embodiments, the dwelling time is at least about 10 µs, at least about 1 ms, at least about 10 ms, at least about 200 ms, at least about 500 ms, at least about 1 s, at least about 2 s, or at about least 5 s. Generally, the longer the dwelling time is, the better the signal quality, and the more sequence information can be obtained.

A sequence of a small number of bases (less than 20 bases) anywhere within up to 100 bases (preferably up to 50 bases) in front of the stopping point can be read at one time when a polynucleotide duplex segment is stalled inside the nanopore for a dwelling time. Preferably, less than 5 or 6 bases are read at a time. For example, 1, 2, 3, 4, or 5 bases are read at a time within a larger polynucleotide sequence up to 50 bases at any nucleotide position 1-50 (e.g., at position 1, 2, 3, 4, 5, 6, 7, 8, 9, 10, 11, 12, 13, 14, 15, 16, 17, 18, 19, 20, . . . 50 from the speed bump-ss test polynucleotide duplex segment).

As shown in FIG. 12, as test polynucleotide comprising bulky structures formed on both ends is locked in a nanopore (steps (B1) to (B4)) and forms speed bump-test polynucleotide complex with multiple speed bumps (step (B5)).

A set of electrical signals of the ss test polynucleotide may be obtained each time the ss test polynucleotide is stalled by a speed bump-test polynucleotide duplex segment in the nanopore for a dwelling time, and then the speed bump-test polynucleotide duplex segment dissociates and the as test polynucleotide moves forward until stalled by the next speed bump-test polynucleotide duplex segment (in FIG. 12, the ss test polynucleotide is illustrated to move from cis side to trans side). This stall-detect-disassociate-stall process is repeated until the ss test polynucleotide is stalled, slowed or stopped by the bulky structure of one end. An example of electrical signals obtained is shown in FIG. 16.

Figure 13:
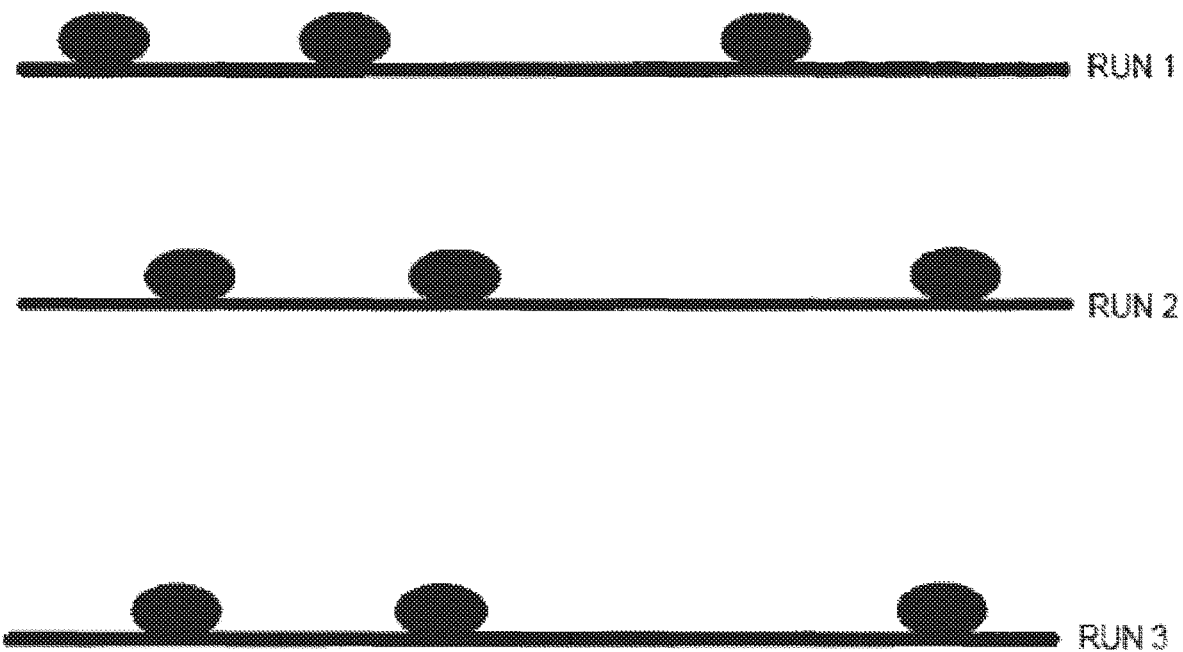
FIG. 13 illustrates different binding patterns achieved by contacting a ss test polynucleotide with a random speed bump pool.

In some embodiments, a random speed bump pool is present mainly on one side of the nanopore (e.g., Cis side as shown in FIG. 13), and the method further comprising:
(BIO) applying another electric potential to move the ss test polynucleotide at a reversed direction of the ss test polynucleotide flow in step (B5) until the ss test polynucleotide is stalled, slowed or stopped by the other bulky structure before the constriction area of the nanopore,
(B1 I) repeating steps (B4) to (BIO) at least 1 time, at least 5 times, at least 10 times, at least 15 time, at least 20 time, at least 25 times, at least 30 times, at least 50 times, or at least 100 times and
(B12) constructing the ss test polynucleotide sequence by overlapping the collected nucleotide sequence information.

Step (BIO) can be carried out under a working condition described herein. The electric potential applied can be at a reduced value or a reverse polarity compared to the electric potential applied in step (B4) to (B9) to reverse the flow of the test polynucleotide. The electric potential applied in each step can be the same or different or continuously changing.

Figure 21:
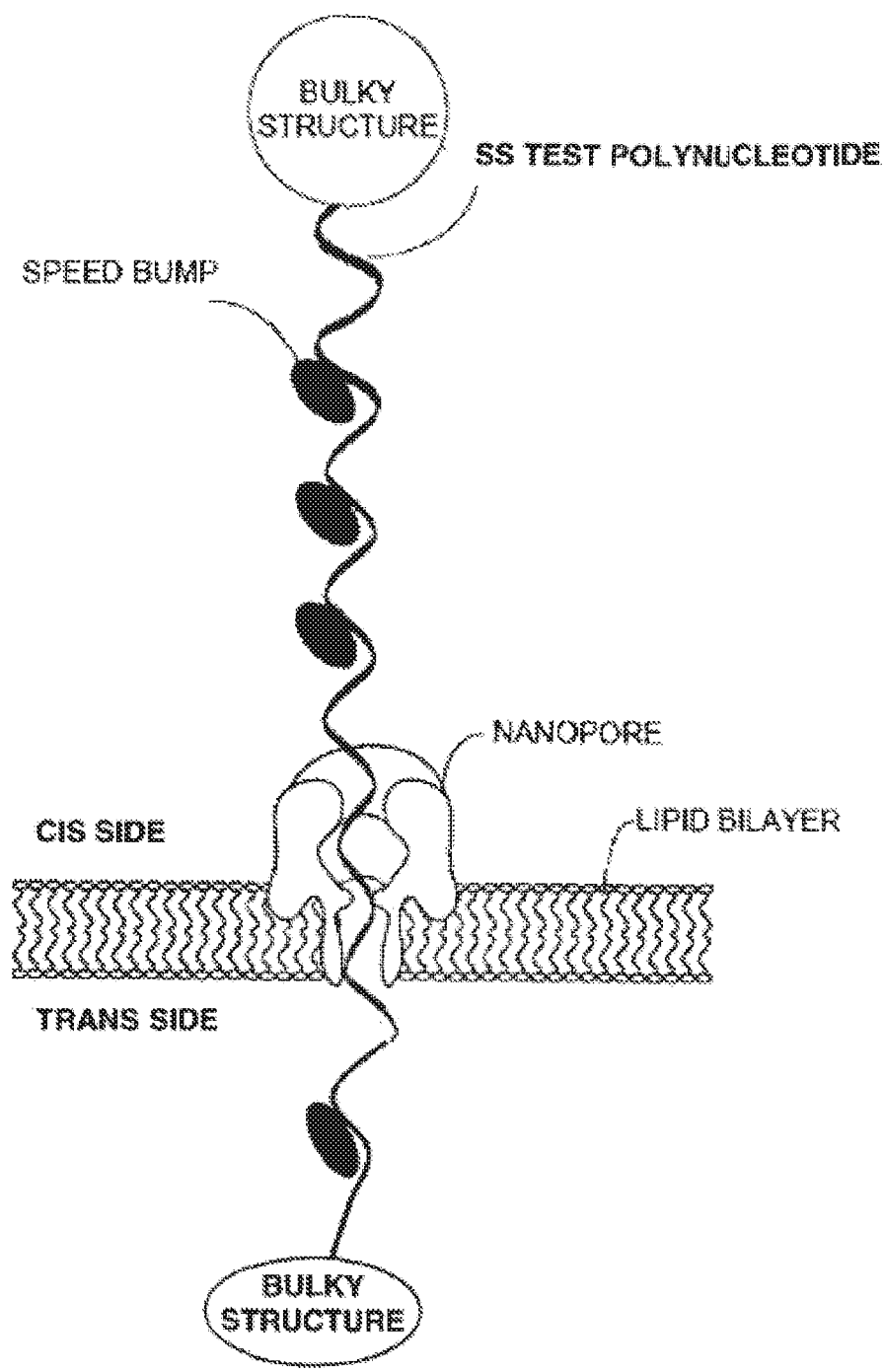
FIG. 21 illustrates as test polynucleotide trapped in a nanopore bound with multiple speed bumps on both sides of the nanopore.

In some embodiments, a random speed bump pool is present in both sides of the nanopore and speed bumps bind to the ss test polynucleotide at the segment exposed to the speed bump pool in both sides of the nanopore (Cis and Trans sides as shown in FIG. 21). The method of identifying a nucleotide sequence of a sample polynucleotide in a as test polynucleotide described herein further comprising:
(1) repeating steps (B4) to (B8) under a second working condition until the ss test polynucleotide is stalled, slowed or stopped by the other bulky structure before the constriction area of the nanopore;
(2) repeating steps (B9) and (1) at least 1 time, at least 5 times, at least 10 times, at least 15 time, at least 20 times, at least 25 times, at least 30 times, at least 50 times, or at least 100 times, and
(3) constructing the nucleic acid sequence of the sample polynucleotide by overlapping the collected nucleotide sequence information.

The second working condition can be a working condition as described herein. The second working condition can have the same or different parameters compared to the first working condition. The electric potential applied in step (1) can be at a reduced value or a reverse polarity compared to the electric potential applied in step (B9). The electric potential applied in each step can be the same as applied in the earlier step, or different compared to the earlier step, or continuously changing.

Figure 14:
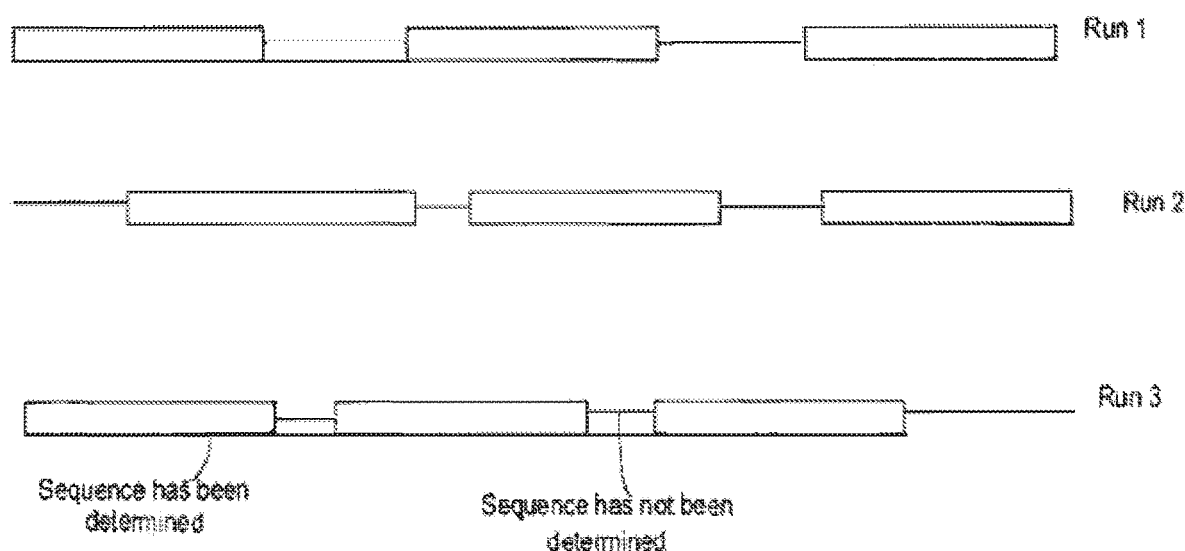
FIG. 14 illustrates different sequence information patterns achieved by randomly stalling as test polynucleotide in a nanopore to obtain sequence information.

Because a random speed bump pool comprises speed bumps that can bind to random sections of the ss test polynucleotide, each time when the ss test polynucleotide goes from one end stalled, slowed or stopped by BS 1/BS2 to the other end according to the process described herein, speed bumps may bind to different combinations of ss test polynucleotide duplex segments (FIG. 13), and can provide sequence information of different segments in the ss test polynucleotide (FIG. 14). Thus, when step (B8) and/or step (B9) are/is repeated such that sequence information of each and every nucleotide of the sample polynucleotide in the ss test polynucleotide has been obtained, the sample polynucleotide can be constructed by overlapping the collected nucleotide sequence information.

Figure 22:
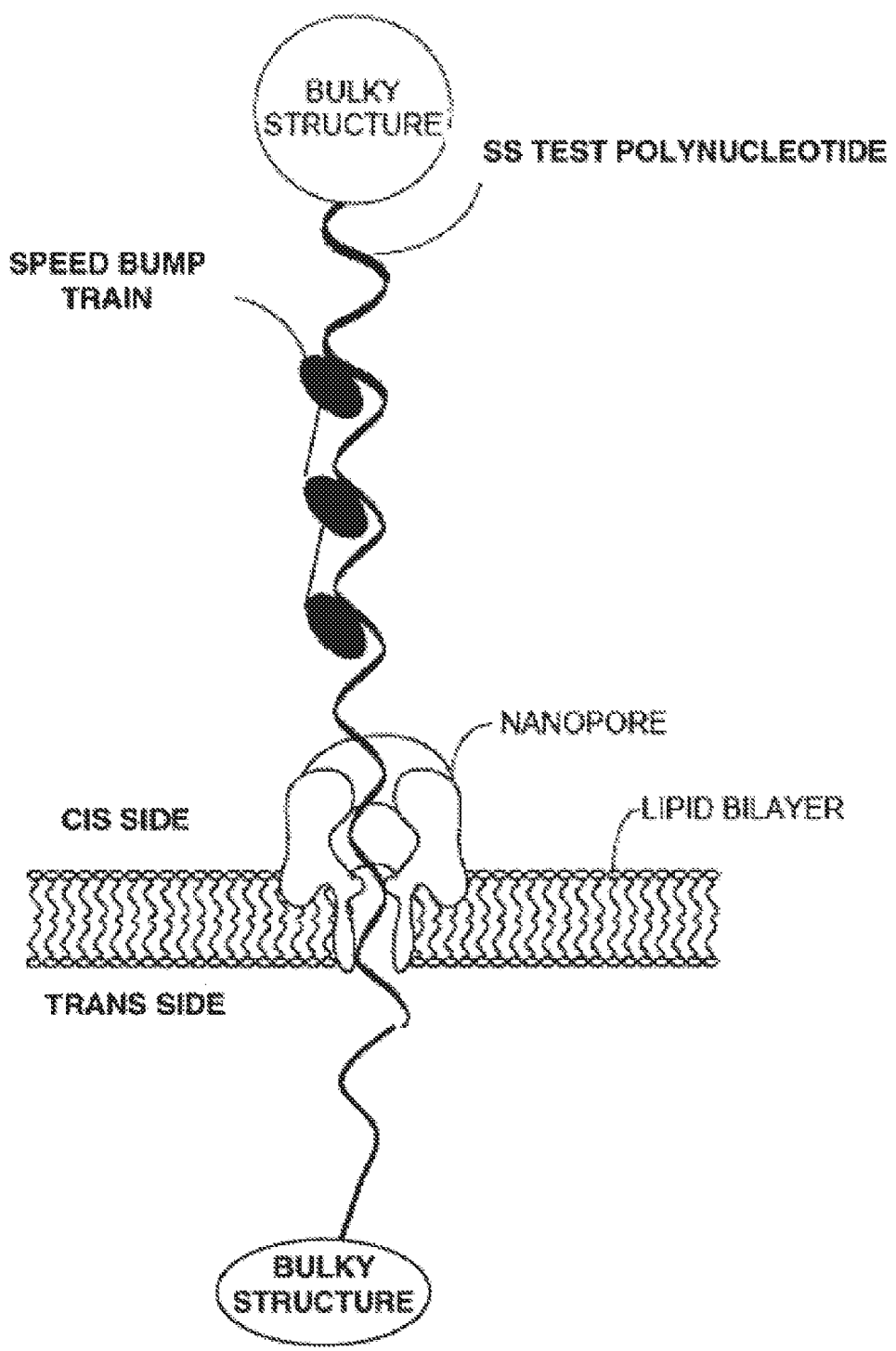
FIG. 22 illustrates contacting as test polynucleotide with a speed bump train.

In some embodiments, more than one speed bump is linked by a non-biding linker (e.g. abasic oligonucleotide) to form speed bump train (FIG. 22) such that the dissociation of each speed bump-test polynucleotide duplex segment will not cause the dissociation of the whole speed bump train from the ss test polynucleotide. In some embodiments, the non-binding linker is designed to be spaced by about 1 base, about 2 bases, about 3 bases, about 4 bases or about 5 bases. Thus, the gap between known segments shown in FIG. 14 will be more likely to be the same as the length of the linker (e.g., about 1 base, about 2 bases, about 3 bases, about 4 bases or about 5 bases). It will be easier to construct the nucleic acid sequence of the sample polynucleotide in this case.

In some embodiments, step (B2) further comprises:
(B2a) Obtaining a set of electrical signals when the first bulky structure is stalled inside the nanopore, and characterizing the nucleotide sequence that is in front of the first bulky structure and the first basepair of the first bulky structure, in the flow direction of the ss test polynucleotide, and step (B3) further comprises:
(B3a) obtaining another set of electrical signals when the second bulky structure is stalled inside the nanopore, and characterizing the nucleotide sequence that is in front of the second bulky structure and the first basepair of the second bulky structure, in the flow direction of the ss test polynucleotide.

Figure 23:
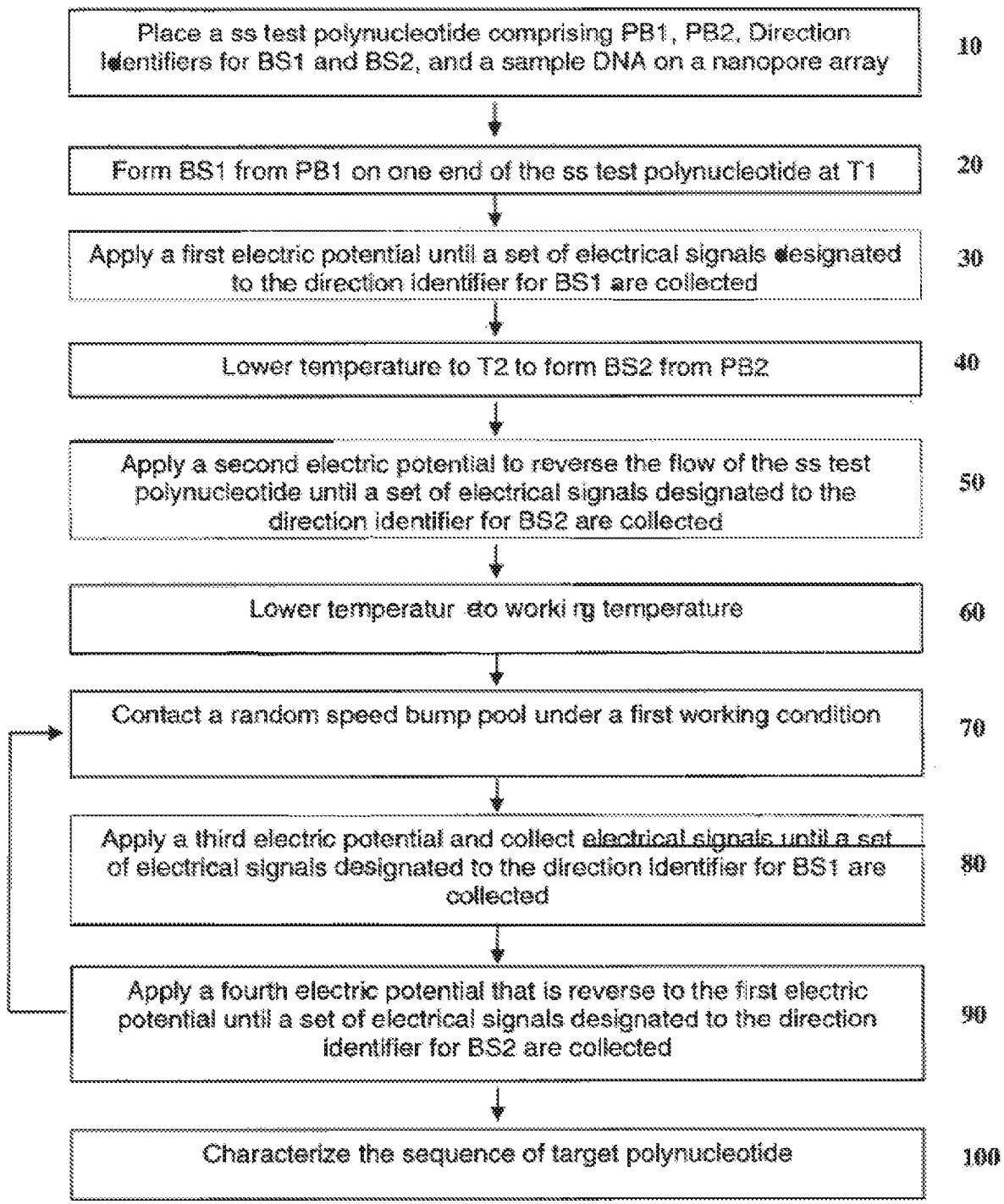
FIG. 23 illustrates a flowchart of a process according to an embodiment of the present disclosure.

In an embodiment, a method as described herein is carried out according to a flowchart shown in FIG. 23. as test polynucleotide comprising PBI, PB2, DII, D12 and a sample polynucleotide has been constructed and placed on nanopore array (Block 10, FIG. 23). Then BSI is formed from PBI on one end of the ss test polynucleotide at T1 (Block 20, FIG. 23). A first electric potential is applied to thread the ss test polynucleotide through a nanopore until the ss test polynucleotide is stalled, slowed or stopped by BS I wherein a set of electrical signals characterizing DII are collected (Block 30, FIG. 23). The temperature is then lowered to T2 to form BS2 from PB2 (Block 40, FIG. 23). A second electric potential that is lower than the first electric potential or opposite in polarity to the first electric potential is applied until the ss test polynucleotide is stalled, slowed or stopped by BS2 wherein a set of electrical signals characterizing D12 are collected (Block 50, FIG. 23). The temperature is further lowered to Tw (Block 60, FIG. 23), then contact a random speed bump pool with the ss test polynucleotide under a first working condition as described herein to form randomly bound speed bump-test polynucleotide complex (Block 70, FIG. 23). A third electric potential is applied, moving the speed bump-test polynucleotide complex through the nanopore until the ss test polynucleotide is stalled by a first speed bump-test polynucleotide duplex segment. The ss test polynucleotide is stalled for a dwelling time during which a set of electrical signals are obtained, which will be used to characterize the sequence in front of the first speed bump-test polynucleotide duplex segment and the first base pair of the speed bump-test polynucleotide duplex segment in the flow direction of the ss test polynucleotide. Then the first speed bump-test polynucleotide duplex segment is dissociated and the ss test polynucleotide continues through the nanopore until stalled, slowed or stopped by the next speed bump-test polynucleotide duplex segment or BS 1. A set of electrical signals designated to DI1 are collected when the ss test polynucleotide is stalled, slowed or stopped by BS 1 in the nanopore (Block 80, FIG. 23). Then a fourth electric potential that is at a reduced value or a reverse polarity to the third electric potential is applied until the ss test polynucleotide is stalled, slowed or stopped by BS2 wherein a set of electrical signals characterizing DI2 are collected (Block 90, FIG. 23). Then the steps in Blocks 70 to 90 are repeated until sufficient sequence information has been collected to characterize the sequence of the sample polynucleotide.

Detection of an Identifier and Identification of an Identifier in a Test Polynucleotide Molecule Another aspect of the disclosure relates to a method of obtaining sequence information of as test polynucleotide molecule as described herein. The method comprises:

(B1) forming a first bulky structure on a first end of the test polynucleotide molecule, (C1) contacting a pool of speed bumps (speed bump pool) with the test polynucleotide molecule to form a speed bump-test polynucleotide molecule complex having at least one speed bump-test polynucleotide molecule segment, (C2) applying an electric potential to flow the speed bump-test polynucleotide molecule complex through a nanopore until a first speed bump-test pol, nucleotide molecule segment is stalled before the constriction area of the nanopore, (C3) obtaining a first set of electrical signals when the first speed bump-test polynucleotide molecule segment is stalled inside the nanopore for a dwelling time, in the flow direction of the test polynucleotide molecule, (C4) dissociating the first speed bump-test polynucleotide molecule segment and continuing the flow of the molecule through the nanopore, and (C5) repeating steps (C1) to (C4) until the test polynucleotide molecule is stalled, slowed or stopped by BS 1.

In an embodiment, the test polynucleotide molecule is as test polynucleotide comprising one or more nucleotides as described herein, and the speed bumps comprise one or more nucleotides as described herein. The ss test polynucleotide comprises PBI as described herein.

In some embodiments, step (C1) forms a speed bump-test polynucleotide complex having at least one speed bump-test polynucleotide duplex segment, wherein the speed bump forms a duplex with the test polynucleotide duplex segment that is up to 1, 3, 4, 5, 6, 7, 8, 9, 10, 11, 12, 13, 14, 15, or 16 basepairs.

Steps (C1) to (C5) can be carried out at a working condition as described herein.

A dwelling time for a nanopore detector to collect relevant sequence information is the same as described herein.

Methods described herein may be used to detect an identifier exists in the ss test polynucleotide. An identifier can serve as e.g., direction identifier (e.g., verifying the formation of BS 1 and showing the ss test polynucleotide has reached to the end having BS 1), reference signal identifier (a reference or calibration read to base line other electrical signals obtained in the same nanopore), sample source identifier (identifying the source of the test polynucleotide), or sample identifier for the test polynucleotide (identifying the test polynucleotide). In some embodiments, a speed bump pool comprises a first speed bump (FIG. 15) which can bind to a first identifier (identifier 1 in FIG. 15), and is substantially free of other speed bumps that can bind to the ss test polynucleotide (preferably less than 10%, more preferably less than 5%, and most preferably less than 1%). When a ss test polynucleotide comprising identifier 1 contacts the first speed bump, a first speed bump-identifier 1 duplex segment is formed to form a first speed bump-test polynucleotide complex. In the presence of an appropriate electrical field, the first speed bump-test polynucleotide complex goes through a nanopore until stalled by the first speed bump-identifier 1 duplex segment. The nanopore detector obtains a first set of electrical signals. Then the first speed bump-test polynucleotide complex dissociates and the ss test polynucleotide goes through the nanopore until stalled, slowed or stopped by BSI at the first end (i.e., in step (C4), the ss test polynucleotide flow through the nanopore smoothly until stalled, slowed or stopped by BS 1 without being stalled again in the nanopore). The nanopore detector will obtain another set of electrical signals when the ss test polynucleotide is stalled, slowed or stopped by the BS 1 structure. Thus, compared to a ss test polynucleotide that does not comprise identifier 1 sequence, the ss test polynucleotide that comprises identifier 1 sequence provides two sets of electrical signals showing that it is stalled twice in the nanopore, while the ss test polynucleotide that does not comprise identifier 1 sequence provides one set of electrical signals showing it is stalled once in the nanopore (by BS 1).

In another embodiment, the ss test polynucleotide and/or the speed bumps can be constructed such that the first set of electrical signal obtained in step (C3) is distinctive from a set of electrical signals obtained when a primary nucleotide sequence is detected by the nanopore. For example, the known identifier sequence can comprise one or more nucleotide analogs having isodG and/or IsodC. In front of this identifier sequence is a known reading sequence that would be in the constriction zone of a pore if a speed bump was hybridized to the identifier sequence and stalled, slowed or stopped in the pore. The reading sequence could comprise IsodC, IsodG and/or abasic positions that do not bind to natural nucleotides. Additionally, both the identifier sequence and the specific antisense speed bump sequence to the identifier would contain appropriate IsodG and IsodC so that only the specific speed bump to the identifier would hybridize to that location. Natural nucleotide speed bumps would not interfere or bind to the IsodG IsodC-containing identifier sequence and natural nucleotide speed bumps would not interfere with the reading sequence. The resulting identification of the strand in the pore would occur independent of the presence of other natural or man-made nucleotide speed bumps. In this case, the speed bump pool does not have to be substantially free of other speed bumps that can form complex with the ss test polynucleotide. When another speed bump binds to a segment of the ss test polynucleotide other than identifier 1 segment, the first set of electrical signal obtained while the first speed bump-test polynucleotide duplex segment is stalled in the nanopore is distinctive from the other set of electrical signal obtained while the other speed bump-test polynucleotide duplex segments are stalled in the nanopore. Thus, the presence of other speed bumps that can form complex with the ss test polynucleotide does not interfere with the detection of the distinctive signals generated from binding of the first speed bump with identifier 1 of the ss test polynucleotide. The ss test polynucleotide and/or the speed bumps can be further constructed such that no other speed bumps binds to the identifier 1 segment as described herein. Thus, other speed bumps that do not comprise isodG or isodC bases will not bind to the identifier 1 segment.

In another embodiment, the ss test polynucleotide comprises more than one identifier, and the ss test polynucleotide and/or the speed bumps (SBN, N=1, 2, ... ) that bind to the identifier segments (identifier N) respectively are designed such that when each SBN-identifier N duplex segment is stalled in the nanopore, the set of electrical signal obtained from the nanopore is distinctive from a primary nucleotide sequence and from when other SBN-identifier N duplex segment is stalled in the nanopore. The speed bump pool comprises the speed bumps specific for the identifier(s) that is (are) to be detected, and optionally include speed bumps for other identifiers and/or other speed bumps that can bind to the ss test polynucleotide.

In another embodiment, the identifier that binds to the identifier-specific speed bump and the sequence in front of the identifier in the flow direction of the ss test polynucleotide are both known. Thus, the set of electrical signals obtained in step C3 can also be used to identify the sequence in front of the identifier in the flow direction of the ss test polynucleotide, which can in turn be used to identify of the identifier.

In another embodiment, the method further comprises applying a first electric potential to flow the ss test polynucleotide through a nanopore, and forming a second bulky structure (BS2) on a second end of the ss test polynucleotide under a second condition as described herein. In an embodiment, the temperature of the first condition (T1) is higher than the temperature of the second condition (T2), which is higher than the working temperature Tw. In an embodiment, the temperature of the first condition (T1) is at least 10° C. higher or at least 20° C. higher than the temperature of the second condition (T2), which is at least about 1° C. higher, at least about 5° C. higher, at least about 10° C. higher, at least about 15° C. higher, at least about 20° C. higher, or at least about 25° C. higher than the working temperature TW.

Extending the sequence of the known speed bump in the flow direction of the ss test polynucleotide allows identification of longer sequences in the sample polynucleotide. This method may comprise the following steps:
(E1) contacting a first known speed bump with the test polynucleotide molecule to form a first known speed bump-test polynucleotide molecule complex having a first known speed bump-test polynucleotide molecule segment,
(E2) applying an electric potential to flow the first known speed bump-test polynucleotide molecule complex through a nanopore until the first known speed bump-test polynucleotide molecule segment is stalled before the constriction area of the nanopore,
(E3) obtaining a first set of electrical signals when the first known speed bump-test polynucleotide molecule segment is stalled inside the nanopore for a dwelling time, in the flow direction of the test polynucleotide molecule,
(E4) dissociating the first known speed bump-test polynucleotide molecule segment and continuing the flow of the molecule through the nanopore,
(E5) removing the first known speed bumps from the nanopore detector system and reversing the flow of the test polynucleotide until stalled, slowed or stopped by the bulky structure at the end, and
(E6) repeating steps (E1) to (E5) with another known speed bump having a sequence of the first known speed bump plus a known number of bases longer in the flow direction of the test polynucleotide molecule of step (E3), wherein:
E-a) the known number is 1, 2, 3, 4, 5, 7,8, 9, 10, 11, 12, 13, 14, 15, or 16,
E-b) the known number of bases can be universal bases or bases that are complementary to the bases at the corresponding positions of the sample polynucleotide, and
E-c) the condition of step (E4) may be adjusted, e.g., raising the working temperature and/or increasing the electric potential value applied in step (E4) to dissociate the speed bump-test polynucleotide molecule segment successfully.

Such knowledge may facilitate identification/sequencing of the rest of the unknown sequence of the sample polynucleotide using the method described herein (e.g., using a random speed bump pool). Furthermore, the same process can be used to identify a sequence of the sample polynucleotide from another end, Thus, up to 30 bases of an unknown sample polynucleotide can be identified, which will provide a good reference in further identification/sequencing of the whole sequence of the sample polynucleotide.

Isolation of Sample Polynucleotide

Another aspect of the disclosure relates to a method of isolating a sample polynucleotide comprising:
preparing as test polynucleotide using steps (A1) to (A3) as described herein
(D1) converting one of the two bulky structure such that the corresponding end of the ss test polynucleotide can go through the nanopore without being stalled, slowed or stopped, and
(D2) applying an electric potential to release the ss target polynucleotide.

In some embodiments, the ss test polynucleotide further comprises an isolation tag as described herein, and the method further comprises step (D3) after Step (D2):
(D3) attaching the isolation tag to a ligand.

In some embodiments, wherein the ligand is further attached to a magnetic bead, step (D3) further comprising:
(D3-1) removing the conducting salt solution comprising the released ss test polynucleotide,
(D3-2) attaching the isolation tag to a ligand by mixing the released ss test polynucleotide with the ligand attached to a magnetic bead, and
(D3-3) isolating the released ss test polynucleotide using conventional isolation methods.

In some embodiments, the method further comprising step (D4) after step (D3):
(D4) removing the isolated ss test polynucleotide from the bead using conventional methods (e.g., using a basic solution), and
(D5) cleaving PBI and PB2 from the ss test polynucleotide to generate the ss sample polynucleotide.

In some embodiments, step (D5) further comprises cleaving PRI and PB2 using endonucleases, :In some embodiments, step (D5) further comprises cleaving PBI and PB2 at a cleavable site.

In an embodiment, step (DI) further comprises:
(D1-1) changing the temperature of the nanopore to about or higher than the second temperature and lower than the first temperature to convert BS2 to a non-bulky structure.

Sequencing, Identification, Concentration and Isolation of Sample Polynucleotides Using Multiple Nanopore Detectors Another aspect of the disclosure relates to a method of sequencing, identifying, concentrating and isolating of sample polynucleotides using multiple nanopore detectors. The same method as described herein regarding single nanopore detector can be used to multiple nanopore detectors.

In an embodiment, the multiple nanopores are individually addressable, wherein the electric potential of each nanopore can be individually controlled. The temperature of the nanopore may also be controlled. Thus, the ss test polynucleotide molecules detected in a nanopore can be individually released by carrying out steps (DI) to (D3) on selected nanopores.

For example, in an array of nanopore (numbered as Ni, N2, . . . NIO), each nanopore has a ss test polynucleotide trapped according to the method described herein, and the individual polynucleotide is numbered polynucleotide 1, polynucleotide 2, . . . polynucleotide 10 in the corresponding nanopores N1, N2, . . . NIO. If only polynucleotide land polynucleotide 3 are desired to be collected, nanopores N1, N2, . . . NIO can be individually controlled such that only polynucleotide land polynucleotide 3 are collected (e.g., by applying an electric potential to move polynucleotide land polynucleotide 3 from nanopores NI and N3 respectively). In an embodiment, BS2s of polynucleotide 1, polynucleotide 2, . . . polynucleotide 1O are converted to a structure that can go through the nanopores (e.g., PB2s at a temperature about or higher than the second temperature while lower than the first temperature, or cleaved to leave ss structure that can go through the nanopores, respectively). The electric potential of the nanopores N2, N4 to NIO are individually controlled such that polynucleotide 2, polynucleotide 4 to polynucleotide IO are released from the nanopores respectively, while polynucleotide land polynucleotide 3 are still trapped in nanopores NI and N3, respectively. Then nanopores NI and N3 are individually controlled to release polynucleotide 1 and polynucleotide 3, respectively to be collected, concentrated and/or isolated.

Methods and Systems for Nucleic Acid Sequencing with Tags

Nanopores may be used to sequence nucleic acid molecules indirectly, optionally with electrical detection indirect sequencing may be any method where an incorporated nucleotide in a growing strand does not pass through the nanopore. The nucleic acid molecule may pass within any suitable distance from and/or proximity to the nanopore, optionally within a distance such that tags released from nucleotide incorporation events are detected in the nanopore (e.g., as shown in FIG. 2C and FIG. 2D). Optionally, the tag is pre-loaded into the nanopore before it is released (as shown in FIG. 2D). An example of sequencing of nucleic acid molecules with tags is described in PCT Patent Publication No. WO2012/083249, which is incorporated by reference in its entirety.

Byproducts of nucleotide incorporation events may be detected by the nanopore. "Nucleotide incorporation events" are the incorporation of a nucleotide into a growing polynucleotide chain. A byproduct may be correlated with the incorporation of a given type nucleotide. The nucleotide incorporation events are generally catalyzed by an enzyme, such as DNA polymerase, and use base pair interactions with a template molecule to choose amongst the available nucleotides for incorporation at each location.

A nucleic acid sample may be sequenced using tagged nucleotides or nucleotide analogs. In some examples, a method for sequencing a nucleic acid molecule comprises (a) incorporating (e.g., polymerizing) tagged nucleotides, wherein a tag associated with an individual nucleotide is released upon incorporation, and (b) detecting the released tag with the aid of a nanopore. In some instances, the method further comprises directing the tag attached to or released from an individual nucleotide through the nanopore. The released or attached tag may be directed by any suitable technique, in some cases with the aid of an enzyme (or molecular motor) and/or a voltage difference across the pore. Alternative, the released or attached tag may be directed through the nanopore without the use of an enzyme. For example, the tag may be directed by a voltage difference across the nanopore as described herein.

Methods, devices and systems of the disclosure may detect individual nucleotide incorporation events, such as upon the incorporation of a nucleotide into a growing strand that is complementary to a template. An enzyme (e.g., DNA polymerase, RNA polymerase, ligase) may incorporate nucleotides to a growing polynucleotide chain. Enzymes (e.g., polymerases) provided herein can generate polymer chains.

The added nucleotide can be complimentary to the corresponding template nucleic acid strand which is hybridized to the growing strand (e.g., polymerase chain reaction (PCR)). A nucleotide can include a tag (or tag species) that is coupled to any location of the nucleotide including, but not limited to a phosphate (e.g., gamma phosphate), sugar or nitrogenous base moiety of the nucleotide. In some cases, tags are detected while tags are associated with a polymerase during the incorporation of nucleotide tags. The tag may continue to be detected until the tag translocates through the nanopore after nucleotide incorporation and subsequent cleavage and/or release of the tag. In some cases, nucleotide incorporation events release tags from the nucleotides which pass through a nanopore and are detected. The tag can be released by the polymerase, or cleaved/released in any suitable manner including without limitation cleavage by an enzyme located near the polymerase. In this way, the incorporated base may be identified (i.e., A, C, G, T or U) because a unique tag is released from each type of nucleotide (i.e., adenine, cytosine, guanine, thymine or uracil). In some situations, nucleotide incorporation events do not release tags. In such a case, a tag coupled to an incorporated nucleotide is detected with the aid of a nanopore. In some examples, the tag can move through or in proximity to the nanopore and be detected with the aid of the nanopore.

Methods and systems of the disclosure can enable the detection of nucleic acid incorporation events, such as at a resolution of at least 1, 2, 4, 5, 6, 7, 8, 9, 10, 20, 30, 40, 50, 100, 500, 1000, 5000, 10000, 50000, or 100000 nucleic acid bases ("bases") within a given time period. In some examples, a nanopore device is used to detect individual nucleic acid incorporation events, with each event being associated with an individual nucleic acid base. In other examples, a nanopore device is used to detect an event that is associated with a plurality of bases. For examples, a signal sensed by the nanopore device can be a combined signal from at least 2, 3, 4, or 5 bases.

In some instances, the tags do not pass through the nanopore. The tags can be detected by the nanopore and exit the nanopore without passing through the nanopore (e.g., exit from the inverse direction from which the tag entered the nanopore). The chip can be configured to actively expel the tags from the nanopore.

In some instances, the tags are not released upon nucleotide incorporation events. In some cases, nucleotide incorporation events "present" tags to the nanopore (i.e., without releasing the tags). The tags can be detected by the nanopore without being released. The tags may be attached to the nucleotides by a linker of sufficient length to present the tag to the nanopore for detection.

Nucleotide incorporation events may be detected in real-time (i.e., as they occur) and with the aid of a nanopore. In some instances, an enzyme (e.g., DNA polymerase) attached to or in proximity to the nanopore may facilitate the flow of a nucleic acid molecule through or adjacent to a nanopore. A nucleotide incorporation event, or the incorporation of a plurality of nucleotides, may release or present one or more tag species (also "tags" herein), which may be detected by a nanopore. Detection can occur as the tags flow through or adjacent to the nanopore, as the tags reside in the nanopore and/or as the tags are presented to the nanopore. In some cases, an enzyme attached to or in proximity to the nanopore may aid in detecting tags upon the incorporation of one or more nucleotides.

Tags of the disclosure may be atoms or molecules, or a collection of atoms or molecules. A tag may provide an optical, electrochemical, magnetic, or electrostatic (e.g., inductive, capacitive) signature, which signature may be detected with the aid of a nanopore.

Methods described herein may be single-molecule methods. That is, the signal that is detected is generated by a single molecule (i.e., single nucleotide incorporation) and is not generated from a plurality of clonal molecules. The method may not require DNA amplification.

Nucleotide incorporation events may occur from a mixture comprising a plurality of nucleotides (e.g., deoxyribonucleotide triphosphate (dNTP where N is adenosine (A), cytidine (C), thymidine (T), guanosine (G), or uridine (U)). Nucleotide incorporation events do not necessarily occur from a solution comprising a single type of nucleotide (e.g., dATP). Nucleotide incorporation events do not necessarily occur from alternating solutions of a plurality of nucleotides (e.g., dATP, followed by dCTP, followed by dGTP, followed by dTTP, followed by dATP). In some cases, a plurality of nucleotides (e.g., dimers of AA, AG, AC, AT, GA, GG, GG, GC, GT, CA, etc . . . ) are incorporated by a ligase.

Tagged Nucleotides

In some cases, a tagged nucleotide comprises a tag capable of being cleaved in a nucleotide incorporation event and detected with the aid of a nanopore. The tag may be attached to the 5'-phosphate of the nucleotide. In some instances, the tag is not a fluorophore. The tag may be detectable by its charge, shape, size, or any combination thereof. Examples of tags include various polymers. Each type of nucleotide (i.e., A, C, G, T) generally comprises a unique tag.

Figure 25:
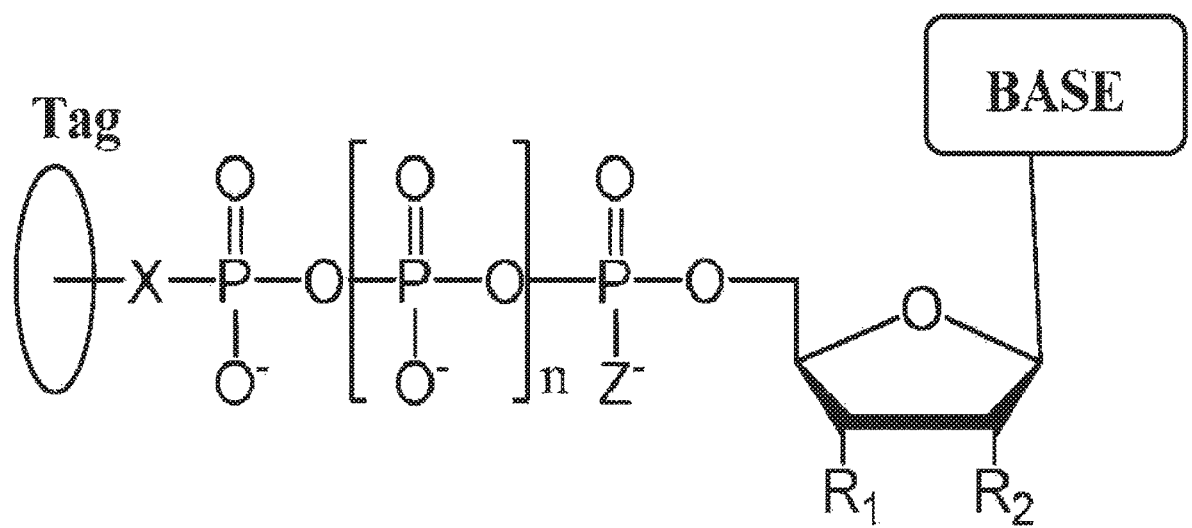
FIG. 25 shows an example of a tag molecule attached to the phosphate of a nucleotide.

Tags may be located on any suitable position on the nucleotide. FIG. 25 provides an example of a tagged nucleotide. Here, $R_1$ is generally OH and $R_2$ is H (i.e., for DNA) or OH (i.e., for RNA), although other modifications are acceptable. In FIG. 25, X is any suitable linker. In some cases, the linker is cleavable. Examples of linkers include without limitation, 0, NH, S or $CH_2$. Examples of suitable chemical groups for the position Z include 0, S, or $BH_3$. The base is any base suitable for incorporation into a nucleic acid including adenine, guanine, cytosine, thymine, uracil, or a derivative thereof. Universal bases are also acceptable in some cases.

The number of phosphates (n) is any suitable integer value (e.g., a number of phosphates such that the nucleotide may be incorporated into a nucleic acid molecule). In some instances, all types of tagged nucleotides have the same number of phosphates, but this is not required. In some applications, there is a different tag for each type of nucleotide and the number of phosphates is not necessarily used to distinguish the various tags. However, in some cases more than one type of nucleotide (e.g., A, C, T, G or U) have the same tag molecule and the ability to distinguish one nucleotide from another is determined at least in part by the number of phosphates (with various types of nucleotides having a different value for n). In some embodiments, the value for n is 1, 2, 3, 4, 5, 6, 7, 8, 9, 10, or greater.

Suitable tags are described herein. In some instances, the tag has a charge which is reverse in sign relative to the charge on the rest of the compound. When the tag is attached, the charge on the overall compound may be neutral. Release of the tag may result in two molecules, a charged tag and a charged nucleotide. The charged tag passes through a nanopore and is detected in sonic cases.

Figure 26:
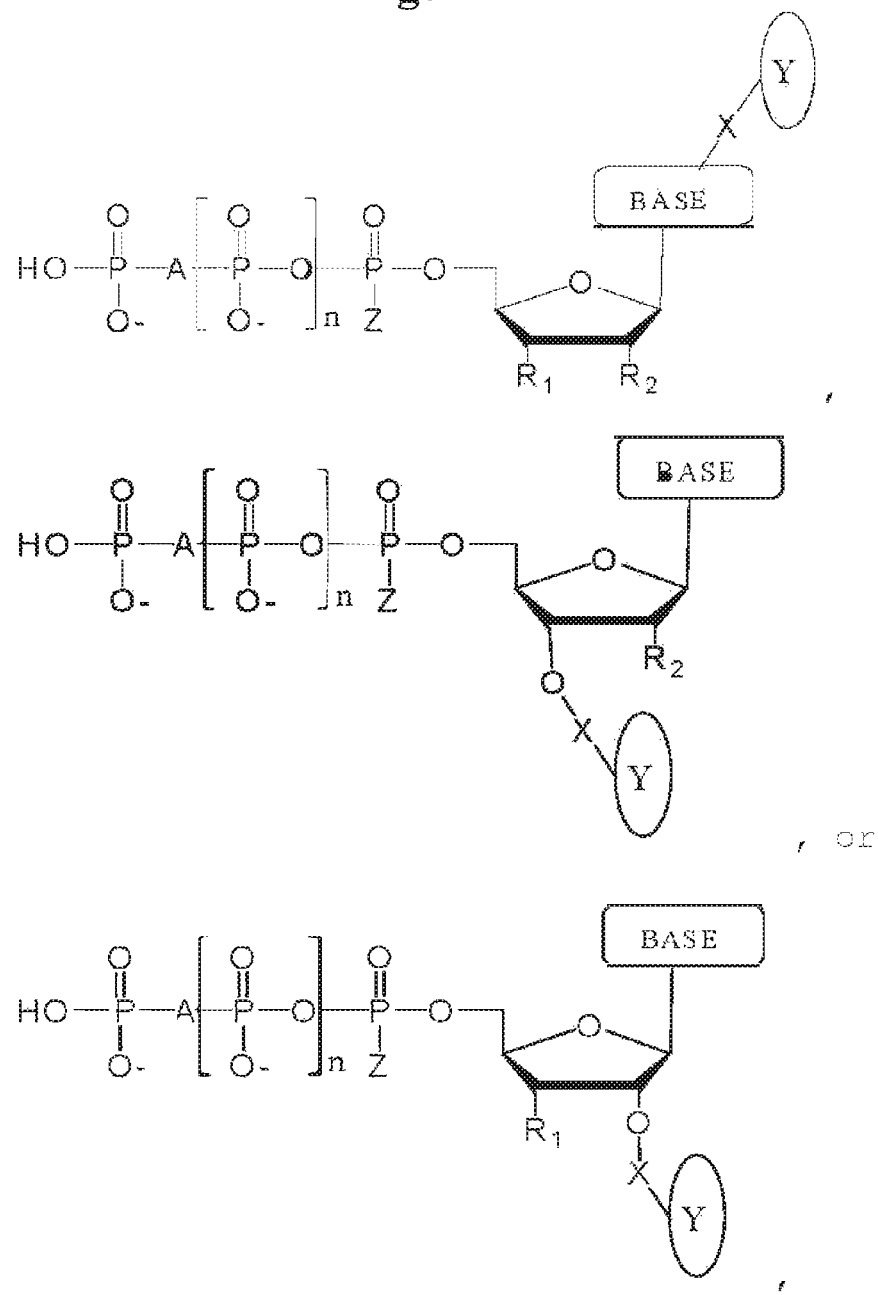
FIG. 26 shows examples of alternate tag locations.

More examples of suitable tagged nucleotides are shown in FIG. 26. The tag may be attached to the sugar molecule, the base molecule, or any combination thereof. With reference to FIG. 13, Y is a tag and Xis a linker (optionally cleavable). Furthermore, $R_1$, if present, is generally OH, —$OCH_2N_3$ or -0-2-nitrobenzyl, and $R_2$, if present, is generally H. Also, Z is generally 0, S or $BH_3$, and n is any integer including 1, 2, 3, or 4. In some cases, the A is 0, S, CH2, CHF, CFF, or NH.

With continued reference to FIG. 26, the type of base on each dNPP analogue is generally different from the type of base on each of the other three dNPP analogues, and the type of tag on each dNPP analogue is generally different from the type of tag on each of the other three dNPP analogues. Suitable bases include, but are not limited to adenine, guanine, cytosine, uracil or thymine, or a derivative of each thereof. In some cases, the base is one of 7-deazaguanine, 7-deazaadenine or 5-methylcytosine.

In cases where $R_1$ is —O—$CH_2N_3$, the methods optionally further comprise treating the incorporated dNPP analogue so as to remove the —$CH_2N_3$ and result in an OH group attached to the 3' position thereby permitting incorporation of a further dNPP analogue.

In cases where $R_1$ is -0-2-nitrobenzyl, the methods optionally further comprise treating the incorporated nucleotide analogue so as to remove the -2-nitrobenzyl and result in an OH group attached to the 3' position thereby permitting incorporation of a further dNTP analogue.

Examples of Tags

A tag may be any chemical group or molecule that is capable of being detected in a nanopore. In some cases, a tag comprises one or more of ethylene glycol, an amino acid, a carbohydrate, a peptide, a dye, a chemilluminiscent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof.

It is also contemplated that the tag further comprises appropriate number of lysines or arginines to balance the number of phosphates in the compound.

In some cases, the tag is a polymer. Polyethylene glycol (PEG) is an example of a polymer and has the structure as follows:

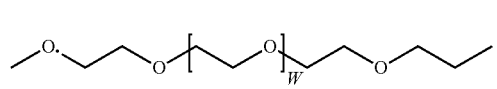

Any number of ethylene glycol units (W) may be used. In some instances, W is an integer between O and 100. In some cases, the number of ethylene glycol units is different for each type of nucleotide. In an embodiment, the four types of nucleotides comprise tags having 16, 20, 24 or 36 ethylene glycol units. In some cases, the tag further comprises an additional identifiable moiety, such as a coumatin based dye. In some cases, the polymer is charged. In some instances, the polymer is not charged and the tag is detected in a high concentration of salt (e.g., 3-4 M).

As used herein, the term "alkyl" includes both branched and straight-chain saturated aliphatic hydrocarbon groups having the specified number of carbon atoms and may be unsubstituted or substituted. As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution(s) result(s) in a stable compound. Substituted groups also include groups in which one or more bonds to a carbon(s) or hydrogen(s) atom are replaced by one or more bonds, including double or triple bonds, to a heteroatom.

Methods for Attaching Tags

Any suitable method for attaching the tags may be used. In an example, tags may be attached to the terminal phosphate by (a) contacting a nucleotide triphosphate with dicyclohexylcarbodiimide/dimethylformamide under conditions permitting production of a cyclic tiimetaphosphate, (b) contacting the product resulting from step a) with a nucleophile so as to form an —O0H or —NH$_2$ functionalized compound, and (c) reacting the product of step b) with a tag having a —COR group attached thereto under conditions permitting the tag to bond indirectly to a terminal phosphate thereby forming the nucleotide triphosphate analogue.

In some cases, the nucleophile is H$_2$N—R—OH, H$_2$N—R—NH$_2$, R'S—R—OH, R'S—R—NH$_2$, or

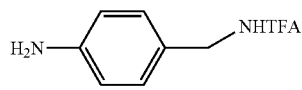

In some instances, the method comprises, in step b), contacting the product resulting from step a) with a compound having the structure:

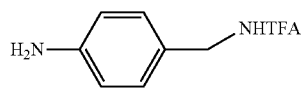

and subsequently or concurrently contacting the product with NR$_4$OH so as to form a compound having the structure:

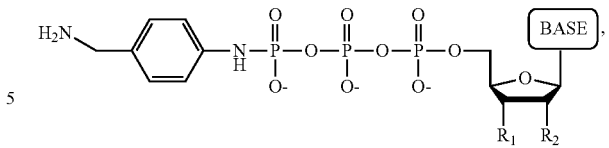

The product of step b) may then be reacted with a tag having a —COR group attached thereto under conditions permitting the tag to bond indirectly to a terminal phosphate thereby forming the nucleotide triphosphate analogue having the structure:

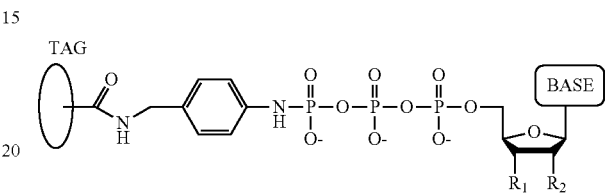

wherein R$_1$ is OH, wherein R$_2$ is H or OH, wherein the base is adenine, guanine, cytosine, thymine, uracil, a 7-deazapurine or a 5-methylpyrimidine.

Release of Tags

A tag may be released in any manner. In some cases, the tag is attached to polyphosphate (e.g., FIG. 25) and incorporation of the nucleotide into a nucleic acid molecule results in release of a polyphosphate having the tag attached thereto. The incorporation may be catalyzed by at least one polymerase, optionally attached to the nanopore. In some instances, at least one phosphatase enzyme is also attached to the pore. The phosphatase enzyme may cleave the tag from the polyphosphate to release the tag. In some cases, the phosphatase enzymes are positioned such that pyrophosphate produced by the polymerase in a polymerase reaction interacts with the phosphatase enzymes before entering the pore.

In some cases, the tag is not attached to polyphosphate (see, e.g., FIG. 26). In these cases, the tag is attached by a linker (X), which is optionally cleavable. Methods for production of cleavably capped and/or cleavably linked nucleotide analogues are disclosed in U.S. Pat. No. 6,664,079, which is entirely incorporated herein by reference. The linker need not be cleavable.

The linker may be any suitable linker and optionally cleaved in any suitable manner. The linkers may be photocleavable. In an embodiment UV light is used to photochemically cleave the photochemically cleavable linkers and moieties. In an embodiment, the photocleavable linker is a 2-nitrobenzyl moiety.

The —CH$_2$N$_3$ group may be treated with TCEP (tris(2-carboxyethyl)phosphine) so as to remove it from the 3' atom of a dNPP analogue, or rNPP analogue, thereby creating a 3' OH group.

Detection of Tags

In some instances, a polymerase draws from a pool of tagged nucleotides comprising a plurality of different bases (e.g., A, C, G, T, and/or U). It is also possible to iteratively contact the polymerase with the various types of tagged bases. In this case, it may not be necessary that each type of nucleotide have a unique base, but the cycling between different base types adds cost and complexity to the process in some cases, nevertheless this embodiment is encompassed in the present invention.

Figure 27:
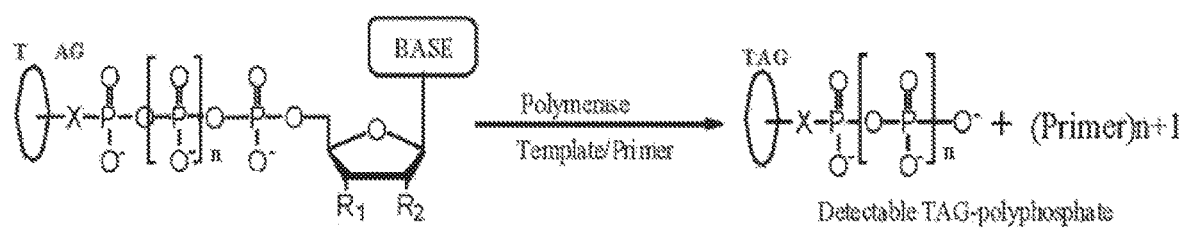
FIG. 27 shows detectable TAG-polyphosphate and detectable TAG.

FIG. 27 shows that incorporation of the tagged nucleotide into a nucleic acid molecule (e.g., using a polymerase to extend a primer base paired to a template) can release a detectable TAG-polyphosphate in some embodiments. In some cases, the TAG-poly phosphate is detected as it passes through the nanopore. In some embodiments, the TAG-poly phosphate is detected as it resides in the nanopore.

In some cases, the method distinguishes the nucleotide based on the number of phosphates comprising the polyphosphate (e.g., even when the TAC is are identical). Nevertheless, each type of nucleotide generally has a unique tag.

The TAG-polyphosphate compound may be treated with phosphatase (e.g., alkaline phosphatase) before passing the tag into and/or through a nanopore and measuring the ionic current.

Tags may flow through a nanopore after they are released from the nucleotide. In some instances, a voltage is applied to pull the tags through the nanopore. At least about 85%, at least 90%, at least 95%, at least 99%, at least 99.9 or at least 99.99% of the released tags may translocate through the nanopore.

In some instances, the tags reside in the nanopore for a period of time where they are detected. In some instances, a voltage is applied to pull the tags into the nanopore, detect the tags, expel the tags from the nanopore, or any combination thereof. The tags can be released or remain bound to the nucleotide upon nucleotide incorporation events.

The tag may be detected in the nanopore (at least in part) because of its charge. In some instances, the tag compound is an alternatively charged compound which has a first net charge and, after a chemical, physical or biological reaction, a different second net charge. In some instance, the magnitude of the charge on the tag is the same as the magnitude of the charge on the rest of the compound. In an embodiment, the tag has a positive charge and removal of the tag changes the charge of the compound.

In some cases, as the tag passes into and/or through the nanopore, it may generate an electronic change. In some cases the electronic change is a change in current amplitude, a change in conductance of the nanopore, or any combination thereof.

The nanopore may be biological or synthetic. It is also contemplated that the pore is proteinaceous, for example wherein the pore is an alpha hemolysin protein. An example of a synthetic nanopore is a solid-state pore or graphene.

In some cases, polymerase enzymes and/or phosphatase enzymes are attached to the nanopore. Fusion proteins or disulfide crosslinks are example of methods for attaching to a proteinaceous nanopore. In the case of a solid state nanopore, the attachment to the surface near the nanopore may be via biotin-streptavidin linkages. In an example the DNA polymerase is attached to a solid surface via gold surface modified with an alkanethiol self-assembled monolayer functionalized with amino groups, wherein the amino groups are modified to NHS esters for attachment to amino groups on the DNA polymerase.

The method may be performed at any suitable temperature. In some embodiments, the temperature is between 4° C. and 10° C. In some embodiments, the temperature is ambient temperature.

The method may be performed in any suitable solution and/or buffer. In some instances, the buffer is 300 mM KCl buffered to pH 7.0 to 8.0 with 20 mM HEPES. In some embodiments, the buffer does not comprise divalent cations. In some cases, the method is unaffected by the presence of divalent cations.

Sequencing Both Nucleic Acid Strands

Double stranded nucleic acid molecules (e.g., deoxyribonucleic acid) may have a sense strand and an anti-sense strand that hybridize (e.g., bind to each other) according to well known base pair interactions (e.g., A with T and G with C). In some cases, the sense strand and anti-sense strand wrap around each other in a well known alpha-helical configuration. In general, the sense strand is the strand that encodes an amino acid according to well known codons used by most organisms (e.g., from the 5' to 3' direction, TCA generally encodes for the amino acid serine, etc . . . ). However, the designation of which strand is the sense strand and which is the anti-sense strand can be arbitrary. Not all nucleic acids encode for proteins.

It is recognized herein that the nucleic acid sequence of the anti-sense strand (e.g., from the 3' to 5' direction) can be used to determine and/or verify the sequence of the sense strand (e.g., from the 5' to 3' direction) (e.g., because of the known base pair interactions). Furthermore, sequencing both the sense strand and the anti-sense strand to determine the sequence of a double stranded nucleic acid molecule may have certain advantages. In some instances, it may be easier to determine the sequence of either the sense strand or the anti-sense strand (e.g., for any reason or an unknown reason-examples include but are not limited to (a) one strand may form secondary structures not formed by the other strand or (b) the signal from one strand is relatively stronger and/or more well resolved than the signal from the other strand). The sequence signals and/or information obtained from one strand can be complimentary to the sequence signals and/or information obtained from the other strand (e.g., a base that is not readily resolved on one strand may be readily resolved on the other strand).

Nucleic acid molecules can have various types of mutations and/or mismatches. For example, a base pair mismatch may be present where any number of base positions (e.g., 1, 2, 3, 4, 5, 6, 7, or more) are not complimentary between the two strands (e.g., an A on the sense strand and a G on the anti-sense strand). In some cases, one strand can have an insertion or deletion of base positions relative to the other strand (e.g., the sense strand has a sequence ACCTCGAT that is not base paired with the anti-sense strand). The sense strand and the anti-sense strand can be base paired in the 5' direction from the deletion and/or insertion, in the 3' direction from the deletion and/or insertion, or in both directions. In some cases, the double stranded nucleic acid molecule may contain information (e.g., epigenetic markers such as methylated bases) that is only found on one of the strands. In this case, one can sequence both the sense strand and the anti-sense strand to detect the epigenetic information (e.g., methylated bases).

Provided herein are methods for sequencing both the sense strand and the anti-sense strand using nanopores. The ends of the sense strand and the anti-sense strand can be ligated together to form a single-stranded nucleic acid molecule to be sequenced that contains both the sense strand and the anti-sense strand. The single stranded nucleic acid molecule can be sequenced by passing it through a nanopore (e.g., as shown in FIG. 2B) or passing it adjacent to a nanopore where tag molecules are detected (e.g., as shown in FIG. 2C and FIG. 2D).

In an aspect, a method for sequencing a nucleic acid molecule or portion thereof comprises (a) providing a double stranded nucleic acid molecule comprising a sense strand and an anti-sense strand, (b) ligating a first nucleic acid segment on a first end of the double stranded nucleic acid molecule that links the sense strand with the anti-sense strand, (c) dissociating the double stranded nucleic acid to provide a single stranded nucleic acid molecule comprising a sense portion of said sense strand and an anti-sense portion of said anti-sense strand, (d) passing the single stranded nucleic acid molecule through or in proximity to a nanopore in a membrane that is disposed adjacent or in proximity to an electrode, (e) using the electrode, obtaining current measurements while passing the single stranded nucleic acid molecule through or in proximity to the nanopore, and (f) determining the sequence of the double stranded nucleic acid from the current measurements obtained in (e). The electrode may be adapted to detect a current upon the single stranded nucleic molecule passing through or in proximity to the nanopore.

Figure 28:
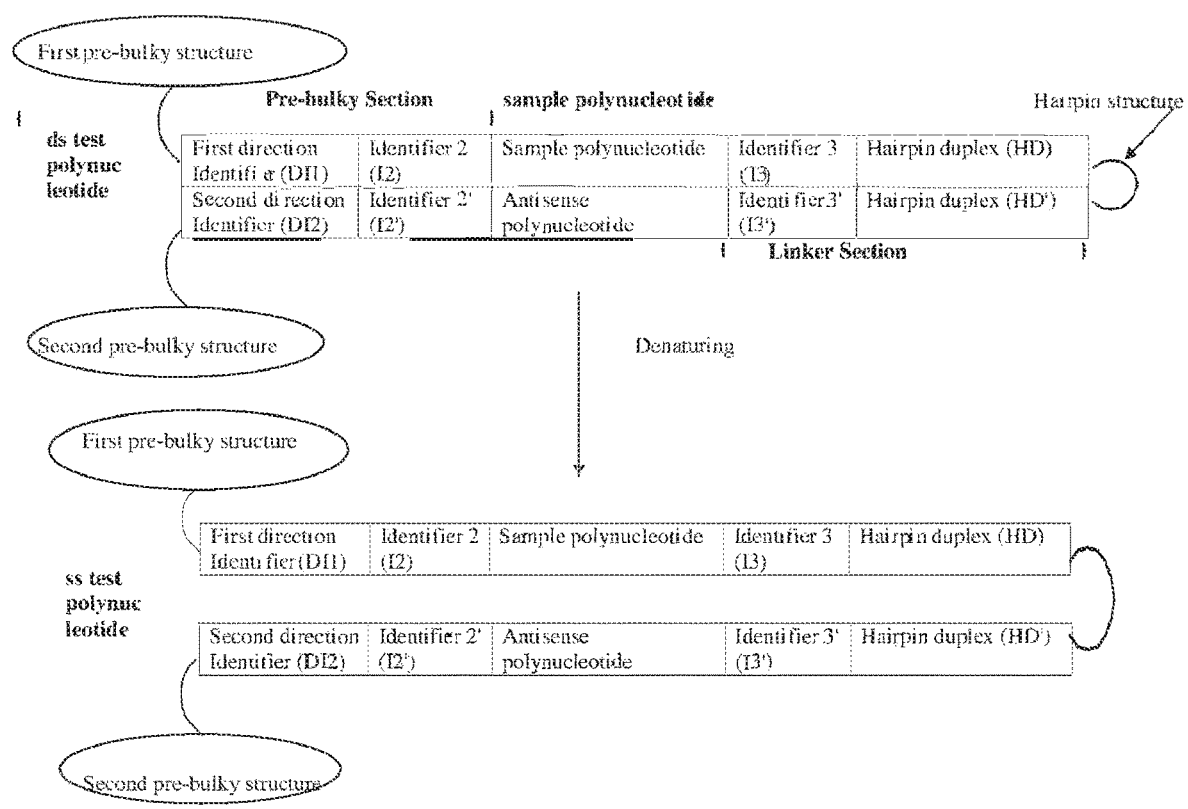
FIG. 28 illustrates an example of a test polynucleotide comprising a sample polynucleotide, an antisense polynucleotide of the sample polynucleotide, a linker linking the sample polynucleotide and the antisense polynucleotide thereof, a first pre-bulky structure and a second pre-bulky structure.

The first nucleic acid segment can have a nucleic acid hairpin (e.g., Linker Section in FIG. 28). The hairpin can have a non-base paired hairpin structure located between two segments of a hairpin duplex (HD) comprising base paired (double stranded) nucleic acid. The first nucleic acid segment can further comprise a first identifier. The first identifier can identify from which sample the double stranded nucleic acid molecule is derived.

In some embodiments, the method further comprises ligating a second nucleic acid segment onto the second end of the double stranded nucleic acid (e.g., Pre-bulky Section in FIG. 28). In some instances, the second nucleic acid segment comprises a portion capable of trapping the single stranded nucleic acid molecule in the nanopore (e.g., first and/or second pre-bulky structure). In some embodiments, the second nucleic acid segment is capable of trapping, the single stranded. nucleic acid molecule in the nanopore below a certain temperature (e.g., when the temperature is below about 60° C., below about 50° C., below about 40° C., below about 30° C., below about 20° C., below about 10° C., below about 0° C., or below about −10° C.). In some embodiments, the second nucleic acid segment comprises a second identifier (e.g., capable of being used to determine whether the single stranded nucleic acid molecule is passing through the nanopore in a first direction or in a second direction).

In some cases, the rate of passage of the single stranded nucleic acid molecule through or in proximity to the nanopore is slowed with the aid of one or more speed bump molecules as described herein. Current measurements can be obtained when the rate of passage of the single stranded nucleic acid molecule is slowed. In some embodiments, current measurements are made at a plurality of voltages applied across the nanopore and/or across the membrane. In some instances, an individual speed bump molecule of said one or more speed bump molecules comprises ribonucleic acid.

In an aspect, the present invention is directed to a method for obtaining sequence and/or structure information of a sample polynucleotide using a nanopore detector and a test polynucleotide comprising both the sample polynucleotide structure and the antisense polynucleotide thereof. The test polynucleotide can be trapped in the nanopore by a stopper-test polynucleotide segment for a dwelling time. During this dwelling time, a constant electric potential or a varied electric potential profile comprising electric potentials having more than one voltage are applied to the electrodes of the nanopore detector and a set of electrical signals are obtained. The electrical potential can be varied according to a waveform (e.g., the waveforms shown in FIG. 29). The electrical signals collected under the constant or varied electric potential profile may provide information of the sequence and/or structure that is in front of the stopper-test polynucleotide segment in the flow direction of the test polynucleatide.

Depending on the nature of the nanopore and/or the test polynucleotide, the electrical signals collected from different sequences and/or structures of the sample polynucleotide may be difficult to resolve with high confidence. However, taking the electrical signals collected from the sample polynucleotide and the corresponding antisense polynucleotide together may improve the confidence in resolving the sequences and/or structures in the sample polynucleotide. Characterizing the sample polynucleotide and the corresponding antisense polynucleotide in the same nanopore may also lower the systematic error by collecting singnals from the same nanopore at about the same time. Previous methods analyze only the sample polynucleotide. Thus, the electrical signals collected from reading the sample polynucleotide and the antisense polynucleotide thereof may provide a more reliable and accurate determination of the sample polynucleotide sequence and/or structure than the currently available methods.

One aspect of the present invention relates to a method of obtaining structure information of a sample, comprising, (F1) preparing a double strand (ds) test polynucleotide comprising:
  a ds sample section having a first end and a second end, the ds sample section comprising a single strand (ss) sample polynucleotide and as antisense polynucleotide thereof;
  a linker linking the ss sample polynucleotide and the ss antisense polynucleotide at the first end, and
  a first pre-bulky structure and a second pre-bulky structure each linked to the sense polynucleotide or antisense polynucleotide at the second end;

(F2) denaturing the ds test polynucleotide of A1 to as test polynucleotide having the first pre-bulky structure on one end and the second pre-bulky structure on the other end;

(GI) forming a first bulky structure (BSI) from the first pre-bulky structure at a first condition, (G2) applying an electric potential to flow the ss test polynucleotide through a nanopore of a nanopore detector, optionally until the ss test polynucleotide is stalled, slowed or stopped by BSH before the constriction area of the nanopore, (G3) forming a second bulky structure (BS2) from the second pre-bulky structure at a second condition, (G4) optionally applying another electric potential to reverse the flow of the ss test polynucleotide until the ss test polynucleotide is stalled, slowed or stopped by BSL before the constriction area of the nanopore, (G5) contacting a stopper with the ss test polynucleotide to form a test polynucleotide complex comprising a first stopper-test polynucleotide segment;

(G6) applying another electric potential to flow the test polynucleotide complex through the nanopore until the first stopper-test polynucleotide segment is stalled, slowed or stopped before a constriction area of the nanopore, (G7) applying a constant electric potential profile or a varied electric potential profile comprising electric potentials having more than one voltages to the electrodes of the nanopore detector when the first stopper-test polynucleotide segment is stalled inside the nanopore for a dwelling time and obtaining a first set of electrical signals, and (G8) determining the structure that is in front of the first stopper-test polynucleotide segment in the flow direction of the test polynucleotide by comparing the first set of electrical signals with electrical signals collected under the same electric potential profile in step (G7) for a known structure that is in front of the stopper-test polynucleotide segment in the flow direction of the test polynucleotide (G9) dissociating the first stopper-test polynucleotide segment and continuing the flow of the polynucleotide through the nanopore, (G10) repeating steps (G5) to (G9) until the ss test polynucleotide is stalled, slowed or stopped by BSH or BSL, (GII) optionally repeating steps (G4) to (G10), preferably for 1, 2, 3, 4, 5, 6, 7, 8, 9, 10, 11, 12, 13, 14, 15, 16, 17, 18, 19, 20, or 100 times and (G12) constructing the sample polynucleotide sequence by overlapping the collected nucleotide sequence information of both the sample polynucleotide and the antisense polynucleotide thereof.

In an embodiment, both the first and second pre-bulky structures are polynucleotide/oligonucleotide pre-bulky structures. The first pre-bulky structure forms the corresponding first bulky structure at a first temperature. The second pre-bulky structure forms the corresponding second bulky structure at a second temperature. And the first temperature is higher than the second temperature.

In another embodiment, the first pre-bulky structure is a polynucleotide and/or oligonucleotide pre-bulky structure that forms the first bulky structure via interaction with a ligand specific to the first pre-bulky structure. In an embodiment, the formation of the first bulky structure is temperature-independent. The second pre-bulky structure can be such that the conversion between the pre-bulky structure and the corresponding bulky structure is temperature-dependent.

In an embodiment, the first pre-bulky structure comprising a biotin modified polynucleotide and/or oligonucleotide forms the first bulky structure via binding to streptavidin via biotin/streptavidin interaction. The formation of the first bulky structure can be temperature independent.

Referring to FIG. 28, in an embodiment, a ds test polynucleotide described herein comprises a sample polynucleotide, an antisense polynucleotide of the sample polynucleotide (antisense polynucleotide), a linker linking the sample polynucleotide and the antisense polynucleotide thereof (sections I3-HD-hairpin-HD'-I3'), a first pre-bulky structure, a second pre-bulky structure, a first direction identifier (DII) to indicate the proper formation of the first bulky structure (FIG. 28). Each of the sections 12, 13, 12' and I3' optionally comprises one or more identifiers described herein. HDI and HDI' together are a polynucleotide duplex. Section DI-I comprises a first direction identifier and optionally one or more other identifiers. Section LI comprises a low temperature direction identifier and optionally one or more other identifiers. Sections 12-HI may or may not be completely complementary to sections but at least a portion thereof forms a duplex structure. The duplex section between sections 12'-HI and 12'-LI can be in close proximity, and more preferably adjacent, to the end of the ds sample polynucleotide section (FIG. 28). The ds test polynucleotide can be converted into a ss test polynucleotide by conventional denaturing technique well known in the art (e.g., by heat).

The sample polynucleotide can be a DNA or RNA polynucleotide, and the antisense polynucleotide is a DNA or RNA polynucleotide that is complementary to the sample polynucleotide. The linker section linking the sample polynucleotide and the antisense sample polynucleotide on the first end of the sample duplex section by: (a) linking the 3' end of the sample polynucleotide and the 5' end of the antisense sample polynucleotide, and/or (b) linking the 5' end of the sample polynucleotide and the 3' end of the antisense sample polynucleotide.

In an embodiment, the test polynucleotide has 1 to about 10,000 bases, 1 to about 1,000 bases, 1 to about 500 bases, 1 to about 300 bases, Ito about 200 bases, 1 to about 100 bases, about 5 to about 10,000 bases, about 5 to about 1,000 bases, about 5 to about 500 bases, about 5 to about 300 bases, 5 to about 200 bases, 5 to about 100 bases, 10 to about 10,000 bases, 10 to about 1,000 bases, 10 to about 500 bases, 10 to about 300 bases, 10 to about 200 bases, 10 to about 100 bases, 20 to about 10,000 bases, 20 to about 1,000 bases, 20 to about 500 bases, 20 to about 300 bases, 20 to about 200 bases, 20 to about 100 bases, 30 to about 10,000 bases, 30 to about 1,000 bases, 30 to about 500 bases, 30 to about 300 bases, 30 to about 200 bases, 30 to about 100 bases, 30 to about 50 bases, 50 to about 10,000 bases, 50 to about 1,000 bases, 50 to about 500 bases, 50 to about 300 bases, 50 to about 200 bases, or 50 to about 100 bases.

The stopper can be a speed bump (e.g., oligonucleotide) described herein, and the ss test polynucleotide can comprise a section of ss polynucleotide that is to be bound by the speed bump in a method described herein. In some embodiments, the test polynucleotide is a test DNA or RNA, and the speed bump is a DNA or RNA, speed bump. A speed bump can have a length of 2, 3, 4, 5, 6, 7, 8, 9, 10, 11, 12 13, 14, 15, or 16, preferred 10 or less, 8 or less, 6 or less and 4 or less. The speed bump may comprise one or more nucleotides selected from the group consisting of universal nucleotides, locked nucleotides, primary nucleotides, modifications thereof, and combinations thereof. Modifications of universal nucleotides, and primary nucleotides include modifications at the nucleobase structures, the backbone structures (e.g., glycol nucleotides, morpholinos, and locked nucleotides) and combinations thereof. In another preferred embodiment, the backbone structures of the speed bump is modified (e.g., glycol nucleotides, morpholinos, and locked nucleotides) at designated position(s), random positions or combinations thereof. In some embodiments, the first base pair of the speed bump-test polynucleotide segment may be partially or completely in the nanopore and contributes to the electrical signals obtained in step (G7). Thus, step (G8) further comprises obtaining structure information of the first base pair of the speed bump-test polynucleotide segment in the flow direction of the ss test polynucleotide. In some embodiments, it is preferred to construct the speed bumps to have a universal nucleotide which base-pair with all primary nucleobases (A, T, C, G and U) at the 5' and/or 3' end to normalize the contribution of the first base pair of the speed bump-test polynucleotide segment and makes the signals easier to analyze.

In some embodiments, it is preferred to construct the speed bumps to have a universal nucleotide which base-pair with all primary nucleobases (A T, C, G and U) at the 5' and/or 3' end to normalize the contribution of the first base pair of the speed bump-test polynucleotide segment and makes the signals easier to analyze.

The stopper can be an enzyme that binds to the ss test polynucleotide at a duplex section created by hybridization of the ss test polynucleotide and a primer, and optionally moves the ss test polynucleotide through the nanopore and causes the reading of the test polynucleotide either by staying associated with the test polynucleotide during the reading process in the pore, or by disassociating after a single nucleotide extension of the antisense strand of the test polynucleotide and subsequently inserting the newly created sample/antisense duplex into the pore to read one base different than the prior duplex sample strand read. Examples of such enzymes include, without Klenow-exo minus, Phi29 poly n erase, Phi29-exo minus polymerase, T4 DNA polymerase, M-MuLV Reverase Transcriptase, and T7 Gp4a Helicase.

In some embodiments, the stopper is an enzyme, the ss test polynucleotide further comprises an enzyme binding site for the enzyme to bind to the ss test polynucleotide. Referring to FIG. 28, such enzyme binding site may exist in sections DII, D12, 12 or 12', and preferably in DII or 12 to ensure that all sample polynucleotide and antisense polynucleotide can be characterized by the nanopore.

In some embodiments, the first base pair of the stopper-test polynucleotide segment may be partially or completely in the nanopore, the electrical signals obtained in step (G7), step (G8) further comprising determining the first base pair of the stopper-test polynucleotide segment in the flow direction of the ss test polynucleotide. In some embodiments, it is preferred to construct the stopper to have a universal nucleotide which base-pair with all primary nucleobases (A, T C, G and U) to form the first base pair of the stopper-test polynucleotide segment and makes the signals easier to analyze.

In some embodiments, the structure in front of the stopper-test polynucleotide segment determined in step (G8) is a 1, 2, 3, 4, 5, 6, 7, 8, 9, 10, 11, 12, 13, 14, 15, 16, 17, 18, 19, 20 to 50 bases, 50 to 100 bases, 100 to 200 bases, 200 to 500 bases, or greater than a 500 base sequence. In some embodiments, the structure in front of the stopper-test polynucleotide segment determined in step (G8) is any nucleotide sequence at position 1-50, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or a combination thereof from the stopper-test polynucleotide segment.

In some embodiments, the electric potential profile applied in step (G7) is a constant electric potential profile having a voltage of about 160 mV to about −160 mV, about 160 mV to about 0 mV, about 160 mV to about 60 mV, about 11.00 mV to about 0 mV, 11.00 mV to about 80 mV, or 80 mV to about 70 mV.

In some embodiments, the electric potential profile applied in step (G7) is a varied electric potential profile comprising electric potentials having two or more voltages each applied for a certain time, Ire some embodiments, the varied electric potential profile comprises one or more electric potentials resulted during step (G6) or after the stopper-test polynucleotide complex is stalled, slowed or stopped in the nanopore in step (G6). At least two electric potentials of the two or more electric potentials applied have a difference of more than about 1 mV, 5 mV, 10 mV, or 30 mV. In an embodiment, the electric potentials have a voltage of about 160 mV to about −160 mV, about 160 mV to about 0 mV, about 160 mV to about 60 mV, about 100 mV to about 0 mV, 100 mV to about 80 mV, or 80 mV to about 70 mV. The time for each electric potential can be at least about 5 μs. at least about 10 μs, at least about 50 μs, at least about 100 μs, at least about 500 μs, at least about 1 ms, at least about 5 ms, at least about 10 ms, at least about 50 ms, at least about 100 ms, at least about 500 ms, at least about 1 s, or at least about 2 s.

In some embodiments, the varied electric potential profile applied in step (G7) comprises an electric potential ramp changing from a first electric potential to a second electric potential over a certain time period. In some embodiments, the varied electric potential profile can comprise one or more electric potentials resulted during step (G6) or after the stopper-test polynucleotide complex is stalled, slowed or stopped in the nanopore in step (G6). For example, the first electric potential of the varied electric potential profile can be an electric potential resulted during step (G6) or after the stopper-test polynucleotide complex is stalled, slowed or stopped in the nanopore in step (G6). The difference between the highest electric potential and the lowest electric potential of the varied electric potential profile is more than about 1 mV, 5 mV, 10 mV, 20 mV, or 30 mV. In another embodiment, the first electric potential is about 160 mV and the second electric potential is about −160 mV. In an embodiment, the first electric potential is about 160 mV and the second electric potential is about 60 mV. In another embodiment, the first electric potential is about 100 mV and the second electric potential is about 0 mV. In another embodiment, the first electric potential is about 160 mV, the second electric potential is about 0 mV. In another embodiment, the first electric potential is about 100 mV and the second electric potential is about 80 mV. In another embodiment, the first electric potential is about 100 mV and the second electric potential is about 90 mV. In another embodiment, the first electric potential is about 90 mV and the second electric potential is about 85 mV. The predetermined time period is at least about 5 μs, at least about 10 is, at least about 50 μs, at least about 100 μs, at least about 500 μs, at least about 1 ms, at least about 5 ms, at least about 10 ms, at least about 50 ms, at least about 100 ms, at least about 500 ms, at least about 1 s, or at least about 2 s.

In some embodiments, the varied electric potential profile applied in step (G7) comprises an electric potential waveform changing from a first electric potential to a second electric potential to a third electric potential and so on to a plurality of electric potentials that in total form a varied applied electric potential waveform.

In some embodiments, step (G7) is performed in a solution having at least OIM salt. The salt is selected from the group consisting of chloride, phosphate, nitrate and sulfate.

In some embodiments, step (G7) is performed in a solution having a pH of about 6.5 to about 8.5 or from about 7 to about 8. Any buffer that can provide such pH can be used. Examples include, without limitation, HEPES buffer.

In some embodiments, the nanopore is an alpha hemolysin nanopore or a MspA nanopore.

In some embodiments, the nanopore detector comprises at least one metal electrode embedded in an isolation surface. Examples of the materials the metal electrode comprises include, without limitation, silver, sliver chloride, platinum, gold, ruthenium and nickel. Examples of the materials the isolation surface comprises include, without limitation, a plastic material (e.g., Teflon), a glass, or a semiconductor material (e.g., silicon, germanium, and gallium). In some embodiments, the isolation surface is further modified to be hydrophobic and lipophilic using methods known in the art to facilitate attachment of biological molecules to the isolation surfaces. For example, further silanization with silane molecules containing 6 to 20 carbon-long chains (e.g., octadecyl-trichlorosilane, octadecyl-trimethoxysilane, or octadecyl-triethoxysilane) or DMOCs can be done on silicon dioxide surface on a silicon surface.

In an embodiment, the structure that is in front of the stopper-test polynucleotide segment in the flow direction of the test poi nucleotide in step (G7) can be determined according to the information gathered from the sample polynucleotide and the corresponding complementary structure in the antisense polynucleotide thereof. Thus, the reliability and accuracy of the reading is improved by gathering information from both the sample polynucleotide and the antisense polynucleotide. Furthermore, in some embodiments, certain structures providing similar signals in step (G7) can be further differentiated from each other by the corresponding complementary structure in the antisense polynucleotide.

In one example, a single nucleotide difference of the structure that is in front of the stopper-test polynucleotide segment in the flow direction of the test polynucleotide can be characterized in step (G7). C and T can be determined with high confidence(>about 97%, >about 99% and preferably>99.5% confidence). G and A can be characterized with a lower confidence (about 90 to 95% confidence). The complementary structures of G and A are C and T, respectively. Thus, determining the C's and T's in both the sample DNA and the antisense strand provides the structure of the sample DNA with a higher confidence (>99%, preferably >99.5% confidence) than determining all four nucleotides A, C, T and G from information collected from the sample DNA only (about 95% confidence). In some embodiments, the nanopore is an alpha hemolysin nanopore, the polynucleotide characterized is a DNA or RNA, and the electric potential(s) applied in steps (G6 to G7), either in a constant profile or a varied profile is at least about 10 mV, at least about 50 mV, at least about 60 mV, about 60 mV to about 160 mV, preferably at least about 90 mV, at least about 100 mV, more preferably about 100 mV to about 160 mV.

In another example, a single nucleotide difference of the structure that is in front of the stopper-test polynucleotide segment in the flow direction of the test polynucleotide can be characterized in step (G7). C and A can be determined with high confidence(>about 98%, preferably>99.5% confidence). G and T can be characterized with a lower confidence (about 95% confidence). The complementary structures of G and T are C and A, respectively. Thus, determining the C's and A's in both the sample DNA and the antisense strand provides the structure of the sample DNA with a higher confidence (>99%, preferably >99.5% confidence) than determining all four nucleotides A, C, T and G from information collected from the sample DNA only (about 95% confidence). In some embodiments, the nanopore is an alpha hemolysin nanopore, the polynucleotide characterized is a DNA. or RNA, and the electric potential(s) applied in steps (G6 to G7), either in a constant profile or a varied profile is less than about 140 mV, less than about 80 mV, about 0 mV to about 140 mV, preferably less than about 100 mV, less than about 70 mV, more preferably about 0 mV to about 70 mV.

In another example, a two-nucleotide dimer of the structure that is in front of the stopper-test polynucleotide segment in the flow direction of the test polynucleotide can be determined in step (G7). Characterizing the dimers in both the sample DNA and the antisense strand provides the structure of the sample DNA with a higher confidence (>about 97%, or >about 99%, preferably >99.5% confidence) than determining all dimers from the sample DNA only(>about 90%, or >about 95% confidence). In a preferred example, such two-nucleotide dimer is suspending in the constriction site of an alpha hemolysin pore in step (G7).

Another aspect of the present invention relates to a method of obtaining sequence information of multiple single-stranded (ss) test polynucleotides in an array format. "Multiple" refers to more than 1, preferably more than 10, 100, 1,000, 100,000, 1 million, 10 millions, or 100 millions. The method comprises:

(H1) providing multiple nanonpores in an array format and multiple ss test polynucleotides, and H2) for each ss test polynucleotide, performing the steps (F1) to (F2) and (G1) to (G12) as described herein, wherein the nanopore is one of the multiple nanopores, wherein each of the multiple nanopores in the array format is individually addressed and the electric potential applied at each of the multiple nanopores is individually controlled.

Variable Stimulus and Electronic Signatures

Provided herein are systems and methods for identifying a molecule or portion thereof with a nanopore. The method can comprise providing a chip comprising at least one nanopore in a membrane that is disposed adjacent or in proximity to an electrode. The electrode can be adapted to detect a current passing through the nanopore. The method can include inserting a molecule or portion thereof into the nanopore and applying a voltage applied across the nanopore and/or across the membrane. The molecule or portion thereof can affect (and be identified by) the current. It is recognized herein that the current measured at a single voltage may be inadequate to identify the molecule or portion thereof. In an aspect, the methods described herein comprise measuring measuring the current at a plurality of voltages to identify the molecule or portion thereof. In some embodiments, the current at a plurality of voltages comprises an electronic signature and further comprises comparing the electronic signature to a plurality of reference electronic signatures to identify the molecule or portion thereof.

In some embodiments, the portions of the polymer molecule are identified in the sequence at which they are along the length of the polymer molecule and/or the molecules are identified in the order at which the nucleotides are incorporated into the growing nucleic acid chain.

The methods described herein involving measuring current at a plurality of voltages (e.g., obtaining "electronic signatures") can be used with nanopores in any application. For example, molecules can be identified as shown in FIG. 2A. In some cases, the molecule is a polymer molecule (e.g., a nucleic acid molecule, protein, carbohydrate) and portions of the polymer are identified, optionally in the sequence in which they appear on the polymer (e.g., the polymer is sequenced). In some cases, the polymer flows through the nanopore as shown in FIG. 2B. In some cases, the polymer is a nucleic acid molecule and the polymer does not flow through the nanopore. A nucleic acid molecule can be sequenced by passing it adjacent to a nanopore where tag molecules are detected (e.g., as shown in FIG. 2C and FIG. 2D).

In some embodiments, the voltage is varied according to a voltage waveform. The voltage waveform can be any waveform including a square wave, a sinusoidal wave, a triangular wave, a saw-tooth wave, or an irregular wave. FIG. 29 shows some suitable waveforms.

In some instances, the voltage is varied by applying an alternating current (AC) waveform to the nanopore and/or membrane. The AC waveform can have any suitable frequency. In some embodiments, the frequency is about 0.1 hertz (Hz), about 0.5 Hz, about 1 HZ, about 5 Hz, about 10 Hz, about 50 Hz, about 100 Hz, about 500 Hz, about 1000 Hz, about 5000 Hz, about 10000 Hz, about 50000 Hz, about 100000 Hz, about 500000 Hz, or about 1000000 Hz. In some embodiments, the frequency is at least about 0.1 hertz (Hz), at least about 0.5 Hz, at least about 1 Hz, at least about 5 Hz, at least about 10 Hz, at least about 50 Hz, at least about 100 Hz, at least about 500 Hz, at least about 1000 Hz, at least about 5000 Hz, at least about 10000 Hz, at least about 50000 Hz, at least about 100000 Hz, at least about 500000 Hz, or at least about 1000000 Hz. In some embodiments, the frequency is at most about 0.1 hertz (Hz), at most about 0.5 Hz, at most about 1 Hz, at most about 5 Hz, at most about 10 Hz, at most about 50 Hz, at most about 100 Hz, at most about 500 Hz, at most about 1000 Hz, at most about 5000 Hz, at most about 10000 Hz, at most about 50000 Hz, at most about 100000 Hz, at most about 500000 Hz, or at most about 1000000 Hz.

In some instances, the voltage is varied such that the molecule or portion thereof is identified with high statistical confidence. In some instances, the molecule or portion thereof is identified with a statistical confidence of about 90%, about 95%, about 99%, about 99.9%, about 99.99%, or about 99.999%. In some instances, the molecule or portion thereof is identified with a statistical confidence of at least about 90%, at least about 95%, at least about 99%, at least about 99.9%, at least about 99.99%, or at least about 99.999%.

In some cases, the chip comprises a plurality of nanopores adjacent or in proximity to a plurality of electrodes and the electrodes (i) are individually addressed, (ii) the voltage applied is individually controlled, or (ii) both (i) and (ii). The voltage can be varied over any suitable range including from about 120 mV to about 150 mV or from about 40 mV to about 150 mV.

The molecule can be a double stranded nucleic acid molecule, in which case the molecule can be dissociated to form one or more single-stranded nucleic acid molecules, and the one or more single-stranded nucleic acid molecules can be passed through the nanopore to determine the sequence of the double stranded nucleic acid molecule. Examples of nanopores include the alpha hemolysin nanopore and the Mycobacterium smegmatis (MspA) nanopore.

In some instances, the rate of passage of the polymer molecule through the nanopore is slowed with the aid of one or more speed bump molecules where portions of the polymer molecule are identified when the rate of passage of the polymer molecule is slowed. In some embodiments, an individual speed bump molecule comprises ribonucleic acid.

In some embodiments, the polymer molecule is trapped in the nanopore (e.g., the polymer molecule is a single stranded nucleic acid molecule and the molecule is trapped in the nanopore by bulky structures formed on either side of the nanopore). The polymer molecule can be threaded back and forth through the nanopore to identify portions of the polymer molecule a plurality of times (e.g., 2, 3, 4, 5, 6, 7, 8, 9, 10, or more times).

A nucleic acid hairpin is ligated to an end of the double stranded nucleic acid molecule in some cases to provide a single-stranded nucleic acid molecule comprising the sense and anti-sense strands of the double stranded nucleic acid molecule upon dissociation of the double stranded nucleic acid molecule.

In an aspect, the present invention is directed to a method for obtaining sequence and/or structure information of a test polymer using a nanopore detector. The test polymer can be trapped in or reside in the nanopore for a dwelling time (optionally by a stopper-test polymer segment). During this dwelling time, a varied electric potential profile comprising electric potentials having more than one voltage can be applied to the electrodes of the nanopore detector and a set of electrical signals may be obtained. The electrical signals collected under the varied electric potential profile may provide more distinctive information of the sequence and/or structure (e.g., that is in front of the stopper-test polymer segment in the flow direction of the test polymer) compared to the electrical signals collected under a constant electric potential. Thus, the electrical signals collected under the varied electric potential profile may provide a more reliable and accurate determination of the test polymer sequence and/or structure than previous methods that use a constant electric potential.

One aspect of the present invention relates to a method of obtaining sequence and/or structure information of a test polymer, comprising:
 (I1) providing a test polymer complex comprising a stopper-test polymer segment;
 (J1) applying a first test electric potential to flow the test polymer complex through a nanopore of a nanopore detector until the stopper-test polymer segment is stalled, slowed or stopped before a constriction area of the nanopore,
 (12) applying a varied electric potential profile comprising electric potentials having more than one voltages to the electrodes of the nanopore detector when the stopper-test polymer segment is stalled inside the nanopore for a dwelling time and obtaining a first set of electrical signals, and
 (13) determining the structure that is in front of the stopper-test polymer segment in the flow direction of the test polymer by comparing the first set of electrical signals with electrical signals collected under the same varied electric potential profile in step (12) for a known structure that is in front of the stopper-test polymer segment in the flow direction of the test polymer.

In an embodiment, the test polymer is a test polynucleotide, and the building blocks are nucleotides as described herein. In an embodiment, the test polynucleotide has 1 to about 10,000 bases, 1 to about 1,000 bases, 1 to about 500 bases, 1 to about 300 bases, 1 to about 200 bases, 1 to about 100 bases, about 5 to about 10,000 bases, about 5 to about 1,000 bases, about 5 to about 500 bases, about 5 to about 300 bases, 5 to about 200 bases, 5 to about 100 bases, 10 to about 10,000 bases, 10 to about 1,000 bases, 10 to about 500 bases, 10 to about 300 bases, 10 to about 200 bases, 10 to about 100 bases, 20 to about 10,000 bases, 20 to about 1,000 bases, 20 to about 500 bases, 20 to about 300 bases, 20 to about 200 bases, 20 to about 100 bases, 30 to about 10,000 bases, 30 to about 1,000 bases, 30 to about 500 bases, 30 to about 300 bases, 30 to about 200 bases, 30 to about 100 bases, 30 to about 50 bases, 50 to about 10,000 bases, 50 to about 1,000 bases, 50 to about 500 bases, 50 to about 300 bases, 50 to about 200 bases, or 50 to about 100 bases.

The stopper can be an oligonucleotide speed bump, and the ss test polynucleotide can comprise a section of ss polynucleotide that is to be bound by the speed bump in a method described herein. In some embodiments, the test polynucleotide is a test DNA or RNA, and the speed bump is a DNA or RNA speed bump. A speed bump can have a length of 2, 3, 4, 5, 6, 7, 8, 9, 10, 11, 12, 13, 14, 15, or 16 bases. In some cases the speed bump has 10 or less, 8 or less, 6 or less, or 4 or less bases. The speed bump may comprise one or more nucleotides selected from the group consisting of universal nucleotides, locked nucleotides, primary nucleotides, modifications thereof, and combinations thereof. Modifications of universal nucleotides, and primary nucleotides include modifications at the nucleobase structures, the backbone structures (e.g., glycol nucleotides, morpholinos, and locked nucleotides) and combinations thereof. In another preferred embodiment, the backbone structures of the speed bump is modified (e.g., glycol nucleotides, morpholinos, and locked nucleotides) at designated position(s), random positions or combinations thereof. In some embodiments, the first base pair of the speed bump-test polynucleotide segment may be partially or completely in the nanopore and contributes to the electrical signals obtained in step (12). Thus, step (13) further comprises obtaining sequence and/or structure information of the first base pair of the speed bump-test polynucleotide segment in the flow direction of the ss test polynucleotide. In some embodiments, it is preferred to construct the speed bumps to have a universal nucleotide which base-pair with all primary nucleobases (A, T, C, G and U) at the 5' and/or 3' end to normalize the contribution of the first base pair of the speed bump-test polynucleotide segment and makes the signals easier to analyze.

The stopper can be an enzyme that binds to the ss test polynucleotide and optionally moves the ss test polynucleotide through the nanopore. Examples of such enzymes include, without limitation, Kienow, exo minus, Phi29 polymerase, Phi29, exo minus polymerase, T4 DNA polymerase; M-MuLV Rever Transcriptase; and T7 Gp4a Helicase.

The stopper can be a part of the test polynucleotide that can form a 2-D or 3-D structures such as polynucleotide hairpin structures, multi-hairpin structures and multi-arm structures. In some embodiments, the first base pair of the stopper-test polynucleotide segment may be partially or completely in the nanopore, the electrical signals obtained in step (12) step (13) further comprising determining the first base pair of the stopper-test polynucleotide segment in the flow direction of the ss test polynucleotide.

In some embodiments, the structure in front of the stopper-test polynucleotide segment determined in step (13) is a 1, 2, 3, 4, 5, 6, 7, 8, 9, 10, 11, 12, 13, 14, 15, 16, 17, 18, 19, 20 to 50 bases, 50 to 100 bases, 100 to 200 bases, 200 to 500 bases, or greater than a 500 base sequence.

In some embodiments, the structure in front of the stopper-test polynucleotide segment determined in step (13) is any nucleotide sequence at position 1-50, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or a combination thereof from the stopper-test polynucleotide segment.

In some embodiments, the varied electric potential profile applied in step (12) comprises electric potentials having two or more voltages each applied for a time. In some embodiments, the varied electric potential profile comprises one or more electric potentials resulted during step (JI) or after the stopper-test polymer complex is stalled, slowed or stopped in the nanopore in step (JI). At least two electric potentials of the two or more electric potentials applied have a difference of more than about 1 mV, 5 mV, 10 mV, or 30 mV. In an embodiment, the electric potentials have a voltage of about 160 mV to about −160 mV, about 160 mV to about OmV, about 160 mV to about 60 mV, about 100 mV to about OmV, 100mV to about 80 mV, or 80 mnV to about 70 mV. The time for each electric potential is at least about 5 µs, at least about 10 µs, at least about 50 µs, at least about 100 µs, at least about 500 µs, at least about 1 ms, at least about 5 ms, at least about 10 ms, at least about 50 ms, at least about 100 ms, at least about 500 ms, at least about 1 s, or at least about 2 s.

In some embodiments, the varied electric potential profile applied in step (12) comprises an electric potential ramp changing from a first electric potential to a second electric potential over a time period. In some embodiments, the varied electric potential profile comprises one or more electric potentials resulted during step (JI) or after the stopper-test polymer complex is stalled, slowed or stopped in the nanopore in step (JI). For example, the first electric potential of the varied electric potential profile can be an electric potential resulted during step (JI) or after the stopper-test polymer complex is stalled, slowed or stopped in the nanopore in step (JI). The difference between the highest electric potential and the lowest electric potential of the varied electric potential profile is more than about 1 mV 5 mV, 10 mV 20 mV, or 30 mV. In another embodiment, the first electric potential is about 160 mV and the second electric potential is about −160 mV. In an embodiment, the first electric potential is about 160 mV and the second electric potential is about 60 mV. In another embodiment, the first electric potential is about 100 mV and the second electric potential is about 0 mV. In another embodiment, the first electric potential is about 160 mV, the second electric potential is about 0 mV. In another embodiment, the first electric potential is about 100 mV and the second electric potential is about 80 mV. In another embodiment, the first electric potential is about 100 mV and the second electric potential is about 90 mV. In another embodiment, the first electric potential is about 90 mV and the second electric potential is about 85 mV. The predetermined time period is at least about 5 µs, at least about 10 µs, at least about 50 µs, at least about 100 µs, at least about 500 µs, at least about 1 ms, at least about 5 ms, at least about 10 ms, at least about 50 ms, at least about 100 ms, at least about 500 ms, at least about 1 s, or at least about 2 seconds.

In some embodiments, the varied electric potential profile applied in step (12) comprises an electric potential waveform changing from a first electric potential to a second electric potential to a third electric potential and so on to a plurality of electric potentials that in total form a varying applied electric potential waveform.

In some embodiments, step (12) is performed in a solution having at least 0.1 M salt. The salt is selected from the group consisting of chloride, phosphate, nitrate and sulfate.

In some embodiments, step (12) is performed in a solution having a pH of about 6.5 to about 8.5 or from about 7 to about 8. Any buffer that can provide such pH can be used. Examples include, without limitation, HEPES buffer. In some embodiments, the nanopore is an alpha hemolysin nanopore or a MspA nanopore.

In some embodiments, the nanopore detector comprises at least one metal electrode embedded in an isolation surface. Examples of the materials the metal electrode comprises include, without limitation, silver, sliver chloride, platinum, gold, ruthenium and nickel. Examples of the materials the isolation surface comprises include, without limitation, a plastic material (e.g., Teflon), a glass, or a semiconductor material (e.g., silicon, germanium, and gallium). In some embodiments, the isolation surface is further modified to be hydrophobic and lipophilic using methods known in the art to facilitate attachment of biological molecules to the isolation surfaces. For example, further silanization with silane molecules containing 6 to 20 carbon-long chains (e.g., octadecyl-trichlorosilane, octadecyl-trimethoxysilane, or octadecyl-triethoxysilane) or DMOCs can be done on silicon dioxide surface on a silicon surface.

Another aspect of the present invention relates to a method of obtaining sequence information of multiple single-stranded (ss) test polynucleotides in an array format. "Multiple" refers to more than 1, preferably more than 10, 100, 1,000, 100,000, 1 million, 10 millions, or 100 millions. The method comprises:

(K1) providing multiple nanonpores in an array format and multiple ss test polynucleotides, and (K2) for each ss test polynucleotide, performing the steps as described herein, where the nanopore is one of the multiple nanopores and each of the multiple nanopores in the array format is individually addressed and the electric potential associated with each of the multiple nanopores is individually controlled.

Figure 30:
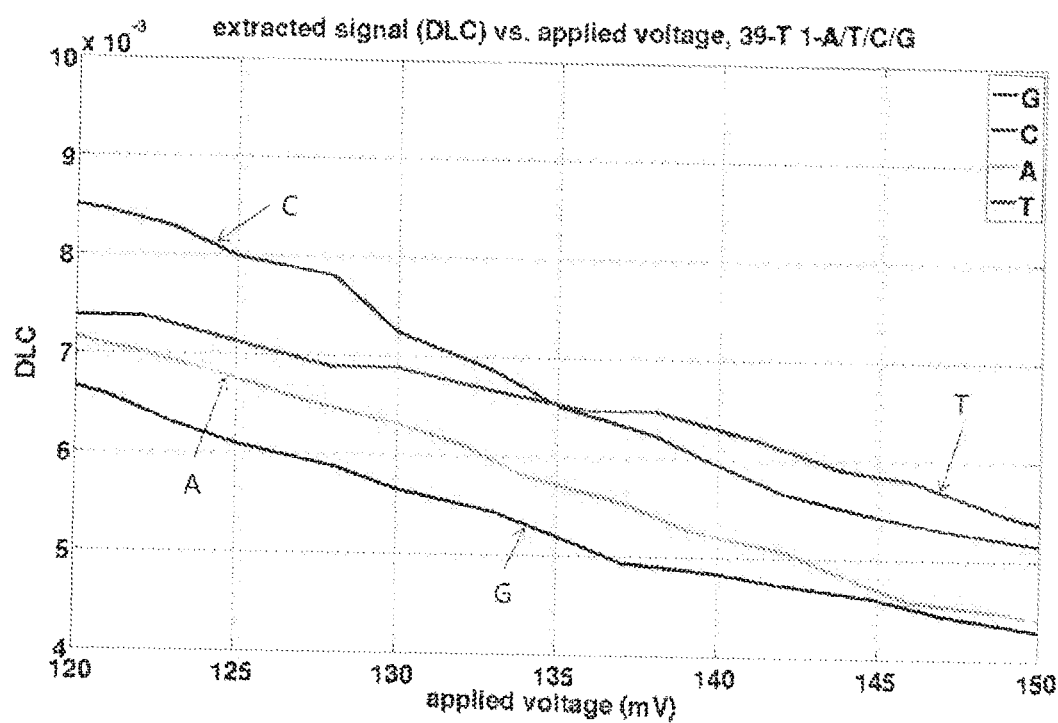
FIG. 30 shows a plot of extracted signal versus applied voltage for the four nucleic acid bases adenine (A), cytosine (C), guanine (G) and thymine (T)
Figure 31:
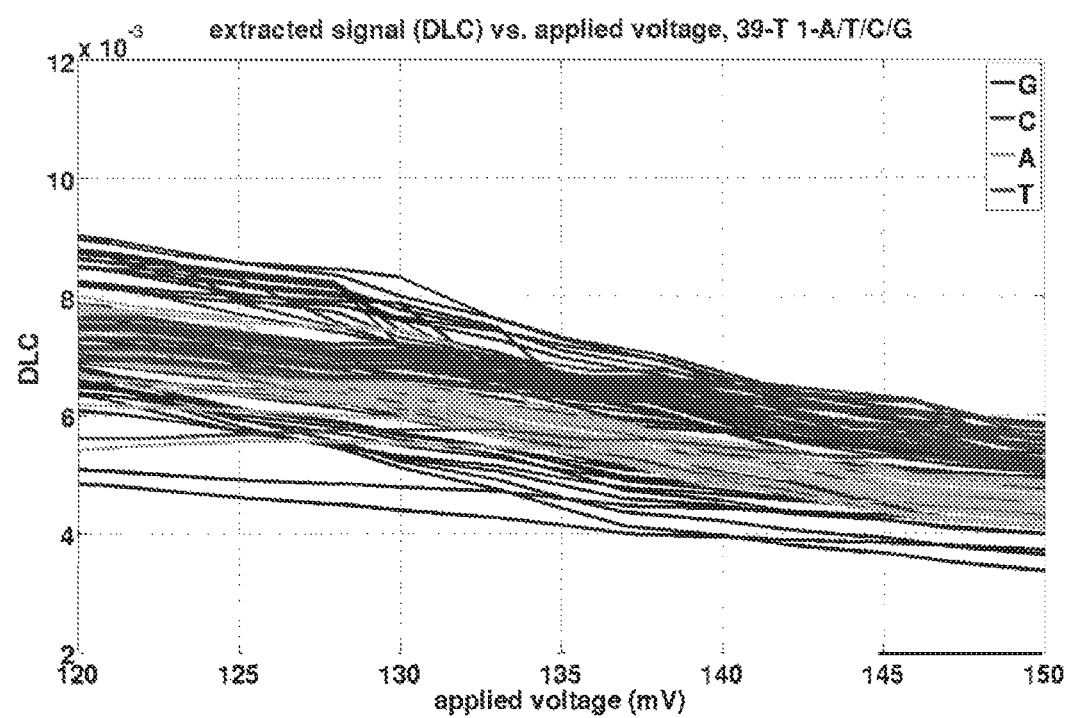
FIG. 31 shows a plot of extracted signal versus applied voltage for multiple runs of the four nucleic acid bases adenine (A), cytosine (C), guanine (G) and thymine (T)
Figure 32:
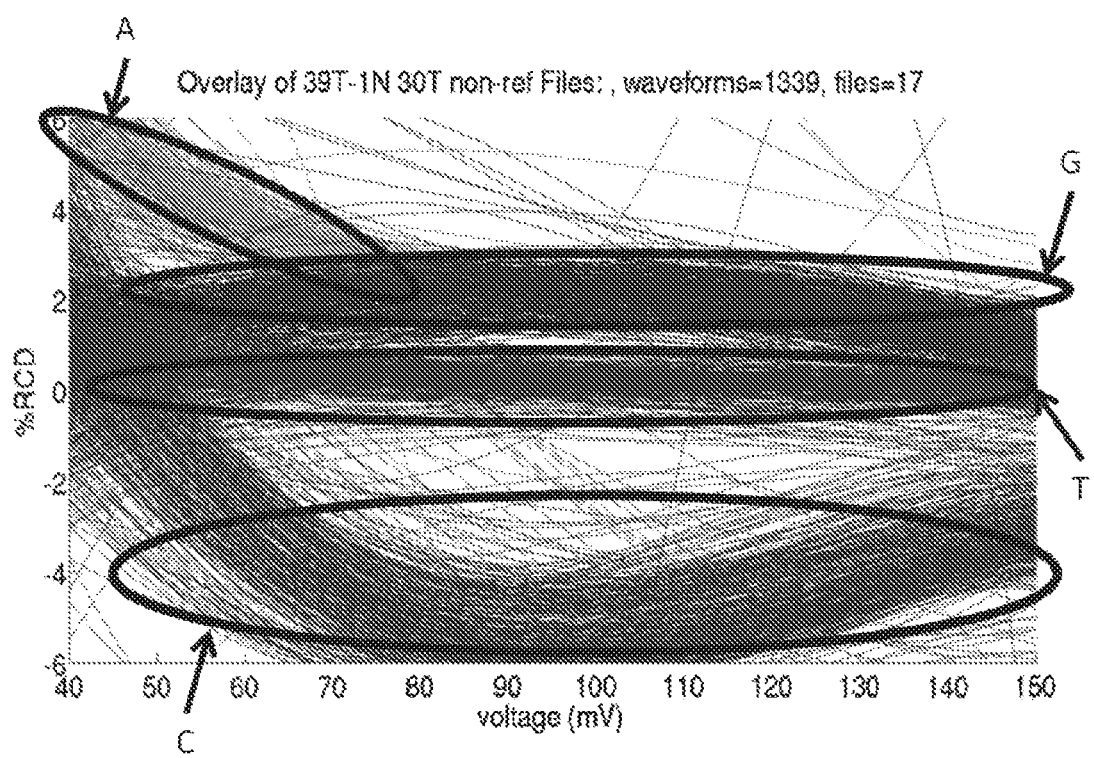
FIG. 32 shows a plot of percent relative conductive difference (¾RCD) versus applied voltage for multiple runs of the four nucleic acid bases adenine (A), cytosine (C), guanine (G) and thymine (T).

By way of example, FIGS. 30-32 show the response to varied applied voltage for nucleotides. The methods and concept of varied applied voltage and/or electronic signatures can be used to distinguish tag molecules (e.g., attached to tagged nucleotides).

FIG. 30 shows the extracted signal (DLC) versus applied voltage for the nucleotides adenine (A), cytosine (C), guanine (G) and thymine (T). FIG. 31 shows the same information for a plurality of nucleotides (many experimental trials). As seen here, cytosine is relatively easy to distinguish from thymine at 120 mV, but difficult to distinguish from each other at 150 mV (e.g., because the extracted signal is approximately equal for C and T at 150 mV). Also, thymine is difficult to distinguish from adenine at 120 mV, but relatively easier to distinguish at 150 mV. Therefore, in some cases, the applied voltage can be changed (e.g., as part of a voltage sweep) from about 120 mV to 150 mV to distinguish each of the nucleotides A, C, G and T (or U).

FIG. 32 shows the percent relative conductive difference (¾RCD) as a function of applied voltage for the nucleotides adenine (A), cytosine (C), guanine (G) and thymine (T). Plotting ¾RCD (which is essentially the difference in conductance of each molecule referenced to a 30T reference molecule) can remove of f set and gain variation between experiments. FIG. 32 includes individual DNA waveforms from the first block of 17/20 Trials. The ¾RCD of all single nucleotide DNA captures from number 50 to 200 for all 17 good Trials. Voltages where each of the nucleotides are distinguishable are indicated.

EXAMPLES

Example 1

PB2 Structure (1)

Figure 24:
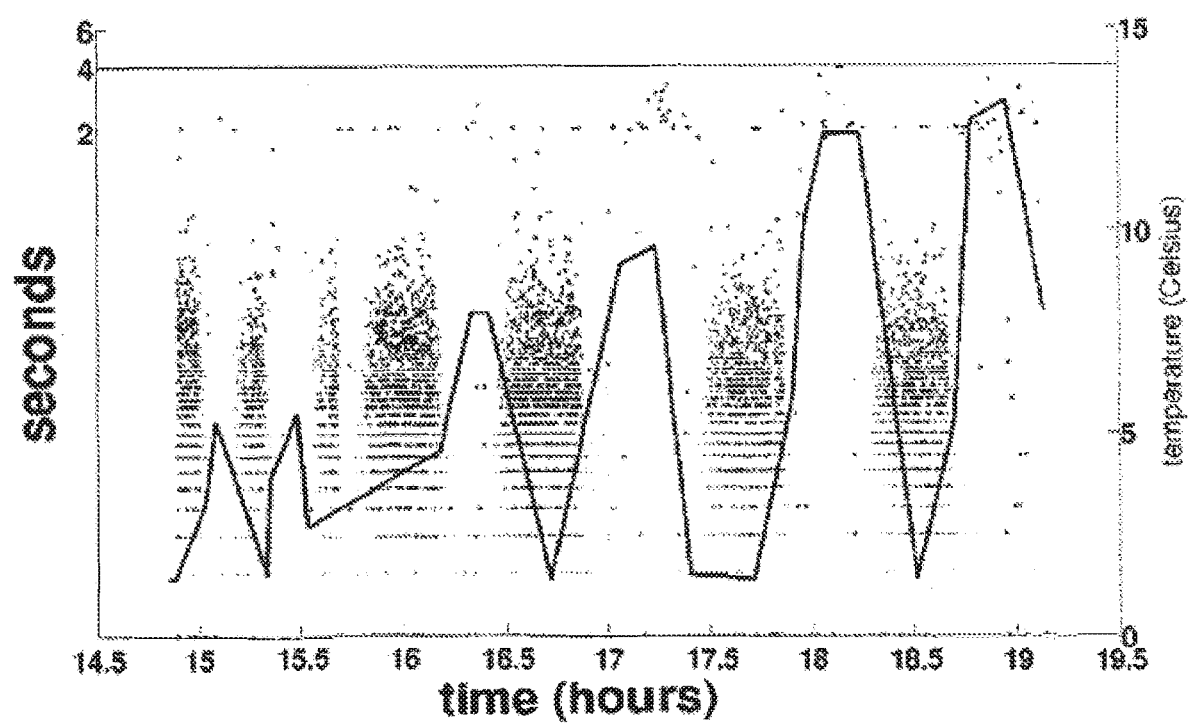
FIG. 24 illustrates the relationship between working temperature and capture of a ss test polynucleotide having BS2-1 on one end and a BS 1 on the other end in a nanopore.

A ss test DNA having a BS2 on one end is captured in a nanopore at a temperature lower than T2 and released at a temperature higher than T2 (FIG. 24).

The BS2 (BS2-1) is a DNA 5-base duplex hairy in structure formed from a PB2 having a sequence of 5'-CCCCC CCCCC TTATA CCCCT ATAA-3' (SEQ ID NO. 1, PB2-1). BS2-1 had melting temperature of about 15° C., and a G of about −0.96 kcal/mol at 5° C. according to the simulation using UNAFOLD program. This moderately low G indicated that BS2-1 had a relatively low binding energy.

In FIG. 24, the solid line showed the change in temperature from 2° C. to 14° C. The dots represented individual DNA captures, meaning that PB2-1 formed BS2-1 at the corresponding temperature and is captured in the nanopore. The captures were present when the temperature is about or lower than T2 (about 5° C.), indicating that BS2-1 is formed from PB2-1 and the DNA is stalled in the nanopore. The capture of the DNA disappeared when the temperature increased to about 5 to 10° C. over T2, indicating that BS2-1 melted and is no longer stalled in the nanopore.

Thus, PB2-1 formed BS2-1 which stalled, slowed or stopped the ss DNA in the pore at a temperatures about 10° C. lower than its melting temperature. This may be due to the relatively low G BS2-1 had. Thus, the DNA duplex structure in BS2-1 is relatively easy to dissociate in the nanopore. Thus, a BS2 having a higher G may be more difficult to destruct and may provide longer dwelling time at the nanopore at a temperature closer to the melting temperature of the BS2.

Example 2

PB1 and PB2 Structure (11)

A PM forms a BS1 at a first temperature (T1) that is higher than the second temperature (T2) at which a BS2 is formed from a PB2. T2 is higher than a working temperature (Tw). In this example, Tw is below room temperature. Thus, PB 1 is designed to have a relative long DNA duplex segment (either in a DNA duplex with an anti-sense DNA segment, or in a hairpin structure) such that the desired melting temperature of the relative long DNA duplex segment is achieved.

PB2 is designed to have a lower melting temperature and a high binding energy (G=about −1 to −5 kcal/mol, about −4 to −6 kcal/mol, about −4 to −5 kcal/mol, about −4.5 kcal/mol, or about −4.0 kcal/mol at the working condition). A molly bolt or branched molecule has been designed to provide a BS2 having low T2 while not readily dissociated at the working condition.

An example of PB1 has a sequence of 15 bases and a 4 base A loop; 5'-CGTCT AGCGT TGCCG AAAAC GGCAA CGCTA GACG-3' (SEQ ID NO. 2, PB1-1). This sequence has a melt temperature of 91.4° C. in 1 M KCl, and 1 µM sequence concentration according to the simulation using UNAFOLD program.

An example of PB2 has a sequence of 5'-GACCC TGCCC CCAGC TTTCC CCAAA CGTCA AAAAA-3' (SEQ ID NO. 3, PB2-2) and the formed BS2-2 is a 3 stem, 3 duplex, 2 loop molecule as shown below according to the simulation using UNAFOLD program:

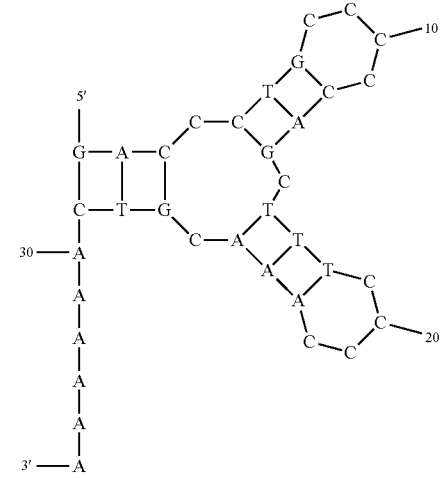

BS2-2

The following characteristics of the BS2-2 were provided using UNAFOLD program:
G=−4.5140 kcal/mol at 5° C. (100% folded),
H=−67.90 kcal/mol,
S=−227.9 cal/(K·mol) and
Tm=24.8083° C.

A calculated melting curve of BS2-1 is obtained using nearest neighbor basis. The melting curve illustrates that at above 30° C. about 90% of the structures are linear (PB2-2) and at below 20° C. about 90% of the structures form BS2-2. Such a steep melting curve shows well controlled bulky structure formation of BS2-2, which is highly desired. The G of BS2-2 at 5° C. is −4.5 kcal/mol, which indicates a stronger binding affinity than the 5 base hairpin molecule BS2-1 in Example 1.

Example 3

Stalling DNA by 4-Base Duplex Segments

This example illustrates a 4-base duplex segment stalled the ss test DNA in a nanopore for a dwelling time sufficient to obtain desired sequence information.

The test DNAs were the following:

A test DNA is formed by self-hybridization of :DNA-1: 5'-CCCCC CCCCC GCGC-3' (SEQ ID NO. 4). DNA-I is dissolved in biology grade water, heated to 90° C. and then left to cool to room temperature for self-hybridization, A DNA-I molecule hybridize with another DNA-I molecule to form a self-hybridized DNA-I structure having a 4-base GCGC duplex segment at the 3' ends and two overhanging ss 10-C tails at the 5' ends thereof. At the working condition, the self-hybridized DNA-I structure entered a nanopore with one of the two overhanging ss 10-C tails, stalled in the nanopore by the 4-base duplex segment at the 3' end for a dwelling time, and then when the 4-base duplex segment dissociated, the self-hybridized DNA-I structure is converted to two ss DNA-I molecules which went through the nanopore like ss test DNAs. Thus, when flowing through a nanopore, the self-hybridized DNA-I structure simulated as test DNA having a 4-base duplex segment formed by a speed bump and the ss test DNA.

Another test DNA, self-hybridized DNA-2 structure, is formed by self-hybridization of DNA-2: 5'-TTTTT TTTTT GCGC-3' (SEQ ID NO. 5) using the same process described herein regarding the formation of the self-hybridized DNA-I. The self-hybridized DNA-2 structure had a 4-base GCGC duplex at the 3' ends and two overhanging ss 10-T tails at the 5' ends.

Another test DNA is streptavidin-DNA-3 complex formed by incubation of DNA-3: 5'-TTTTT TTTTT TTTTT TTTTT TTTTT TTTTT TTTTT TTTTT-biotin-3' (SEQ ID NO. 6) and streptavidin at a condition described below. When flowing through a nanopore under a electric potential, streptavidin-DNA-3 complex stalled in the nanopore until the electric potential is changed/reversed. Thus, streptavidin-DNA-3 complex served as a positive control showing that the nanopore detector system is working properly. The dwell time of this molecule is relatively long.

The working condition is 20 mM HEPEs buffer and 1 M KCI at 0° C. The electric potential applied is about 128 mV.

The nanopores were created from 10 ng/mL alpha hemolysin deposited onto the surface of a bilayer at a final concentration of 02 ng/mL and with the application of electrical stimulus as described in U.S. Patent Application :Publication No. 2011/0193570, which is entirely incorporated herein by reference. The bilayers were created with the painting method from 10 mg/mL of DPhPC in Decane across the essentially planar AgCl electrode on a Teflon surface as described in U.S. Application Publication No. 2011/0193570.

Self-hybridized DNA-I (2 µM), self-hybridized DNA-2 (2 µM), DNA-3 (2 µM), and streptavidin (1 µM) were incubated with multiple nanopores constructed as described herein for about 2 hours at the working condition described herein in this example. An electric potential of about 128 mV i s applied to the nanopore and electrical signals are collected. The electrical signals show that the 4-base duplex segments are able to stall DNA-I and DNA-2 in the nanopore for a dwelling time of about 100 ms to 200 ms. These data show that speed bumps as short as 4 bases work to stall a as test DNA long enough to obtain relevant sequence information.

Example 4

Stalling DNA by 6-Base Random Speed Bump Pool

This example illustrates a 6-base random speed bump pool successfully bound to, stalled in a nanopore detector and dissociated from a test DNA.

In this example, the ss test DNA is as female genomic DNA. The random speed bump pool comprised hexamer DNA oligonucleotides having all combinations of the primary DNA nucleotides, which is purchased from Invitrogen.

The working condition is 20 mM HEPEs buffer and 1 M KCI at 0° C. The electric potential applied is about 128 mV.

The nanopores are created from 10 ng/mL, alpha hemolysin deposited onto the surface of a bilayer at a final concentration of 0.2 ng/mL and with the application of electrical stimulus as described in U.S. Patent Application Publication No. 2011/0193570, which is entirely incorporated herein by reference. The bilayers are created with the painting method from 10 mg/mL of DPhPC in Decane across the essentially planar AgCl electrode on a Teflon surface as described in U.S. Patent Application Publication No. 2011/0193570, which is entirely incorporated herein by reference.

The ss test DNA (1 µM) is incubated with the 6-base random speed bump pool (100 µM) are incubated with multiple nanopores constructed as described herein for about 2 h at the working condition described herein in this example. An electric potential of about 128 mV i s applied to the nanopore and electrical signals are collected. The signals showed that the 6-base random speed bump pool is able to bind to the as test DNA, stall the ss test DNA in the nanopore long enough to obtain relevant sequence information, and dissociate from the ss test DNA as described herein.

Example 5

Preparation of a Test Polynucleotide Comprising Sample Polynucleotide and Antisense Polynucleotide Thereof A. The Sample Polynueleatide is a ds Sample DNA The double-stranded (ds) test polynucleotide can be formed by conventional DNA ligation techniques. The ds sample polynucleotide can be ligated with the duplex section of Linker section and the duplex section of the Pre-bulky Section as shown in FIG. 28. Then the ds test polynucleotide can be denatured (e.g., heating) to provide the ss test polynucleotide (FIG. 28).

B. The Sample Polynucleotide is a ss Sample DNA

A ds sample DNA can be prepared from the ss sample DNA using conventional methods well known in the art. Then the ds sample DNA can be further processed according to the method described herein with regard to ds sample DNA.

C. The Sample Polynucleotide is as Sample RNA

A ds sample DNA-RNA hybrid can be prepared from the ss sample RNA using conventional methods well known in the art. Then the ds sample DNA-RNA hybrid can be further processed according to the similar method described herein with regard to ds sample DNA.

D. Enzymatic Approach in Preparing a ds Testpolynucleotidefrom a ss Sample Polynucleotide (ss DNA or ss RNA)

If the sample provided is ds DNA, the ds DNA can be denatured to provide ss sample DNA's to be used in this enzymatic approach:

DI) ligating specific hook primer to 3' end of the ss sample polynucleotide, wherein the hook shaped primer comprises a hairpin structure, a section of 3' overhang that can form a duplex section with the 3' end of the ss sample polynucleotide. If the structure of the sample polynucleotide is totally unknown, the 3' overhang of the hook primer can comprise a few universal nucleotides (e.g., 2, 3, 4, 5, 6, 7, or 8 nucleotides or more) that can interact with any oligonucleotide sequences.

D2) The 5' end of the hook primer may have a gap from the 3' end of the ss sample polynucleotide, which can be ligated/filled in with an enzyme in single temperature extension reaction known in the art.

D3) The polynucleotide obtained from step D2) has a hairpin structure on one end and a single strand section on the other end. The single strand section is used as the template to elongate the polynucleotide from the 3' end of the hook primer with an enzyme in single temperature extension reaction known in the art. When the elongation is complete, the polynucleotide has a blunt end at one end and a hairpin at the other end.

D4) The polynucleotide obtained from step D3) is ligated with the pre-bulky section shown in FIG. 28 by blunt-end ligation. If the pre-bulky section has a biotin attachment, the obtained polynucleotide can be isolated by attachment of biotin to magnetic streptavidin beads. Other types of interactions can also be used, e.g., antibody-antigen interaction, to isolate the desired polynucleotides.

D5) The desired polynucleotides are separated and removed from streptavidin bead and denatured into the corresponding ss test polynucleotides if necessary.

The method of using a specific hybridization sequence in the hairpin primer and using a biotin molecule attached to one or more of the pre-bulky structures blunt-end ligated to the newly created duplex sample provides a method to selectively enrich a sample for the specific sample fragments that are targeted by the hairpin primer. When using universal polynucleotides in the hairpin primer molecule a single hairpin primer or only a few variant hairpin primers can be used to create sense/antisense samples from all the strands in a sample. Such a method may lose information about the corresponding antisense structure at the 3' end of the sample but it makes the creation of a prepared sample from a large collection of different nucleic acid molecules possible.

E. Enzymatic Approach in Preparing ads Testpolynucleotidefrom as Sample Polynucleotide (ss DNA or ss RNA) by ss Ligation E1. Ligation of sample facilitated by an adaptor.

A) facilitated by an adaptor

A ss sample polynucleotide is hybridized with a specific primer (adaptor) or a universal adaptor onto the 3' end of the sample molecule so that a 5' overhang exists on the hybridized adaptor. To this overhang end of the adaptor is ligated another polynucleotide comprising a hairpin structure and constructed so that the 3' end of the hairpin comes in contact with the 5' end of the adaptor and the 5' of the hairpin comes in contact with the 3' end of the original ss sample polynucleotide. The adaptor contains an overhang section that may contain nucleotides defined herein that bind specifically to a separate molecule that is fully or partially a hairpin nucleic acid strand. The adaptor may also contain portions of specific sequence to a particular sample strand sequence, or it may contain a random sequence that when made into a library of adaptors can bind to any sample strand, or it may contain universal bases or combinations of normal bases and universal bases that allow the adaptor to bind to any sample strand. These potential combinations of nucleotides are important because they allow enrichment of a sample for specific sequences in the case of using specific nucleotides in the adaptor or they allow universal creation of sense/antisense strands from all sample single stranded nucleic acids in a sample. In any case, the overhang portion of the adaptor may be created to bind to man-made DNA but not natural DNA so that only the added hairpin molecule with its overhang and that has appropriate complementary nucleic acids or nucleic acid analogues will bind to the hairpin or partial hairpin molecule. This may be accomplished, for example, by the use of isodG and isodC nucleotides. The full hybridized complex can then be ligated together at the two locations above and the molecule is ready for antisense extension.

A ss sample polynucleotide may also be turned into a sense-antisense representation with select pre-bulky structures attached to the ends of the molecule by adapter and hairpin hybridization, sample strand and hairpin ligation, adaptor melt-off, extension, and blunt end ligation. The adaptor will contain an overhang section that may contain natural or man-made nucleotides that will bind specifically to a separate molecule that is fully or partially a hairpin nucleic acid strand. The adaptor may also contain portions of specific sequence to a particular sample strand sequence, or it may contain a random sequence that when made into a library of adaptors can bind to any sample strand, or it may contain universal bases or combinations of normal bases and universal bases that allow the adaptor to bind to any sample strand. In any case, the overhang portion of the adaptor may be created to bind to man-made DNA but not natural DNA so that only the added hairpin molecule with its overhang and that has appropriate complementary nucleic acids or nucleic acid analogues will bind to the hairpin or partial hairpin molecule. This may be accomplished, for example, by the use of isodG and isodC nucleotides.

The adaptor molecule may also be created so that the 5' end of the adaptor nucleic acid strand does not contain the needed tri-phosphate group for ligation to occur. In this instance, the adaptor will still serve its intended function of hybridizing to the ssDNA or ssRNA sample and hybridizing to the hairpin molecule and thus bringing the two molecules into close proximity for ligation to occur. Without the appropriate phosphate group however, the ligation of the adaptor and hairpin will not occur. Ligation will occur at the end of the sample molecule and the hairpin, but not between the hairpin and the adaptor. This is satisfactory because the adaptor can then be melted of f and the subsequent fill in reaction can still proceed from the 3' of the newly ligated hairpin molecule that presents the appropriate double stranded 3' end to the extension enzyme for the extension reaction. This is advantageous because the newly created antisense strand will now contain antisense nucleotides corresponding to all of the original sample sense strand. B) Single-strand ligation not facilitated by an adaptor.

The creation of a linked sense sample strand and a new antisense strand can also be accomplished by single stranded ligation of ss sample polynucleotide and a hairpin nucleic acid comprising an overhang that is single stranded. T4 Ligase commercially available can link two separate single stranded portions of polynucleotides. Subsequent fill in and blunt end ligation of pre-bulky structures and denaturing (e.g., melting) will create a sense/antisense prepared molecule.

All of the above sample preparation methods are ideal for single molecule detection and sequencing. Especially for nanopore sequencing using an array of individually controlled electrodes, each electrode controlling an applied and read stimulus to a nanopore. Multiple electrode/nanopore sensors can be combined into an array of individually controlled electrode/nanopore sensors on a planar or three dimensional surface such as may constructed on or in a semiconductor material using techniques familiar to the art in the semiconductor field.

Following ligation of the hairpin to the single stranded sample nucleic acid strand the following details examples of completing the prepared sense/antisense/pre-bulky structure sample molecule for nanopore sequencing and or detection.

E2) The antisense strand is synthesized by a fill-in enzyme like Kienow from the polynucleotide obtained from step (E1) to provide a polynucleotide having a hairpin structure on one end and a blunt end on the other.

E3) The polynucleotide obtained from step E2) is ligated with the pre-bulky section shown in FIG. 28 by blunt-end ligation. If one or more strands of the pre-bulky structure has a biotin attachment, the obtained polynucleotide can he isolated by attachment of biotin to magnetic streptavidin beads. Other types of interactions can also be used, e.g., antibody-antigen interaction, to isolate the desired polynucleotides.

E4) The desired polynucleotides are separated and removed from streptavidin bead and denatured into the corresponding ss test polynucleotides i f necessary.

Example 6

Single Nucleotide Differentiation is Obtained with a Greater than 99% Confidence by DNA Nanopore Detection DNA-TA (5'-TTTTTTTTTTTTTTTTTTTTTTTTTTTT-ATTTTTTTTTT-Biotin-3'), DNA-TT(5'-TTTTTTTTTT-TTTTTTTTTTTTTTTTTTTTTTTTTTTT-Biotin-3'), DNA-TC (5'-TTTTTTTTTTTTTTTTTTTTTTTTTTTC-TTTTTTTTTT-Biotin-3'),DNA-TG(5'-TTTTTTTTTTTT-TTTTTTTTTTTTTTTTGTTTTTTTTTTTT-Biotin-3'), and DNA-TR containing 30T (5'-TTTTTTTTTTTTTTTTTTTT-TTTTTTTTTT-Biotin-3') are synthesized. Each type of DNA (DNA-TA, DNA-TT, DNA-TC, DNA-TG and DNA-TR) is mixed individually with Streptavidin to a working concentration of 100 µM of DNA and 25 µM of Streptavidin. The obtained solutions are then further diluted to a final concentration of 4 µM of test DNA and 1.0 µM of Streptavidin as DNA stock solutions.

The tests are run on alpha hemolysin nanopore detectors. The nanopore detectors had a pair of silver electrodes embedded in a planar Teflon surface. Lipid bilayers are created by a bubble method or by sliding a pipette tip dipped in a small amount of lipid mix across the surface of the planar electrode using 1 µL of 15 mg/mL DPhPC lipid in Decane. Nanopores are prepared with up to 1 µL of 1 µg/mL Alpha Hemolysin in 20% Glycerol and water buffered to pH 8.0 with 20 mM HEPES. Alternatively, the nanopores are prepared with 1 to 100 ng/mL of alpha hemolysin porin.

In one experiment, 2 µL stock solution of the reference DNA, a homopolymer 30T with Streptavidin attached to the 3' end (DNA-TR) and 2 µL stock solution of a test DNA selected from (DNA-TA, DNA-TT, DNA-TC or DNA-TG) are mixed with 40 µL of 1.25 M KCl, pH 8.0, 20 mM HEPES buffered, double filtered solution and 4 µL of biology grade water are loaded on a nanopore detector prepared herein. The varied electric potential profile is applied by an external waveform generator, and the current flowing through the nanopore is recorded. An initial electric potential of 160 mV is applied to the electrodes of a nanopore detector. Once the current recorded indicated a capture of a DNA in the nanopore (which could be a test DNA or the reference DNA (DNA-TR)), the electric potentials applied to the electrodes are changed linearly from 160 mV to 0 mV in 2 seconds. At approximately 0 mV a short negative potential pulse (approximately–40 mV for 0.5 seconds) is applied to eject the test molecule from the pore and this is followed by a return to the capture voltage of +160 mV for another capturelread cycle. When a reference DNA (DNA-TR) is captured, the DNA captured is released from the pore when the electric potential applied is about 40 mV. When a test DNA (DNA-TA, DNA-TT, DNA-TC or DNA-TG) is captured, the DNA captured is released after the electric potential applied reached about OmV. Thus, based on the electric potential at which the DNA captured is released from the pore, the DNA captured can be identified as the reference DNA or one of the test DNAs. Each experiment is carried out for approximately 30 minutes on one nanopore. The same experiments are repeated on three nanopores for each test DNAs, thus 12 sets of data are provided.

The currents recorded by the nanopore detector when the reference DNA is captured in the nanopore are referred herein as the reference reads. The currents recorded by the nanopore detector when the test DNA is captured in the nanopore are referred herein as the test reads. For a set of data having both test reads and the reference reads, the reference reads versus change of electric potential applied are fit into a quadratic line. The median of the reference reads vs. the changes of the electric potential is obtained (hereinafter the reference medians). The delta current between each test read and the reference medians are calculated for each electric potential applied and then divided by the derivative of the reference quadratic fit to obtain a ratio of the test reads to the reference reads. The conductance of the delta current is then multiplied by 100 to tum into % reference conductance difference. Then curves of the % reference conductance differences for the test reads versus electric potential applied (mV) are drafted and compiled. The curves show that single substitution of A, T, C, or G in a polyT DNA captured in a nanopore can be identified with more than 95% confidence as described herein. It is assumed that none of the other nucleotides but the single substituted nucleotide (A, T, C, and G) affects the signals obtained by the nanopore detector. With the electric potential(s) applied in steps (B6 to B7), either in a constant profile or a varied profile is (are) at least about 90 mV, preferably at least about 100 mV, more preferably about 100 mV to about 160 mV, C and Tare determined with high confidence(>about 99%, preferably>99.5% confidence). G and A are characterized with a lower confidence (about 95% confidence). The complementary structures of G and A are C and T, respectively. Thus, determining the C's and T's in the antisense strand provided the determination of G's and A's in the sample DNA with a higher confidence (>99%, preferably >99.5% confidence) as well. Therefore, determining the C's and T's in both the sample DNA and the antisense strand can provide the structure of the sample DNA with a higher confidence (>99%, preferably >99.5% confidence) than determining all four nucleotides A, C, T and G from information collected from the sample DNA only (about 95% confidence).

When the electric potential(s) applied in steps (B6B7), either in a constant profile or a varied profile is (are) less than about 80 mV, preferably less than about 70 mV, more preferably about 0mV to about 70 mV, C and A are determined with high confidence (>about 99%, preferably >99.5% confidence). G and T are characterized with a lower confidence (about 95% confidence). The complementary structures of G and T are C and A, respectively. Thus, determining the C's and A's in the antisense strand provided the determination of G's and T's in the sample DNA with a higher confidence (>99%, preferably >99.5% confidence) as well. Therefore, determining the C's and A's in both the sample DNA and the antisense strand can provide the structure of the sample DNA with a higher confidence (>99%, preferably >99.5% confidence) than determining all four nucleotides A, C, T and G from information collected from the sample DNA only (about 95% confidence). Thus, taking the electrical signals collected from the sample polynucleotide and the corresponding antisense structure together improved the confidence in resolving the structures in the sample polynucleotide.

The signals can be derived from a speed bump reading system as described earlier, from an enzyme extension system as described earlier, from an enzyme extension and disassociation of the enzyme from the sample reading system as described earlier, or from other enzyme/strand movement techniques including helicase enzyme strand movement as an example. Helicase does not require base extension of an antisense strand to move the sample strand in a nanopore but unravels the DNA sample in a linear fashion through the nanopore for reading.

Example 7

Nucleotide Dimmer Differentiations are Obtained via DNA Nanopore Detection

DNA stock solutions having 1.0 μM streptavidin and 4 μM of a DNA of PolyA$_{40}$ DNAs having single nucleotide substitution at position 12 from the 3' end (39A1Ns, DNA-AA, DNA-AT, DNA-AC and DNA-AG as shown below), polyC$_{40}$ DNAs having single nucleotide substitution at position 12 from the 3' end (39C1Ns, DNA-CA, DNA-CT, DNA-CC and DNA-CG as shown below), PolyT$_{40}$ DNAs having single nucleotide substitution at position 12 from the 3' end (39T1Ns, as in Example 6) or reference DNA 30C (DNA-CR as shown below) are prepared according to the method described in Example 6.

```
DNA-CA
5'-CCCCCCCCCCCCCCCCCCCCCCCCCCCACCCCCCCCCCC-Biotin-3'

DNA-CT
5'-CCCCCCCCCCCCCCCCCCCCCCCCCCCTCCCCCCCCCCC-Biotin-3'

DNA-CC
5'-CCCCCCCCCCCCCCCCCCCCCCCCCCCCCCCCCCCCCCC-Biotin-3'

DNA-CG
5'-CCCCCCCCCCCCCCCCCCCCCCCCCCCGCCCCCCCCCCC-Biotin-3'

DNA-AA
5'-AAAAAAAAAAAAAAAAAAAAAAAAAAAAAAAAAAAAAAA-
Biotin-3'

DNA-AT
5'-AAAAAAAAAAAAAAAAAAAAAAAAAAATAAAAAAAAAAA-
Biotin-3'

DNA-AG
5'-AAAAAAAAAAAAAAAAAAAAAAAAAAAGAAAAAAAAAAA-
Biotin-3'

DNA-AC
5'-AAAAAAAAAAAAAAAAAAAAAAAAAAACAAAAAAAAAAA-
Biotin-3'

DNA-TA
5'-TTTTTTTTTTTTTTTTTTTTTTTTTTTATTTTTTTTTTT
TT-Biotin-3'

DNA-TT
5'-TTTTTTTTTTTTTTTTTTTTTTTTTTTTTTTTTTTTTTT
TT-Biotin-3'

DNA-TG
5'-TTTTTTTTTTTTTTTTTTTTTTTTTTTGTTTTTTTTTTT
TT-Biotin-3'

DNA-TC
5'-TTTTTTTTTTTTTTTTTTTTTTTTTTTCTTTTTTTTTTT
TT-Biotin-3'

DNA-CR
5'-CCCCCCCCCCCCCCCCCCCCCCCCCCCCCC-Biotin-3'
```

The similar experiments as described in Example 6 are carried out for each test DNAs (DNA-AA, DNA-AT, DNA-AC, DNA-AG, DNA-CA, DNA-CT, DNA-CC, DNA-CG DNA-TA, DNA-TT, DNA-TC or DNA-TG) using DNA-CR as the reference DNA, except that the experiments are run at 0° C. instead of at room temperature. Experiments for all test DNAs are performed once, and the data obtained are processed as described in Example 6. The data complied shows that 2-base differences at positions 11 to 13 from the 3' end of the tests DNAs; comprised of 3 different homopolymer backbone strands can be identified reliably by DNA nanopore detection using a varied electric potential profile described herein. In an example electric potential profile, data is provided corresponding to DNAs having polyA-backbones, DNAs having polyC-backbones, and DNAs having polyT-backbones.

Published studies have shown that the constriction zone in the upper portion of the alpha hemolysin pore barrel is the major constriction zone in the pore and accounts for the majority of the current decrease when DNA is suspended in the pore. Without the intention to be bound by any theory, it is estimated that when a DNA is suspended in the pore a total of 10 nucleotides fit in the full length of the barrel of an alpha-hemolysin pore. The graph readings identified the 2 nucleotides in the constriction zone but data had not been taken on all possible combinations of the remaining 8 nucleotides in the pore. As presented in the literature, the reading levels of electric potential profiles assumes that the eight remaining nucleotides in the pore at the time of measurement did not appreciably affect the current readings of the 2-nucleotide pairs.

TABLE 1

Nucleotide dimers and corresponding complementary dimers in the antisense strand

| DNA | DNA-AA | DNA-AT | DNA-AC | DNA-AG | DNA-TA | DNA-TT | DNA-TC | DNA-TG | DNA-CA | DNA-CT | DNA-CC | DNA-CG |
|---|---|---|---|---|---|---|---|---|---|---|---|---|
| Dimer | AA | AT | AC | AG | TA | TT | TC | TG | CA | CT | CC | CG |
| Dimer (antisense) | TT | AT | GT | CT | TA | AA | GA | CA | TG | AG | GG | CG |

Electric potential profiles indicate that because dimers AC and TC are readily detectable, the corresponding antisense dimers GT and GA are readily detectable as well.

In an example, when the electric potential(s) applied in steps (B6 to B7) (applied either in a constant profile or a varied profile) is (are) at least about 130 mV, the electric potential profiles(% reference conductance difference as a function of voltage (mV)) show the following:

Signals of f G, TA and TI' are mixed together. The corresponding antisense dimers of TG, TA and TT are CA, TA and AA, respectively, which are easy to differentiate from each other.

Signals of AT, AA and AG are mixed together. The corresponding antisense dimers of AT, AA and AG are AT, TT and CT, respectively, which are easy to differentiate from each other.

Signals of CG, CA and CT are mixed together. The corresponding antisense dimers of CG, CA and CT are CG, TG and AG, respectively, CG and CT are difficult to differentiate from each other under the electric potential(s) of about 130 mV or higher, but are easy to differentiate from each other when the electric potential(s) applied in steps (B6 to B7) is (are) lower (e.g., around 100 mV). When the electric potential(s) applied in steps (B6 to B7), either in a constant profile or a varied profile, is (are) about 80 mV to about 120 mV:

Signals of TG, TA and TT are mixed together. The corresponding antisense dimers of TG, TA and TT are CA, TA and AA, respectively, which are easy to differentiate from each other.

Signals of AT, AA and AG are mixed together. The corresponding antisense dimers of AT, AA and AG are AT, TT and CT, respectively, which are easy to differentiate from each other.

Signals of CG, CA and CT are missed together. The corresponding antisense dimers of CG, CA and CT are CG, TG and AG, respectively, which are easy to differentiate from each other.

Thus, the method described herein provide a more reliable and accurate characterization of a sample DNA by characterizing both the sample DNA and the antisense DNA thereof.

Taking the electrical signals collected in the same nanopore for the sample polynucleotide and the corresponding antisense structure lowered systematic errors and improved the confidence in resolving the structures in the sample polynucleotide. Similar results can be expected when the sample poli-nucleotide is RNA and the antisense polynucleotide is DNA or RNA or man-made nucleotides.

The methods of sample preparation described herein are easy and can be applied to any nucleic acid sample. The methods of preparation described herein allow multiplexed samples on the same nanopore sensor. The sense/antisense sample preparation and reading techniques described herein may be ideal or otherwise suited for use on a nanopore sequencer or detector comprising an array individually controlled nanopore sensors. The ability to read the sense and antisense strand of the same region of sample DNA or RNA at nearly the same time and in the same nanopore lowers the systematic error, and improves the ability to correctly read and sequence the sample. As can be appreciated, the number of nanopore sensors in one array can be large and is limited only by semiconductor process technology. The ability to read the individual nucleic acid samples with high confidence at individual nanopores and the ability to read large numbers of samples in a massively parallel fashion using an array of nanopore sensors on one chip or on one detector, will allow simple, inexpensive, and portable DNA or RNA sequencing to become a reality.

Example 8

PolyT$_{40}$ DNAs Having Single Nucleotide Substitution at Position 12 from the 3' end (39T1Ns) are Distinguished from Each Other with a Greater Than 95% Confidence by DNA Nanopore Detection Using a Varied Electrical Potential Profile DNA-TA (5'-TTTTTTTTTTTTTTTTTTTTTTTTTTTT-TATTTTTTTTTTT-Biotin-3'), DNA-TT (5'-TTTTTT-TTTTTTTTTTTTTTTTTTTTTTTTTTTTTTTTTTTT-Biotin-3'), DNA-TC (5'-TTTTTTTTTTTTTTTTTTTTTTT-TTTTTTTCTTTTTTTTTTTT-Biotin-3'), DNA-TG (5'-TTTTTTTTTTTTTTTTTTTTTTTTTTTTGTTTTTT-TTTTT-Biotin-3'), and DNA-TR containing 30T (5'-TTTTTTTTTTTTTTTTTTTTTTTTTTTTTTT-Biotin-3') are synthesized. Each type of DNA (DNA-TA, DNA-TT, DNA-TC, DNA-TG and DNA-TR) is mixed individually with Streptavidin to a working concentration of 100 μM of DNA and 25 μM of Streptavidin. The obtained solutions are then further diluted to a final concentration of 4 μM of test DNA and 10 μM of Streptavidin as DNA stock solutions.

The tests are run on alpha hemolysin nanopore detectors. The nanopore detectors had a pair of silver electrodes embedded in a planar Teflon surface. Lipid bilayers are created by a bubble method or by sliding a pipette tip dipped in a small amount of lipid mix across the surface of the planar electrode using 1 μL of 15 mg/mL DPhPC lipid in Decane. Nanopores are prepared with up to 1 μL of 1 μg/mL Alpha Hemolysin in 20% Glycerol and water buffered to pH 8.0 with 20 mM HEPES. Alternatively, the nanopores are prepared with 1 to 100 ng/mL of alpha hermolysin porin.

In one experiment, 2 μL stock solution of the reference DNA (DNA-TR) and 2 μL stock solution of a test DNA (DNA-TA, DNA-TT, DNA-TC or DNA-TG) are mixed with 40 μL of 1 M KCl, pH 8.0, 20 mM HEPES buffered, double filtered solution and 4 μL of biology grade water are loaded on a nanopore detector prepared supra. The varied electric potential profile is applied by an external waveform generator, and the current flowing through the nanopore is recorded. An initial electric potential of 160 mV is applied to the electrodes of a nanopore detector. Once the current recorded indicated a capture of a DNA in the nanopore (which could be a test DNA or the reference DNA (DNA-TR)), the electric potential applied to the electrodes are changed linearly from 160 mV to 0 mV in 2 seconds. After the current recorded showed that the DNA captured is released from the nanopore, the electric potential applied to the nanopore detector is restored to 160 mV until the next DNA capture happened. When a reference DNA (DNA-TR) is captured, the DNA captured is released when the electric potential applied is about 40 mV. When a test DNA (DNA-TA, DNA-TT, DNA-TC or DNA-TG) is captured, the DNA captured is released after the electric potential applied is about 0mV. Thus, based on the electric potential at which the DNA captured is released, the DNA captured can be identified as the reference DNA or one of the test DNAs. The experiment is carried out for 30 minutes on one nanopore. The same experiments are repeated on three nanopores for each test DNAs, thus provided 12 sets of data.

The currents recorded by the nanopore detector when the reference DNA is captured in the nanopore may be referred to herein as the reference reads. The currents recorded by the nanopore detector when the test DNA is captured in the nanopore are referred herein as the test reads.

For a set of data having both test reads and the reference reads, the reference reads versus change of electric potential applied are fit into a quadratic line. The median of the reference reads vs. the changes of the electric potential is obtained (hereinafter the reference medians). The delta current between each test read and the reference medians are calculated for each electric potential applied and then divided by the derivative of the reference quadratic fit to obtain a ratio of the test reads to the reference reads. The conductance of the delta current is calculated and multiplied by 100 to turn into % reference conductance difference. Then curves of the % reference conductance differences for the test reads versus electric potential applied (mV) are drafted and complied to provide an electric potential profile (graph). A first set of curves show data obtained from DNA-TA, a second set of curves show data obtained from DNA-TG, a third set of curves show data obtained from DNA-TT, and a fourth set of curves show data obtained from DNA-TC. The electric potential profile shows that single substitution of A, T, C, or G in a polyT DNA captured in a nanopore can be identified with more than 95% confidence as described herein.

Example 2

Single Nucleotide Differentiation of A, T, C and G are Obtained via DNA Nanopore Detection by Applying a Varied Electric Potential to the Electrodes of the Nanopore Detector DNA stock solutions having 1.0 µM streptavidin and 4 µM of a DNA of PolyA$_{40}$ DNAs having single nucleotide substitution at position 12 from the 3' end (39A1Ns, DNA-AA, DNA-AT, DNA-AC and DNA-AG as shown below), polyC$_{40}$ DNAs having single nucleotide substitution at position 12 from the 3' end (39C1Ns, DNA-CA, DNA-CT, DNA-CC and DNA-CG as shown below), PolyT$_{40}$ DNAs having single nucleotide substitution at position 12 from the 3' end (39T1Ns, as in Example 8) or reference DNA 30C (DNA-CR as shown below) are prepared according to the method described in Example 8.

```
DNA-CA
5'-CCCCCCCCCCCCCCCCCCCCCCCCCCCACCCCCCCCCCC-Biotin-3'

DNA-CT
5'-CCCCCCCCCCCCCCCCCCCCCCCCCCCTCCCCCCCCCCC-Biotin-3'

DNA-CC
5'-CCCCCCCCCCCCCCCCCCCCCCCCCCCCCCCCCCCCCCC-Biotin-3'

DNA-CG
5'-CCCCCCCCCCCCCCCCCCCCCCCCCCCGCCCCCCCCCCC-Biotin-3'

DNA-AA
5'-AAAAAAAAAAAAAAAAAAAAAAAAAAAAAAAAAAAAAAAA-
Biotin-3'

DNA-AT
5'-AAAAAAAAAAAAAAAAAAAAAAAAAAATAAAAAAAAAAAA-
Biotin-3'

DNA-AG
5'-AAAAAAAAAAAAAAAAAAAAAAAAAAAGAAAAAAAAAAAA-
Biotin-3'

DNA-AC
5'-AAAAAAAAAAAAAAAAAAAAAAAAAAACAAAAAAAAAAAA-
Biotin-3'

DNA-TA
5'-TTTTTTTTTTTTTTTTTTTTTTTTTTTTATTTTTTTTTTT
TT-Biotin-3'

DNA-TT
5'-TTTTTTTTTTTTTTTTTTTTTTTTTTTTTTTTTTTTTTTT
TT-Biotin-3'

DNA-TG
5'-TTTTTTTTTTTTTTTTTTTTTTTTTTTTTGTTTTTTTTTT
TT-Biotin-3'

DNA-TC
5'-TTTTTTTTTTTTTTTTTTTTTTTTTTTTTCTTTTTTTTTT
TT-Biotin-3'

DNA-CR
5'-CCCCCCCCCCCCCCCCCCCCCCCCCCCCCCC-Biotin-3'
```

The similar experiments as described in Example 8 are carried out for each test DNAs (DNA-AA, DNA-AT, DNA-AC, DNA-AG, DNA-CA, DNA-CT, DNA-CC, DNA-CG DNA-TA, DNA-TT, DNA-TC or DNA-TG) using DNA-CR as the reference DNA, except that the experiments are run at 0° C. instead of at room temperature. Experiments for all test DNAs are performed once, and the data obtained are processed as described in Example 8. The data complied showed that 2-base differences at positions 11 to 13 from the 3' end of the tests DNAs, comprised of 3 different homopolymer backbone strands could be identified reliably by DNA nanopore detection using a varied electric potential profile described herein. In an example electric potential profile, data for DNAs having polyA-backbones, data for DNAs having polyC-backbones, and data for DNAs having polyT-backbones is provided. A first set of curves is from data for DNA-AA, DNA-CA and DNA-TA; a second set of curves is from data for DNA-AC, DNA-CC and DNA-TC; a third set of curves is from data for DNA-AT, DNA-CT and DNA-TT; and a fourth set of curves is from data for DNA-AG, DNA-CG and DNA-TG.

Data obtained from experiments of 39A1Ns described is used to generate an electric potential profile showing percent reference conductance difference as a function of voltage (V). A first set of curves is generated from data for DNA-AA, a second set of curves is generated from data for DNA-AC; a third set of curves is generated from data for DNA-AT; and a fourth set of curves is generated from data for DNA-AG.

Data obtained from experiments of 39C1Ns described herein is used to generate an electric potential profile showing percent reference conductance difference as a function of voltage (V). A first set of curves is generated from data for DNA-CA; a second set of curves is generated from data for DNA-CC; a third set of curves is generated from data for DNA-CT; and a fourth set of curves is generated from data for DNA-CG.

Data obtained from experiments of 39T1Ns described herein is used to generate an electric potential profile showing percent reference conductance difference as a function of voltage (V) shown. A first set of curves is generated from data for DNA-TA; a second set of curves is generated from data for DNA-TC; a third set of curves is generated from data for DNA-TT; and a fourth set of curves is generated from data for DNA-TG.

All data shows that single A, T, C, or G in a homopolymer DNA (polyA polyC or polyT) captured in a nanopore is identified with more than 95% confidence.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

---

What is claimed is:

1. A system for identifying a nucleotide or nucleotide analog or portion thereof, the system comprising:
   a chip comprising at least one cell, the cell comprising an electrode pair and a nanopore disposed in a membrane, wherein the electrode pair is associated with a variable voltage source and configured to apply a variable voltage across the nanopore of the membrane;
   a memory device comprising code instructions, and
   a processor communicatively coupled to the memory device, wherein the processor is configured to execute the code instructions that are stored in the memory device to cause the system to:
   vary the voltage applied across the nanopore when a nucleotide or nucleotide analog or portion thereof is inserted into the nanopore, wherein the voltage is varied across a range of voltages from 120 mV to 150 mV;
   measure an electrical signal at a plurality of applied voltages with at least one of the electrode pair while the nucleotide or nucleotide analog or portion thereof is inserted within the nanopore; and identify the nucleotide or nucleotide analog or portion thereof that is inserted within the nanopore based on the measured electrical signal at the plurality of applied voltages.

2. The system of claim 1, wherein varying the voltage across the range from 120 mV to 150 mV distinguishes one nucleotide from a different nucleotide.

3. The system of claim 1, wherein the electrical signal is current.

4. The system of claim 1, wherein the electrical signal is conductance.

5. The system of claim 1, wherein the nucleotide or nucleotide analog is a tag molecule.

6. The system of claim 1, wherein the voltage is varied according to a voltage waveform.

7. The system of claim 6, wherein the voltage waveform is a square wave, a sinusoidal wave, a triangular wave, a saw-tooth wave, or an irregular wave.

8. The system of claim 1, wherein the voltage is ramped from a first voltage to a second voltage.

9. The system of claim 1, wherein varying the voltage comprises applying a first voltage for a first time period and a second voltage for a second time period.

10. The system of claim 9, wherein the first voltage and the second voltage have a difference of at least 1 mV.

11. The system of claim 9, wherein the first voltage and the second voltage have a difference of at least 10 mV.

12. The system of claim 9, wherein the first time period and the second time period is at least 5 µs.

\* \* \* \* \*

SEQUENCE LISTING

<160> NUMBER OF SEQ ID NOS: 21

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cccccccccc ttataccct ataa                                             24

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgtctagcgt tgccgaaaac ggcaacgcta gacg                                 34

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gaccctgccc ccagctttcc ccaaacgtca aaaaa                                35

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cccccccccc gcgc                                                          14

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tttttttttt gcgc                                                          14

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tttttttttt tttttttttt tttttttttt tttttttttt                              40

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tttttttttt tttttttttt ttttttttat tttttttttt                              40

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tttttttttt tttttttttt ttttttttct tttttttttt                              40

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tttttttttt tttttttttt ttttttttgt tttttttttt                              40

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tttttttttt tttttttttt tttttttttt                                         30

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaaaaaaaaa aaaaaaaaaa aaaaaaaaaa aaaaaaaaaa                          40

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cccccccccc cccccccccc cccccccccc cccccccccc                          40

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cccccccccc cccccccccc ccccccccac cccccccccc                          40

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cccccccccc cccccccccc ccccccccatc cccccccccc                         40

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cccccccccc                                                           10

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cccccccccc cccccccccc ccccccccgc cccccccccc                          40

```
<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aaaaaaaaaa aaaaaaaaaa aaaaaaaata aaaaaaaaaa                               40

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aaaaaaaaaa aaaaaaaaaa aaaaaaaga aaaaaaaaaa                                40

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aaaaaaaaaa aaaaaaaaaa aaaaaaaca aaaaaaaaaa                                40

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cccccccccc cccccccccc cccccccccc                                          30

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tttttttttt                                                                10
```